United States Patent
Kadamus et al.

(10) Patent No.: US 10,765,474 B2
(45) Date of Patent: Sep. 8, 2020

(54) INJECTATE DELIVERY DEVICES, SYSTEMS AND METHODS

(71) Applicant: Fractyl Laboratories, Inc., Lexington, MA (US)

(72) Inventors: Christopher J. Kadamus, Jamaica Plain, MA (US); Mark A. Manasas, Lexington, MA (US); Andrew Coats, Somerville, MA (US); Jay Caplan, Belmont, MA (US); Harith Rajagopalan, Wellesley Hills, MA (US); R. Maxwell Flaherty, Auburndale, FL (US); J. Christopher Flaherty, Auburndale, FL (US)

(73) Assignee: Fractyl Laboratories, Inc., Lexington, MA (US)

( * ) Notice: Subject to any disclaimer, the term of this patent is extended or adjusted under 35 U.S.C. 154(b) by 374 days.

(21) Appl. No.: 15/274,948

(22) Filed: Sep. 23, 2016

(65) Prior Publication Data
US 2017/0007324 A1    Jan. 12, 2017

Related U.S. Application Data

(63) Continuation of application No. PCT/US2015/022293, filed on Mar. 24, 2015, which
(Continued)

(51) Int. Cl.
*A61B 18/14* (2006.01)
*A61M 25/00* (2006.01)
(Continued)

(52) U.S. Cl.
CPC ........ *A61B 18/1492* (2013.01); *A61B 5/4836* (2013.01); *A61B 5/6847* (2013.01);
(Continued)

(58) Field of Classification Search
CPC .......... A61B 18/1492; A61B 17/12186; A61B 5/6847; A61B 5/4836; A61B 2018/1472;
(Continued)

(56) References Cited

U.S. PATENT DOCUMENTS

| 5,084,044 A | 1/1992 | Quint |
| 5,190,540 A | 3/1993 | Lee |

(Continued)

FOREIGN PATENT DOCUMENTS

| CA | 2666661 C | 1/2015 |
| CN | 1771888 A | 5/2006 |

(Continued)

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
(Continued)

*Primary Examiner* — Tan-Uyen T Ho
*Assistant Examiner* — Chima U Igboko
(74) *Attorney, Agent, or Firm* — Wilson Sonsini Goodrich & Rosati

(57) ABSTRACT

An injectate delivery device for expanding tissue is provided. The injectate delivery device comprises: at least one fluid delivery tube comprising a proximal end, a distal end and a lumen therebetween; at least one fluid delivery element in fluid communication with the at least one fluid delivery tube lumen; a radially expanding element comprising the at least one fluid delivery element; a supply of vacuum constructed and arranged to cause tissue to tend toward the at least one fluid delivery element; and at least one control constructed and arranged to perform a function. The at least one control can be constructed and arranged to
(Continued)

expand the radially expandable element and activate the supply of vacuum. Systems and method of injectate delivery are also provided.

55 Claims, 12 Drawing Sheets

Related U.S. Application Data is a continuation of application No. PCT/US2014/066829, filed on Nov. 21, 2014, and a continuation of application No. 14/515,324, filed on Oct. 15, 2014, and a continuation of application No. 14/470,503, filed on Aug. 27, 2014.

(60) Provisional application No. 61/969,417, filed on Mar. 24, 2014.

(51) Int. Cl.
  *A61M 25/04* (2006.01)
  *A61B 5/00* (2006.01)
  *A61M 29/02* (2006.01)
  *A61M 29/00* (2006.01)
  *A61B 17/12* (2006.01)

(52) U.S. Cl.
  CPC ..... *A61B 17/12186* (2013.01); *A61M 25/0074* (2013.01); *A61M 25/0084* (2013.01); *A61M 25/04* (2013.01); *A61M 29/00* (2013.01); *A61M 29/02* (2013.01); *A61B 18/1477* (2013.01); *A61B 2018/1472* (2013.01); *A61M 2025/009* (2013.01); *A61M 2025/0087* (2013.01); *A61M 2025/0089* (2013.01); *A61M 2025/0092* (2013.01)

(58) Field of Classification Search
  CPC .......... A61B 18/1477; A61M 25/0084; A61M 29/00; A61M 29/02; A61M 25/0074; A61M 25/04; A61M 2025/009; A61M 2025/0087; A61M 2025/0089; A61M 2025/0092
  See application file for complete search history.

(56) References Cited

U.S. PATENT DOCUMENTS

| | | |
|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,864,961 A * | 2/1999 | Vaughan .............. A61B 5/1076 33/512 |
| 5,869,037 A | 2/1999 | Crystal et al. |
| 5,871,525 A | 2/1999 | Edwards et al. |
| 5,879,347 A | 3/1999 | Saadat |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,844,641 B2 | 12/2017 | Rajagopalan et al. |
| 10,610,663 B2 | 4/2020 | Rajagopalan et al. |
| 2002/0013581 A1* | 1/2002 | Edwards ................ A61B 18/12 606/41 |
| 2002/0115992 A1* | 8/2002 | Utley ..................... A61B 18/12 606/41 |
| 2003/0040804 A1 | 2/2003 | Stack et al. |
| 2003/0093072 A1 | 5/2003 | Friedman |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2004/0243211 A1* | 12/2004 | Colliou ............. A61N 1/36007 607/133 |
| 2005/0096638 A1 | 5/2005 | Starkebaum et al. |

(56) References Cited

U.S. PATENT DOCUMENTS

| | | |
|---|---|---|
| 2005/0154386 A1* | 7/2005 | West .............. A61B 18/1492 606/41 |
| 2005/0165437 A1 | 7/2005 | Takimoto |
| 2005/0171524 A1 | 8/2005 | Stern et al. |
| 2005/0203489 A1 | 9/2005 | Saadat et al. |
| 2005/0222558 A1 | 10/2005 | Baxter et al. |
| 2005/0251116 A1 | 11/2005 | Steinke et al. |
| 2005/0273090 A1 | 12/2005 | Nieman et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van Der Weide et al. |
| 2008/0207994 A1 | 8/2008 | Gonon |
| 2008/0243112 A1 | 10/2008 | De Neve |
| 2008/0275445 A1 | 11/2008 | Kelly et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0177192 A1* | 7/2009 | Rioux .............. A61B 18/1492 606/33 |
| 2009/0270851 A1 | 10/2009 | Babkin et al. |
| 2010/0022891 A1* | 1/2010 | Zuluaga .............. A61B 5/0084 600/473 |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1* | 8/2010 | Gostout ............. A61B 1/00094 600/565 |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0319809 A1 | 12/2011 | Smith |
| 2012/0004654 A1 | 1/2012 | Jackson et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1* | 12/2013 | Rajagopalan .......... A61N 7/022 604/506 |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0081745 A1 | 3/2016 | Rajagopalan et al. |
| 2016/0256663 A1 | 9/2016 | Rajagopalan et al. |
| 2016/0310200 A1 | 10/2016 | Wang |
| 2016/0354144 A1 | 12/2016 | Caplan et al. |
| 2017/0007310 A1 | 1/2017 | Rajagopalan et al. |
| 2017/0014596 A1 | 1/2017 | Rajagopalan et al. |
| 2017/0191035 A1 | 7/2017 | Sia et al. |
| 2018/0193078 A1 | 7/2018 | Rajagopalan et al. |
| 2018/0221622 A1 | 8/2018 | Rajagopalan et al. |
| 2020/0001047 A1 | 1/2020 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02102453 A2 | 12/2002 |
| WO | WO-03033045 A2 | 4/2003 |
| WO | WO-03092609 A2 | 11/2003 |
| WO | WO-2006020370 A2 | 2/2006 |
| WO | WO-2007044244 A2 | 4/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |
| WO | WO-2019136240 A1 | 7/2019 |

OTHER PUBLICATIONS

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.

Cherrington, et al. Hydrothermal Duodenal Mucosal Resurfacing: Role in the Treatment of Metabolic Disease. Gastrointest Endosc Clin N Am. Apr. 2017;27(2):299-301. doi: 10.1016/j.giec.2016.12.002.

Co-pending U.S. Appl. No. 15/406,572, filed Jan. 13, 2017.

European search report and search opinion dated Mar. 8, 2016 for EP Application No. 13825257.2.

(56) References Cited

OTHER PUBLICATIONS

European search report and search opinion dated Mar. 17, 2016 for EP Application No. 13827149.9.
European search report and search opinion dated Aug. 4, 2015 for EP Application No. 13755156.0.
European search report and search opinion dated Nov. 25, 2015 for EP Application No. 13777572.2.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Office Action dated Jan. 13, 2017 for U.S. Appl. No. 14/609,332.
Office action dated Feb. 29, 2016 for U.S. Appl. No. 14/609,334.
Office Action dated Mar. 7, 2017 for U.S. Appl. No. 15/274,764.
Office Action dated Mar. 7, 2017 for U.S. Appl. No. 15/274,809.
Office action dated Mar. 12, 2015 for U.S. Appl. No. 13/945,138.
Office Action dated Mar. 23, 2017 for U.S. Appl. No. 13/945,138.
Office action dated Mar. 28, 2016 for U.S. Appl. No. 14/673,565.
Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office Action dated Sep. 23, 2016 for U.S. Appl. No. 14/515,324.
Office Action dated Oct. 7, 2016 for U.S. Appl. No. 13/945,138.
Office Action dated Nov. 15, 2016 for U.S. Appl. No. 14/609,334.
Office action dated Nov. 30, 2015 for U.S. Appl. No. 13/945,138.
Office action dated Dec. 17, 2015 for U.S. Appl. No. 14/515,324.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
Co-pending U.S. Appl. No. 15/683,713, filed Aug. 22, 2017.
European Search Report and Search Opinion dated Aug. 7, 2017 for European Patent Application No. EP14864511.2.
European Search Report and Search Opinion dated Aug. 7, 2017 for European Patent Application No. EP15768945.6.
Notice of Allowance dated Sep. 14, 2017 for U.S. Appl. No. 15/274,809.
Office Action dated Nov. 2, 2017 for U.S. Appl. No. 15/156,585.
European search report with written opinion dated Feb. 1, 2018 for EP Application No. 15822378.
European search report with written opinion dated Dec. 2, 2016 for EP Application No. 14807116.
International search report with written opinion dated Jan. 9, 2018 for PCT/US2017/061074.
"Office Action date Jul. 11, 2018 for U.S. Appl. No. 14/917,243.".
"Office Action date Aug. 9, 2018 for U.S. Appl. No. 14/673,565.".
Office action dated Jan. 8, 2018 for U.S. Appl. No. 14/609,334.
Office action dated Mar. 19, 2018 for U.S. Appl. No. 14/470,503.
Office action dated Apr. 4, 2018 for U.S. Appl. No. 15/156,585.
Office action dated May 18, 2018 for U.S. Appl. No. 14/956,710.
"Office action dated Sep. 7, 2018 for U.S. Appl. No. 14/609,332.".
Office action dated Nov. 16, 2017 for U.S. Appl. No. 14/609,332.
Office action dated Nov. 30, 2017 for U.S. Appl. No. 14/673,565.
Office action dated Dec. 18, 2017 for U.S. Appl. No. 14/515,324.
Office action dated Dec. 19, 2017 for U.S. Appl. No. 13/945,138.
Co-pending U.S. Appl. No. 16/379,554, filed Apr. 9, 2019.
Co-pending U.S. Appl. No. 16/400,491, filed May 1, 2019.
Co-pending U.S. Appl. No. 16/438,362, filed Jun. 11, 2019.
Co-pending U.S. Appl. No. 16/711,236, filed Dec. 11, 2019.
Co-pending U.S. Appl. No. 16/742,645, filed Jan. 14, 2020.
EP12736438.8 The Extended European Search Report dated Nov. 22, 2016.
EP14844285.8 The Extended European Search Report dated Apr. 25, 2017.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Grikscheit, et al. Tissue-engineered small intestine improves recovery after massive small bowel resection. Ann Surg., 2004, 240:748-754.
Office action dated Mar. 7, 2019 for U.S. Appl. No. 13/945,138.
Office action dated Mar. 7, 2019 for U.S. Appl. No. 14/673,565.
Office action dated May 16, 2019 for U.S. Appl. No. 14/515,324.
Office action dated Jun. 6, 2019 for U.S. Appl. No. 15/683,713.
Office action dated Oct. 4, 2018 for U.S. Appl. No. 14/515,324.
Office action dated Nov. 2, 2018 for U.S. Appl. No. 14/609,334.
Office action dated Dec. 18, 2018 for U.S. Appl. No. 14/470,503.
PCT/US14/66829 International Search Report dated Feb. 20, 2015.
PCT/US2019/012338 International Search Report dated Apr. 15, 2019.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
U.S. Appl. No. 15/406,572 Office Action dated Feb. 7, 2019.
U.S. Appl. No. 15/406,572 Office Action dated Nov. 15, 2019.

(56) References Cited

OTHER PUBLICATIONS

U.S. Appl. No. 14/470,503 Notice of Allowance dated Feb. 27, 2019.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 13/945,138 Office Action dated Dec. 10, 2019.
U.S. Appl. No. 16/267,771 Office Action dated Feb. 6, 2020.
Co-pending U.S. Appl. No. 16/798,117, filed Feb. 21, 2020.
U.S. Appl. No. 15/406,572 Office Action dated Apr. 14, 2020.
U.S. Appl. No. 14/515,324 Office Action dated Mar. 31, 2020.
U.S. Appl. No. 15/683,713 Notice of Allowance dated Mar. 10, 2020.

* cited by examiner

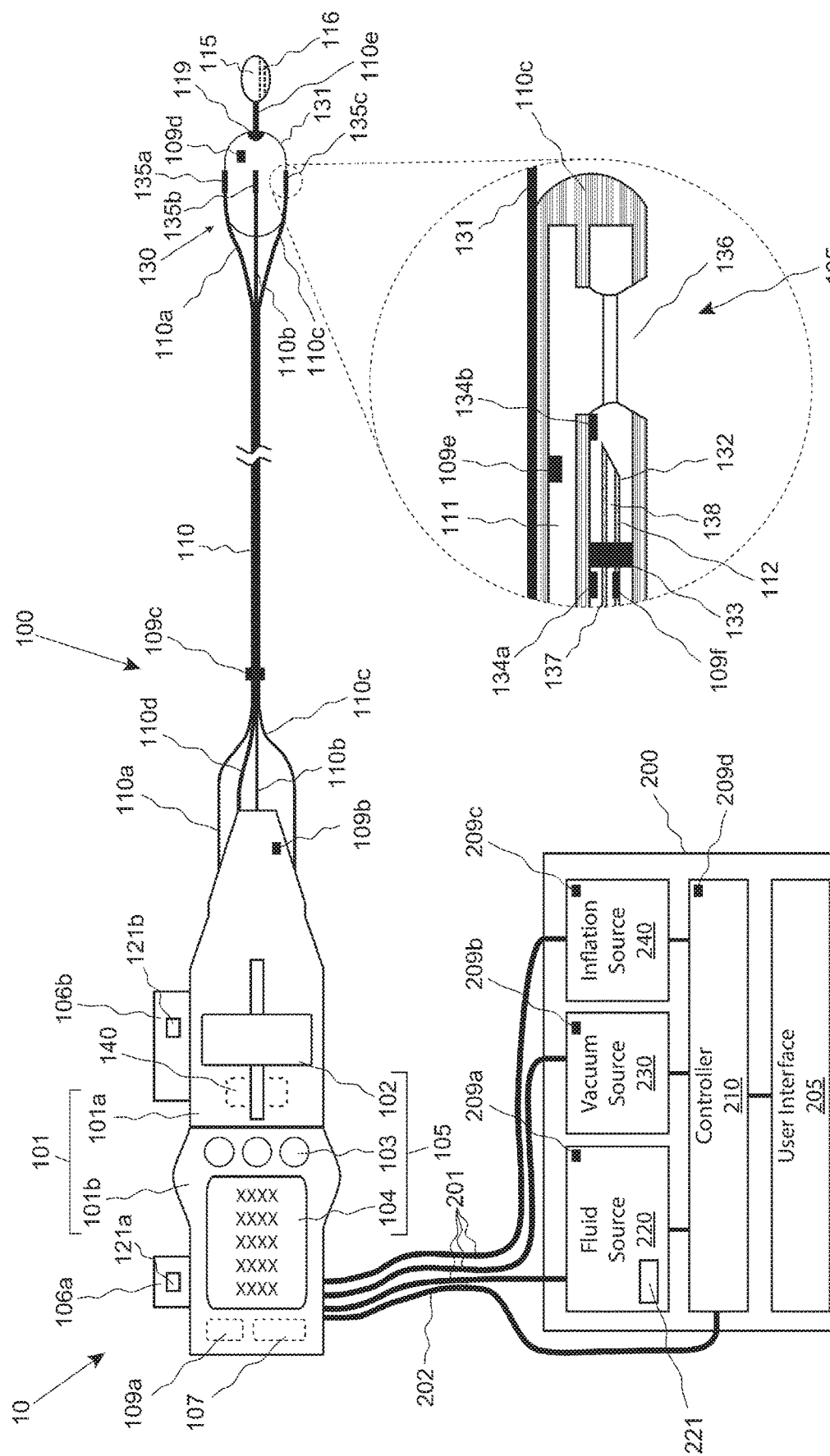

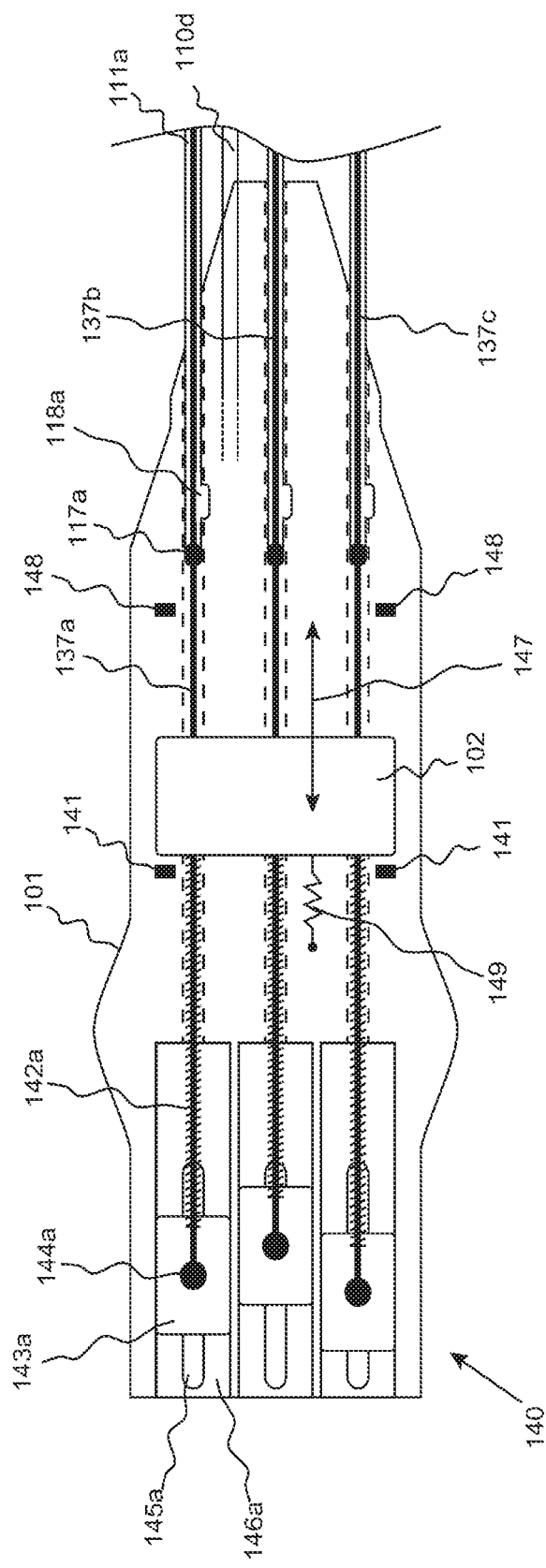
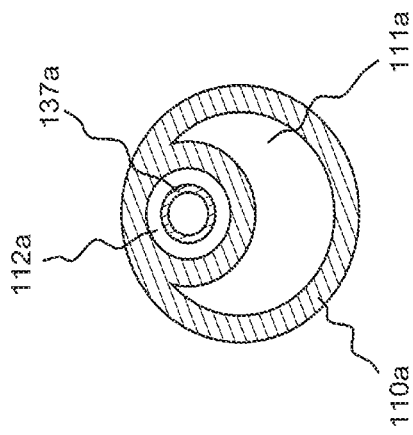
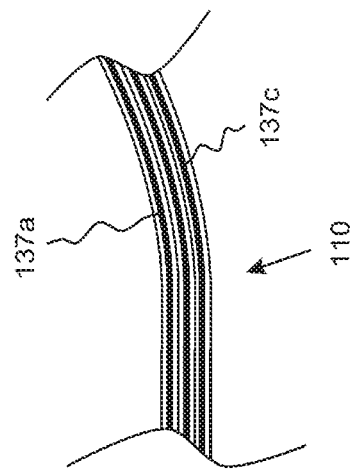

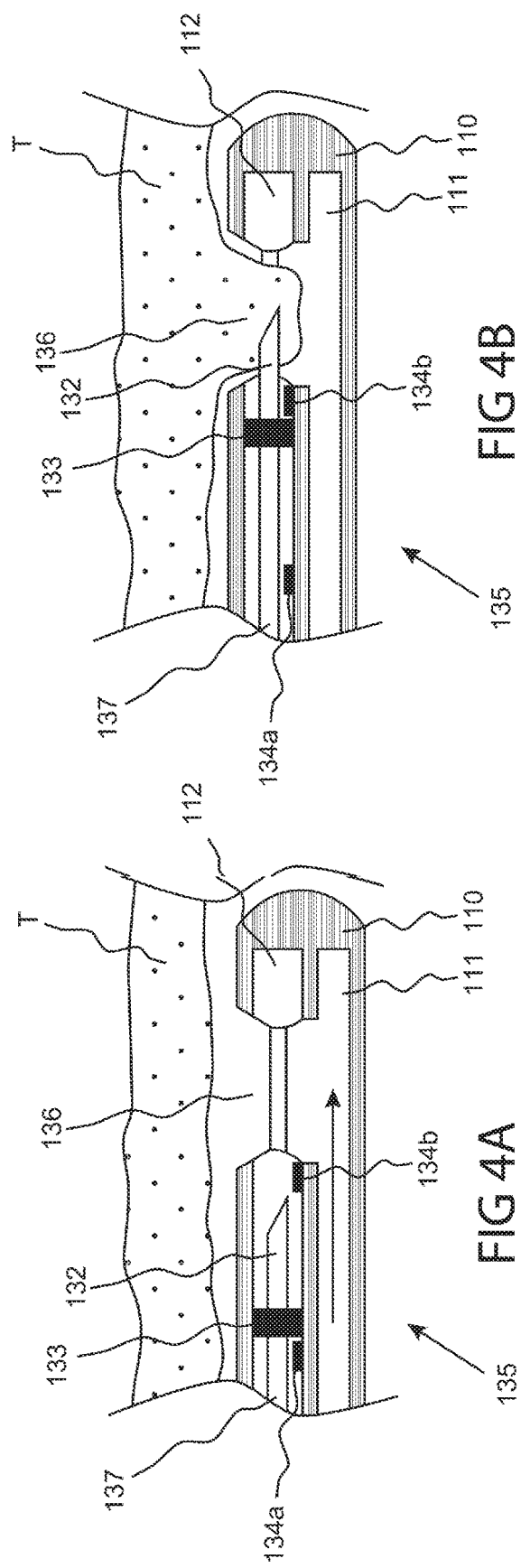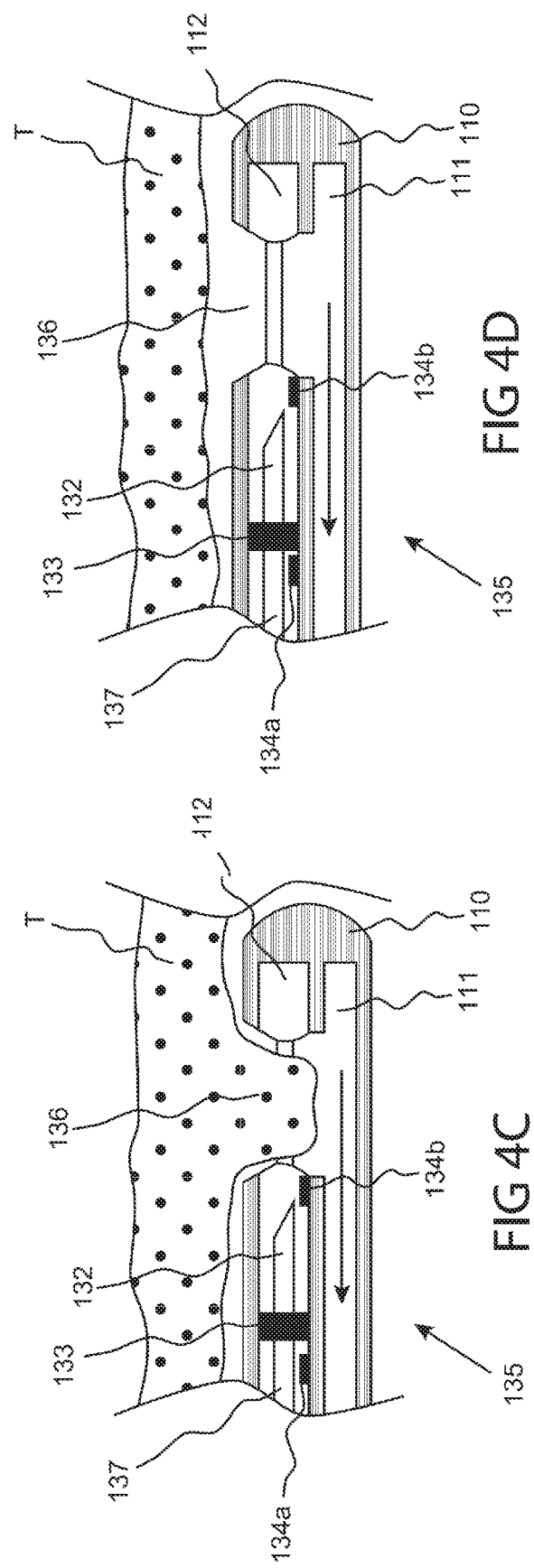

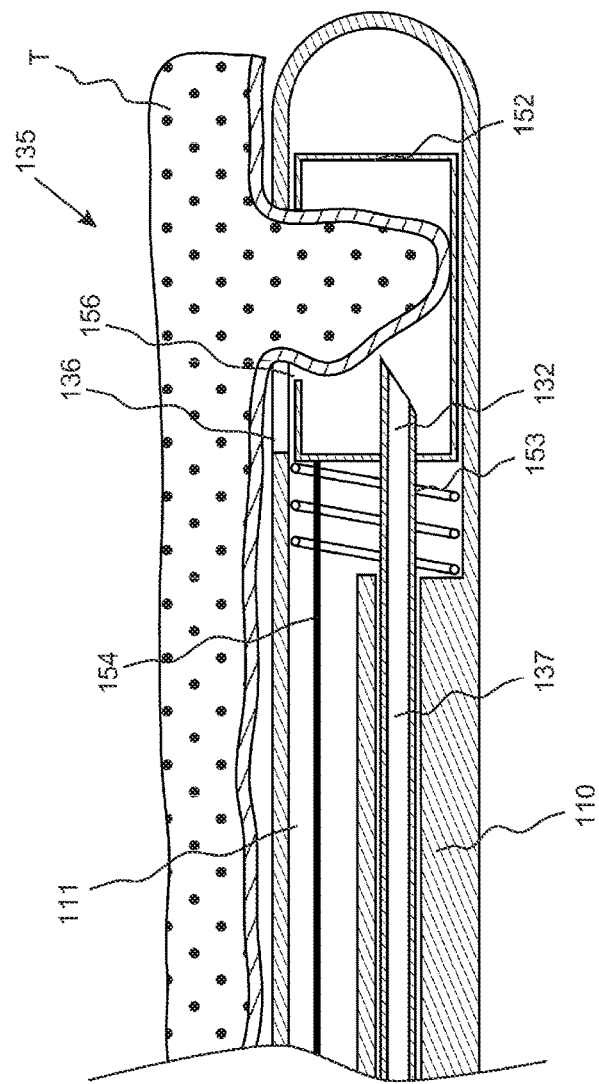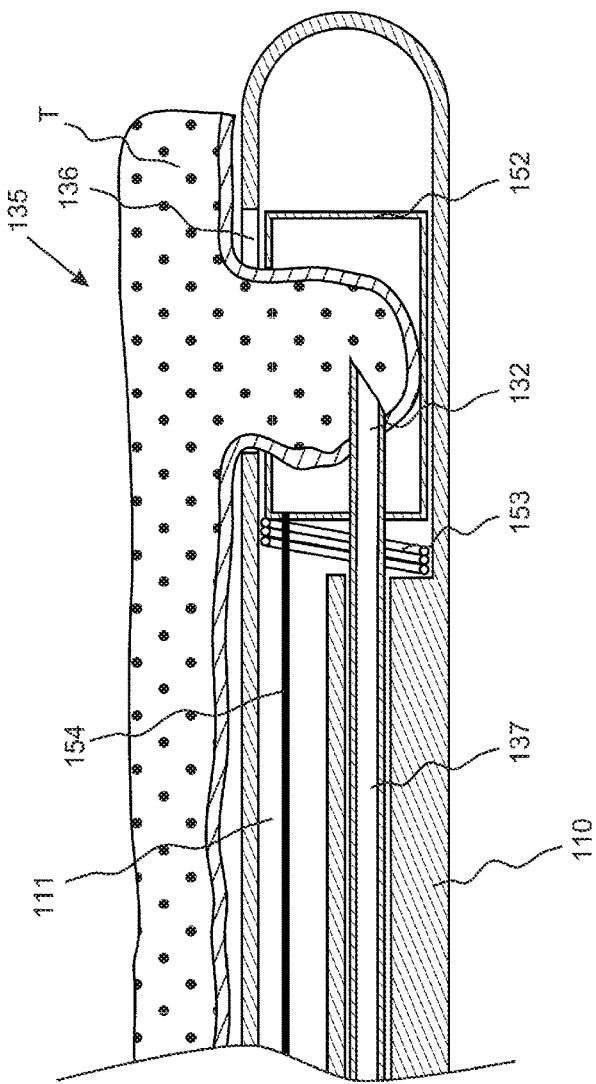

INJECTATE DELIVERY DEVICES, SYSTEMS AND METHODS

CROSS-REFERENCE TO RELATED APPLICATIONS

This application is a continuation of International Patent Application No. PCT/US2015/022293, filed Mar. 24, 2015, which is a continuation of International Patent Application No. PCT/US2014/066829, filed Nov. 21, 2014; PCT/US2015/022293, filed Mar. 24, 2015, and is a continuation of U.S. patent application Ser. No. 14/515,324, filed Oct. 15, 2014; and is a continuation of U.S. patent application Ser. No. 14/470,503, filed Aug. 27, 2014; PCT/US2015/022293, filed Mar. 24, 2015, also claims the benefit of U.S. Provisional Patent Application Ser. No. 61/969,417, filed Mar. 24, 2014; the entire content of which are incorporated herein by reference.

This application is related to U.S. patent application Ser. No. 13/945,138, entitled "Devices and Methods for the Treatment of Tissue", filed Jul. 18, 2013; the contents of which are each incorporated herein by reference in their entirety.

TECHNICAL FIELD

The embodiments disclosed herein relate generally to systems, devices and methods for delivering injectate, particularly for delivering injectate to expand one or more layers of gastrointestinal tissue.

BACKGROUND OF THE INVENTION

The field of gastrointestinal endoscopy has for many years focused on diagnostic and therapeutic techniques to observe, modify and remove tissues located in the digestive tract. For example, prior to a procedure to remove or otherwise modify tissue, a method referred to in the art as "lift and cut" involves the injection of saline or other biocompatible solution beneath the submucosa in an attempt to elevate and/or expand the submucosa, thereby changing the geometry to make it suitable for treatment, for example resection of tissue. In some cases, an injection catheter is used to deliver the fluid within the submucosal layer, which does not readily dissipate, throughout the target area, and once the target resection area has been elevated and/or expanded, the tissue can be treated.

However, the current devices, systems and methods for expanding submucosal and other tissue layers are cumbersome, inaccurate, and have a limited effected tissue area. Therefore, there is a need for improved devices, systems and methods for expanding submucosal and other tissue layers that provide simplified use, larger expansion areas, and reduced procedure time.

BRIEF SUMMARY OF THE INVENTION

According to one aspect of the present inventive concepts, an injectate delivery device for expanding tissue comprises: at least one fluid delivery tube comprising a proximal end, a distal end and a lumen therebetween; at least one fluid delivery element in fluid communication with the at least one fluid delivery tube lumen; and at least one control. The at least one control can be constructed and arranged to perform one or more functions, such as a function selected from the group consisting of: advance the at least one fluid delivery element while limiting force applied to fluid delivery element; activate a supply of vacuum constructed and arranged to move tissue toward the at least one fluid delivery element; manipulate tissue toward the fluid delivery element such that the fluid delivery element penetrates the tissue; initiate the flow of injectate through the at least one fluid delivery element and into tissue; modify the flow of injectate into tissue; expand a radially expandable element comprising the at least one fluid delivery element; compact a radially compactable element comprising the at least one fluid delivery element; control a separate device; and combinations thereof. The injectate delivery device can be constructed and arranged to deliver an injectate to target tissue through the at least one fluid delivery element.

In some embodiments, the at least one control comprises multiple controls.

In some embodiments, the injectate delivery device further comprises a handle, and the handle comprises the at least one control. The at least one control can comprise one or more controls selected from the group consisting of: electrical control; mechanical control; button; knob; switch; lever; touchscreen; and combinations thereof. The injectate delivery device can further comprise a fluid delivery assembly, and the at least one control can be configured to control a fluid delivery assembly parameter. The at least one control can be configured to at least one of: initiate; regulate; modify; or stop injectate delivery from the fluid delivery assembly. The controlled fluid delivery assembly parameter can comprise a parameter selected from the group consisting of: injectate flow rate; injectate flow duration; volume of injectate delivered; injectate temperature; injectate pressure; a threshold parameter; injectate type; and combinations thereof. The fluid delivery assembly can comprise a source of ablation energy, and the controlled fluid delivery assembly parameter can comprise a parameter selected from the group consisting of: flow rate of ablative fluid; volume of ablative fluid; pressure of ablative fluid; temperature of ablative fluid; type of energy delivered; type of RF energy delivered such as monopolar, bipolar or both; amount of RF energy delivered such as voltage, current and/or power delivered; and combinations thereof.

In some embodiments, the injectate delivery device further comprises a second device, and the at least one control controls the second device. The second device can comprise an endoscope. The at least one control can be constructed and arranged to control insufflation delivered with the endoscope. The second device can comprise an energy delivery device. The at least one control can be constructed and arranged to modify energy delivered by the energy delivery device. The second device can comprise a fluid delivery assembly. The at least one control can be constructed and arranged to modify injectate or other fluid delivered by the fluid delivery assembly.

In some embodiments, the injectate delivery device further comprises a fluid delivery assembly, and the fluid delivery assembly can comprise the at least one control.

In some embodiments, the at least one control is constructed and arranged to advance the at least one fluid delivery element. The at least one control can be constructed and arranged to advance the at least one fluid delivery tube. The injectate delivery device can be constructed and arranged to limit the force applied to the at least one fluid delivery tube during advancement. The injectate delivery device can further comprise a compression element operably connecting the at least one control to the at least one fluid delivery tube. The compression element can comprise a spring. The compression element can be constructed and arranged to avoid full compression. The at least one control can be constructed and arranged to advance the at least one fluid delivery element approximately 4 mm. The at least one control can be constructed and arranged to advance the at least one fluid delivery element at least 1 mm. The at least one control can be constructed and arranged to advance the at least one fluid delivery element at least 2 mm. The at least one control can be constructed and arranged to advance the at least one fluid delivery element no more than 6 mm. The at least one control can be constructed and arranged to advance the at least one fluid delivery element no more than 5 mm. The at least one fluid delivery tube can comprise multiple fluid delivery tubes and the at least one fluid delivery element can comprise multiple fluid delivery elements each attached to a fluid delivery tube, and the at least one control can be constructed and arranged to advance the multiple fluid delivery tubes. The at least one control can comprise a single control constructed and arranged to advance the multiple fluid delivery tubes simultaneously. The injectate delivery device can be constructed and arranged to limit the force applied to each of the multiple fluid delivery tubes. The injectate delivery device can be constructed and arranged to independently limit the force applied to each of the multiple fluid delivery tubes. The injectate delivery device can further comprise multiple compression elements, and each compression element can operably connect one of the multiple fluid delivery tubes to the at least one control. The multiple compression elements can comprise multiple springs. The multiple compression elements can each be constructed and arranged to avoid full compression.

In some embodiments, the injectate delivery device further comprises at least one vacuum lumen, and the at least one control can be constructed and arranged to initiate a vacuum to be present in the at least one vacuum lumen. The at least one vacuum lumen can be constructed and arranged to cause tissue to tend toward the at least one fluid delivery element. The at least one vacuum lumen can comprise multiple vacuum lumens, and the at least one control can comprise multiple controls constructed and arranged to independently initiate a vacuum to be present in each of the multiple vacuum lumens. The at least one control can be further constructed and arranged to apply a positive pressure to the at least one vacuum lumen. The at least one control can comprise a first control for initiating the vacuum and a second control for initiating the positive pressure. The positive pressure can be constructed and arranged to flush material from the at least one vacuum lumen. The at least one vacuum lumen can comprise multiple vacuum lumens. The at least one control can comprise multiple controls constructed and arranged to independently flush the multiple vacuum lumens. The injectate delivery device can further comprise at least one tissue capture port fluidly attached to the at least one vacuum lumen, and the at least one tissue capture port can be constructed and arranged to cause tissue to tend toward the at least one fluid delivery element when the vacuum is applied, and the positive pressure can be constructed and arranged to cause the tissue to tend away from the at least one fluid delivery element.

In some embodiments, the at least one control comprises a control biased in an off state. The at least one control can comprise a spring-biased control mechanism. The at least one control can be constructed and arranged to advance the at least one fluid delivery element. The at least one control can be constructed and arranged to initiate delivery of injectate through the at least one fluid delivery element into tissue. The at least one control can be constructed and arranged to activate a vacuum.

In some embodiments, the injectate delivery device further comprises a sensor. The sensor can comprise multiple sensors. The sensor can comprise a sensor selected from the group consisting of: pressure sensor; temperature sensor; impedance sensor; pH sensor; flow sensor; ultrasonic sensor; optical sensor; magnetic sensor; hall effect sensor; osmolarity sensor; strain gauge; gas bubble sensor; and combinations thereof. The injectate delivered by the at least one fluid delivery element can comprise a dye, and the sensor can comprise a camera constructed and arranged to image the tissue being expanded and produce a signal correlating to the amount of tissue expansion based on the amount of dye present in the expanded tissue. The dye can comprise a material selected from the group consisting of: visible dye; ultrasonically reflective material; radiopaque dye; and combinations thereof. The injectate delivered by the at least one fluid delivery element can comprise a temperature different than body temperature, and the sensor can comprise a temperature sensor constructed and arranged to measure the temperature proximate the tissue being expanded and produce a signal correlating to the amount of tissue expansion based on the difference between the measured temperature and body temperature. The injectate delivered by the at least one fluid delivery element can comprises a pH different than the pH of the target tissue, and the sensor can comprise a pH sensor constructed and arranged to measure the pH proximate the tissue being expanded and produce a signal correlating to the amount of tissue expansion based on a change in the measured pH. The sensor can comprise an ultrasound transducer directed at the tissue being expanded, and the sensor can be constructed and arranged to produce a signal correlating to the amount of tissue expansion based on an analysis of an image of the expanding tissue produced by the ultrasound transducer. The sensor can be positioned in fluid communication with at least one of the at least one fluid delivery tube or the at least one fluid delivery element. The at least one fluid delivery element can comprise multiple fluid delivery elements attached to an expandable element, and the sensor can be in fluid communication with the expandable element. The injectate delivery device can further comprise at least one vacuum lumen, and the sensor can be positioned in fluid communication with the at least one vacuum lumen. The sensor can be constructed and arranged to detect an occlusion. The sensor can be constructed and arranged to detect an occlusion within the at least one fluid delivery lumen. The at least one fluid delivery lumen can comprise multiple fluid delivery lumens and the sensor can be constructed and arranged to detect an occlusion in two or more of the fluid delivery lumens independently from one another. The injectate delivery device can further comprise at least one vacuum lumen, and the sensor can be constructed and arranged to detect an occlusion within the at least one vacuum lumen. The at least one vacuum lumen can comprise multiple vacuum lumens, and the sensor can comprise multiple sensors constructed and arranged to detect an occlusion in two or more of the vacuum lumens independently. The sensor can be constructed and arranged to detect presence of a vacuum. The injectate delivery device can further comprise at least one tissue capture port, and the sensor can be constructed and arranged to detect a vacuum present proximate the at least one tissue capture port. The at least one fluid delivery element can comprise multiple fluid delivery elements attached to an expandable element, and the sensor can be constructed and arranged to detect radial expansion of the expandable element. The expandable element can comprise a balloon. The sensor can be constructed and arranged to detect the delivery of injectate into the tissue. The sensor can be constructed and arranged to detect when the at least one fluid delivery element is in an advanced position. The injectate delivery device can further comprise at least one advanceable tube, and the sensor can be constructed and arranged to detect when the at least one advanceable tube is in an advanced position. The at least one advanceable tube can comprise the at least one fluid delivery tube. The at least one fluid delivery element can comprise multiple fluid delivery elements attached to an expandable balloon, and the sensor can be constructed and arranged to measure the balloon pressure. The injectate delivery device can be constructed and arranged to stop injectate infusion when the balloon pressure reaches or exceeds a pressure threshold. The injectate delivery device can be constructed and arranged to stop injectate infusion when the balloon pressure is below a pressure threshold. The injectate delivery device can be constructed and arranged to expand the balloon until it reaches a pressure threshold. The pressure threshold can be at least 0.4 psi, or at least 0.8 psi. The injectate delivery device can be constructed and arranged to maintain the balloon at a pre-determined pressure level for a pre-determined time period prior to beginning delivery of injectate to tissue by the at least one fluid delivery element. The at least one fluid delivery element can be constructed and arranged to be translated to an advanced position and the sensor can be constructed and arranged to detect the at least one fluid delivery element in the advanced position. The injectate delivery device can further comprise a second sensor configured to produce a signal corresponding to flow through the fluid delivery element, and the injectate delivery device can be constructed and arranged to enter an alarm state or other alert state when the at least one fluid delivery element is advanced and the flow through the fluid delivery element is below a threshold. The injectate delivery device can further comprise an expandable element attached to the at least one fluid delivery element and a second sensor configured to produce a signal corresponding to expansion of the expandable element, and the injectate delivery device can be constructed and arranged to enter an alert state when the at least one fluid delivery element is advanced and the diameter of the expandable element is below a threshold. The injectate delivery device can further comprise a vacuum location and a second sensor configured to produce a signal corresponding to the vacuum level at the vacuum location, and the injectate delivery device can be constructed and arranged to enter an alert state when the at least one fluid delivery element is advanced and the vacuum level is below a threshold. The injectate delivery device can comprise: a vacuum location; a vacuum sensor configured to produce a signal correlating to the vacuum level in the vacuum location; a balloon attached to the at least one fluid delivery element; and a balloon pressure sensor configured to produce a signal correlating to the pressure in the balloon. The injectate delivery device can be configured to enter an alert state when the balloon pressure is below a first threshold and the vacuum level is above a second threshold. The expandable assembly can comprise a balloon, the sensor can comprise a first sensor configured to monitor pressure within the balloon and a second sensor configured to monitor flow through the at least one fluid delivery element, and the injectate delivery device can be constructed and arranged to enter an alert state when the pressure in the balloon is above a threshold and injectate is flowing (e.g. at a sufficient flow rate) through the at least one fluid delivery element. The expandable assembly can comprise a balloon, the sensor can comprise a first sensor configured to monitor pressure within the balloon and a second sensor configured to monitor flow through the at least one fluid delivery element, and the injectate delivery device can be constructed and arranged to enter an alert state when the pressure in the balloon is below a threshold and injectate is flowing (e.g. at a sufficient flow rate) through the at least one fluid delivery element.

In some embodiments, the injectate delivery device further comprises a transducer. The transducer can comprise an element selected from the group consisting of: heating element; audio transducer; vibrational transducer; light transducer; magnetic transducer; visual transducer; ultrasound sensor; camera; and combinations thereof. The injectate delivery device can further comprise a handle, and the handle can comprise the transducer. The injectate delivery device can comprise a shaft, and the shaft can comprise the transducer. The transducer can be constructed and arranged to provide an alarm or other alert signal. The alert signal can comprise at least one of an audible alert or a tactile alert. The injectate delivery device can further comprise at least one tissue capture port, and the injectate delivery device can be constructed and arranged to activate the alert signal when vacuum is applied to the tissue capture port. The injectate delivery device can further comprise an expandable element, and the injectate delivery device can be constructed and arranged to activate the alert signal when the expandable element is radially expanded. The injectate delivery device can be constructed and arranged to activate the alert signal when injectate is being delivered into tissue. The at least one fluid delivery element can be constructed and arranged to be placed in an advanced position, and the injectate delivery device can be constructed and arranged to activate the alert signal when the at least one fluid delivery element is in the advanced position. The transducer can comprise a pressure regulator. The transducer can comprise a pressure relief valve.

In some embodiments, the injectate delivery device further comprises a tissue capture port surrounding the at least one fluid delivery element. The tissue capture port can comprise an opening, and the opening can comprise a dimension selected from the group consisting of: length of at least 0.1"; length of between 0.14" and 0.20"; length of approximately 0.16"; width of at least 0.4"; width of between 0.05" and 0.08"; width of approximately 0.06"; and combinations thereof. The tissue capture portion can comprise a depth with a dimension selected from the group consisting of: at least 0.05"; between 0.06" and 0.10"; approximately 0.08"; and combinations thereof. The tissue capture port can be in fluid communication within a vacuum source such that tissue enters the tissue capture port when vacuum is applied. The tissue capture port can be constructed and arranged such that tissue exits the port when positive pressure is applied. The at least one fluid delivery element can be constructed and arranged to travel from a retracted position to an advanced and remain within the tissue capture port for the length of travel. The injectate delivery device can further comprise a second tissue capture port surrounding a second fluid delivery element. The tissue capture port can comprise at least a radiopaque portion.

The injectate delivery device can further comprise a handle including a user interface, wherein the user interface comprises the at least one control. The handle user interface can comprise a user output component selected from the group consisting of: screen; touchscreen; light; tactile transducer; audio transducer; and combinations thereof. The handle user interface can comprise a user input component selected from the group consisting of: touchscreen; keyboard; mouse; joystick; switch; and combinations thereof. The handle user interface can be constructed and arranged to display information selected from the group consisting of: fluid delivery element position; vacuum status; occlusion status; expandable element status; volume of injection from the at least one fluid delivery element; total injected volume of injectate; pressure of injection; catheter position, such as catheter position relative to the papilla; number of completed injections; and combinations thereof. The handle user interface can be constructed and arranged to display a visual image. The visual image can comprise an image of the gastrointestinal lumen. The visual image can comprise an image provided by an endoscope. The handle user interface can be configured to control a second device. The second device can comprise a device selected from the group consisting of: endoscope; fluid delivery device; energy delivery device; visualization device; and combinations thereof.

In some embodiments, the injectate delivery device further comprises a handle with a first portion constructed and arranged for use in a plurality of medical procedures, and a second portion constructed and arranged for fewer uses than the first. The second portion can be constructed and arranged for use in a single clinical procedure. The first portion can comprise a component selected from the group consisting of: printed circuit board; transducer; audible transducer; tactile transducer; light; LED; sensor; magnetic sensor; hall effect sensor; and combinations thereof.

In some embodiments, the injectate delivery device further comprises a handle comprising an attachment element constructed and arranged to removably attach to an endoscope. The attachment element can be constructed and arranged to removably attach to a biopsy port of an endoscope. The attachment element can comprise a component selected from the group consisting of: clip; clamp; strap; electromagnetic coupler such as a solenoid-based clamp; adhesive strip; and combinations thereof. The injectate delivery device can be constructed and arranged to operably connect to an endoscope and to remotely control the endoscope. The injectate delivery device can further comprise a handle and a control positioned on at least one of the handle or the attachment element, and the injectate delivery device can be constructed and arranged to remotely control the endoscope via the control. The injectate delivery device can be constructed and arranged to control a function of the endoscope selected from the group consisting of: activating a camera; modifying flow of insufflation fluid or flushing fluid; advancing or retracting a shaft; delivering energy; and combinations thereof. The injectate delivery device can be constructed and arranged to control a component of the endoscope selected from the group consisting of: suction valve; vent hole; air or water valve; channel opening such as a biopsy channel opening; suction connector; air supply connector; water supply connector; and combinations thereof.

In some embodiments, the injectate delivery device further comprises at least one tissue capture port including an opening, and the at least one fluid delivery element can comprise a needle oriented toward the opening such that when vacuum is applied to the tissue capture port, tissue is drawn into the tissue capture port through the opening and is penetrated by the needle.

In some embodiments, the injectate delivery device further comprises at least one tissue capture port including a translatable carriage positioned slidingly therein. The at least one fluid delivery element can comprise a needle, and translation of the carriage proximally causes tissue captured within the carriage to be penetrated by the needle. The injectate delivery device can be constructed and arranged to capture tissue within the at least one tissue capture port through application of vacuum to the tissue capture port. The carriage can be constructed and arranged to translate proximate by application of vacuum to the at least one tissue capture port. The carriage can be constructed and arranged to translate distally by removal of vacuum from the at least one tissue capture port. The carriage can be constructed and arranged to translate distally by application of positive pressure to the at least one tissue capture port. The injectate delivery device can further comprise a biasing spring attached to the carriage. The biasing spring can be constructed and arranged to bias the carriage in a distal position. The injectate delivery device can further comprise a control rod attached to the carriage, and the carriage can be translated proximally by retraction of the control rod. The carriage can be translated distally by advancement of the control rod.

In some embodiments, the at least one fluid delivery element comprises one or more elements selected from the group consisting of: needle; fluid jet; iontophoretic element; a porous element; and combinations thereof.

In some embodiments, the at least one fluid delivery element comprises one or more needles. The at least one fluid delivery element can comprise a needle with a diameter greater than 30 ga. The at least one fluid delivery element can comprise a needle with a diameter greater than 27 ga. The at least one fluid delivery element can comprise a curved needle.

In some embodiments, the at least one fluid delivery element comprises multiple fluid delivery elements. The multiple fluid delivery elements can comprise multiple elements disposed in a circumferential array. The multiple fluid delivery elements can comprise at least three fluid delivery elements. The multiple fluid delivery elements can comprise three fluid delivery elements separated by approximately 120° along a circumference.

In some embodiments, the injectate delivery device further comprises a radially expandable element, and the at least one fluid delivery element can comprise multiple fluid delivery elements positioned on the radially expandable element. The radially expandable element can comprise an element selected from the group consisting of: balloon; cage; radially deployable arm; and combinations thereof. The radially expandable element can comprise a balloon. The radially expandable element can be constructed and arranged to apply a force to luminal tissue at a pressure of no more than 2.0 psi. The radially expandable element can be constructed and arranged to apply a force to luminal tissue at a pressure no more than 1.2 psi. The radially expandable element can be constructed and arranged to contact luminal tissue at a pressure of at least 0.6 psi as the injectate is delivered to the target tissue. The radially expandable element can be constructed and arranged to expand to a target diameter of between 20 mm and 35 mm. The radially expandable element can be constructed and arranged to expand to a target diameter of between 20 mm and 27.5 mm. The radially expandable element can be constructed and arranged to expand to a target diameter in less than 60 seconds. The radially expandable element can be constructed and arranged to expand to a target diameter in less than 30 seconds. The radially expandable element can be constructed and arranged to expand to a target diameter in less than 15 seconds. The expandable element can be constructed and arranged to expand with injectate maintained at a pressure of approximately 0.7 psi until a target diameter is reached. The radially expandable element can be constructed and arranged to expand to a target diameter that is less than the diameter of the lumen in which it is positioned. The injectate delivery device can be constructed and arranged to deliver a vacuum that tends tissue toward the at least one fluid delivery element. The radially expandable element can comprise a proximal portion attached to multiple fluid delivery tubes, and the multiple fluid delivery tubes can define an opening positioned proximate the radially expandable element proximal portion and sized to receive the distal end of an elongate device positioned within 9 cm of the radially expandable element proximal portion. The opening can be sized to receive the distal end of an elongate device positioned within 1.5 cm, within 2.0 cm or within 3.0 cm of the radially expandable element proximal portion. The elongate device can comprise an endoscope or other elongate visualization device. The injectate delivery device can comprise a guidewire lumen positioned such that an inserted guidewire does not pass through the proximal end of the radially expandable element. The multiple fluid delivery tubes can each comprise a distal portion, and the distal portions can be arranged to receive the elongate device.

In some embodiments, the injectate delivery device further comprises the injectate delivered by the at least one fluid delivery element to the target tissue. The injectate can comprise a material selected from the group consisting of: water; saline; fluid with a dye such as a visible dye such as indigo carmine; methylene blue; India ink; SPOT™ dye; a gel; a hydrogel; a protein hydrogel; a fluid containing a visualizable media such as a media visualizable under X-ray; ultrasound and/or magnetic resonance imaging; and combinations thereof. The injectate can be constructed and arranged to remain in place in tissue for an extended period of time. The injectate can be constructed and arranged to remain in place for a time period selected from the group consisting of: at least one day; at least one week; at least one month; at least 3 months; at least 6 months; or combinations thereof. The injectate can comprise a material selected from the group consisting of: biopolymer such as ethylene vinyl alcohol; adhesive such as cyanoacrylate; and combinations thereof.

In some embodiments, the injectate delivery device further comprises a mechanical stop constructed and arranged to limit the advancement of the at least one fluid delivery element.

In some embodiments, the injectate delivery device comprises a distal end and a bulbous tip positioned on the distal end. The bulbous tip can comprise a diameter between approximately 2 mm and 9 mm. The bulbous tip can comprise a diameter between approximately 4 mm and 6 mm. The ball tip can comprise at least a radiopaque portion.

In some embodiments, the at least one fluid delivery tube is constructed and arranged to avoid radial expansion. The at least one fluid delivery tube can comprise a braided tube. The at least one fluid delivery tube can comprise a braided polyimide tube.

In some embodiments, the injectate delivery device is constructed and arranged to limit the force applied to a component selected from the group consisting of: the at least one fluid delivery tube; the at least one fluid delivery element; and combinations thereof.

In some embodiments, the at least one fluid delivery tube comprises a proximal portion, and the injectate delivery device further comprises a compression element operably attached to the at least one fluid delivery tube proximal portion. The compression element can comprise a spring. The compression element can be constructed and arranged to limit the force applied to the at least one fluid delivery tube. The injectate delivery device can be constructed and arranged to prevent full compression of the compression element.

In some embodiments, the injectate delivery device further comprises an elongate shaft with a proximal end and a distal portion. The elongate shaft can comprise multiple shafts. The multiple shafts can each comprise a proximal portion, and the multiple shafts' proximal portions can diverge. The multiple shafts can each comprise a distal portion, and the multiple shafts' distal portions can diverge. The multiple shafts can comprise a helical arrangement along at least a portion of the elongate shaft. The helical arrangement can be positioned proximate the at least one fluid delivery element. The helical arrangement can comprise uniform pitch. The helical arrangement can comprise non-uniform pitch. The helical arrangement can comprise between 360° and 1440° of twist. The helical arrangement can comprise approximately 540° of twist. The injectate delivery device can further comprise an expandable assembly, and a first shaft can comprise an inflation lumen constructed and arranged to deliver injectate to the expandable assembly, and a second shaft can surround the at least one fluid delivery tube. The at least one fluid delivery tube can comprise three fluid delivery tubes, and the multiple shafts can comprise three shafts, each surrounding a fluid delivery tube. The at least one fluid delivery element can comprise three fluid delivery elements each fluidly attached to a separate fluid delivery tube, and the three fluid delivery elements can be separated by approximately 120°. The expandable assembly can be constructed and arranged to expand to a diameter selected from the group consisting of: at least 20 mm; between 25 mm and 36 mm; between 28 mm and 36 mm; approximately 32 mm; and combinations thereof. The at least one fluid delivery tube can comprise the elongate shaft and the at least one fluid delivery lumen can comprise a first lumen of the shaft. The at least one fluid delivery lumen can comprise a second lumen and a third lumen of the shaft. The at least one fluid delivery tube can comprise a first fluid delivery tube slidingly received by the elongate shaft. The at least one fluid delivery tube can further comprise a second fluid delivery tube and a third fluid delivery tube each slidingly received by the elongate shaft. The elongate shaft can comprise a first vacuum lumen. The elongate shaft can further comprise a second vacuum lumen and a third vacuum lumen. The first, second and third vacuum lumens can travel from the elongate shaft proximal end to the distal portion. The elongate shaft can comprise a guidewire lumen. The guidewire lumen can comprise a diameter between approximately 0.040" to 0.050". The guidewire lumen can be positioned about a central axis of the shaft along a majority of the length of the shaft.

In some embodiments, the injectate delivery device further comprises a functional element. The functional element can comprise an element selected from the group consisting of: a sensor; a transducer; an ablation element such as one or more electrodes configured to deliver electrical energy such as radiofrequency (RF) energy; a fluid delivery element such as a needle, a fluid jet, a permeable membrane and/or an exit port; a heating element; a cooling element; and combinations thereof. The functional element can be positioned proximate a component selected from the group consisting of: the at least one fluid delivery tube; the at least one fluid delivery element; and combinations thereof.

In some embodiments, the injectate delivery device further comprises a steering mechanism positioned within the shaft.

In some embodiments, the injectate delivery device further comprises an elongate shaft and a camera positioned within the elongate shaft.

In some embodiments, the injectate delivery device is constructed and arranged to deliver insufflation fluid.

In some embodiments, the expanded tissue comprises a tissue layer of the gastrointestinal tract. The expanded tissue layer can comprise one or more layers of submucosal tissue. The expanded tissue layer can comprise one or more layers of duodenal submucosal tissue.

In some embodiments, the injectate delivery device is constructed and arranged to perform a near full circumferential expansion of luminal wall tissue.

In some embodiments, the injectate delivery device is constructed and arranged to create a therapeutic restriction in the gastrointestinal tract.

In some embodiments, the injectate delivery device is constructed and arranged to deliver injectate to submucosal vessels. The injectate delivery device can be constructed and arranged to deliver injectate to submucosal vessels to treat mucosal tissue.

In some embodiments, the injectate delivery device is constructed and arranged to cause a reduction in cross sectional area of a gastrointestinal lumen. The reduction in cross sectional area can comprise a reduction of between 80% and 85% of the pre-expansion cross sectional area. The reduction in cross sectional area can comprise reducing a pre-expansion cross sectional diameter of approximately 25 mm to 28 mm by approximately between 2 mm and 4 mm.

According to another aspect of the inventive concepts, a system comprises an injectate delivery device as described hereabove and a component selected from the group consisting of: an endoscope; injectate for delivery through the at least one fluid delivery element; an ablation catheter comprising a treatment element for treating target tissue proximate the expanded tissue layer; a sizing device constructed and arranged to provide lumen diameter information; a guidewire; and combinations thereof.

In some embodiments, the system is constructed and arranged to treat a disease or disorder selected from the group consisting of: diabetes; obesity or otherwise being overweight; hypercholesterolemia; exercise intolerance; psoriasis; hypertension; metabolic syndrome; and combinations thereof.

In some embodiments, the system is constructed and arranged to ablate tissue distal to the ampulla of Vater. The system can be constructed and arranged to ablate at least 50% of the duodenal mucosal distal to the ampulla of Vater.

According at another aspect of the inventive concepts, a method comprises selecting an injectate delivery device as describe hereabove, and delivering injectate through the at least one fluid delivery element into target tissue to expand tissue proximate the target tissue.

In some embodiments, the method is constructed and arranged to treat a disease or disorder selected from the group consisting of: diabetes; obesity or otherwise being overweight; hypercholesterolemia; exercise intolerance; psoriasis; hypertension; metabolic syndrome; and combinations thereof.

In some embodiments, the expanded tissue comprises a cumulative axial length of duodenal mucosa selected from the group consisting of: at least 5 cm of axial length; at least 10 cm of axial length; and at least 15 cm of axial length.

In some embodiments, a first axial length of approximately between 4 cm and 5 cm is expanded, and subsequently at least 3 cm of the first axial length is ablated.

In some embodiments, the method is constructed and arranged to ablate tissue distal to the ampulla of Vater. The method can be constructed and arranged to ablate at least 50% of the duodenal mucosal distal to the ampulla of Vater.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIG. 1 is a side view of an injectate delivery system comprising a fluid delivery assembly and an injectate delivery device, wherein the injectate delivery device includes a proximal handle with operator activated controls and a distal array of fluid delivery elements, consistent with the present inventive concepts.

FIG. 1A is a magnified side sectional view of a tissue port of the injectate delivery device of FIG. 1, consistent with the present inventive concepts.

FIG. 2A is a side view of a force limiting assembly, consistent with the present inventive concepts.

FIG. 2B is a side sectional view of a segment of shaft of an injectate delivery device oriented in a curved geometry, consistent with the present inventive concepts.

FIG. 2C is an end sectional view of a portion of a shaft of an injectate delivery device, consistent with the present inventive concepts.

FIGS. 4A-4D are a series of side sectional anatomical views of the distal portion of an injectate delivery device delivering injectate into tissue that has been captured by a tissue port, consistent with the present inventive concepts.

FIGS. 11A and 11B are side sectional anatomical views of the distal portion of an injectate delivery device prior to and after translation of a tissue port carriage via retraction of a control rod, consistent with the present inventive concepts.

DETAILED DESCRIPTION OF THE DRAWINGS

Figure 3:
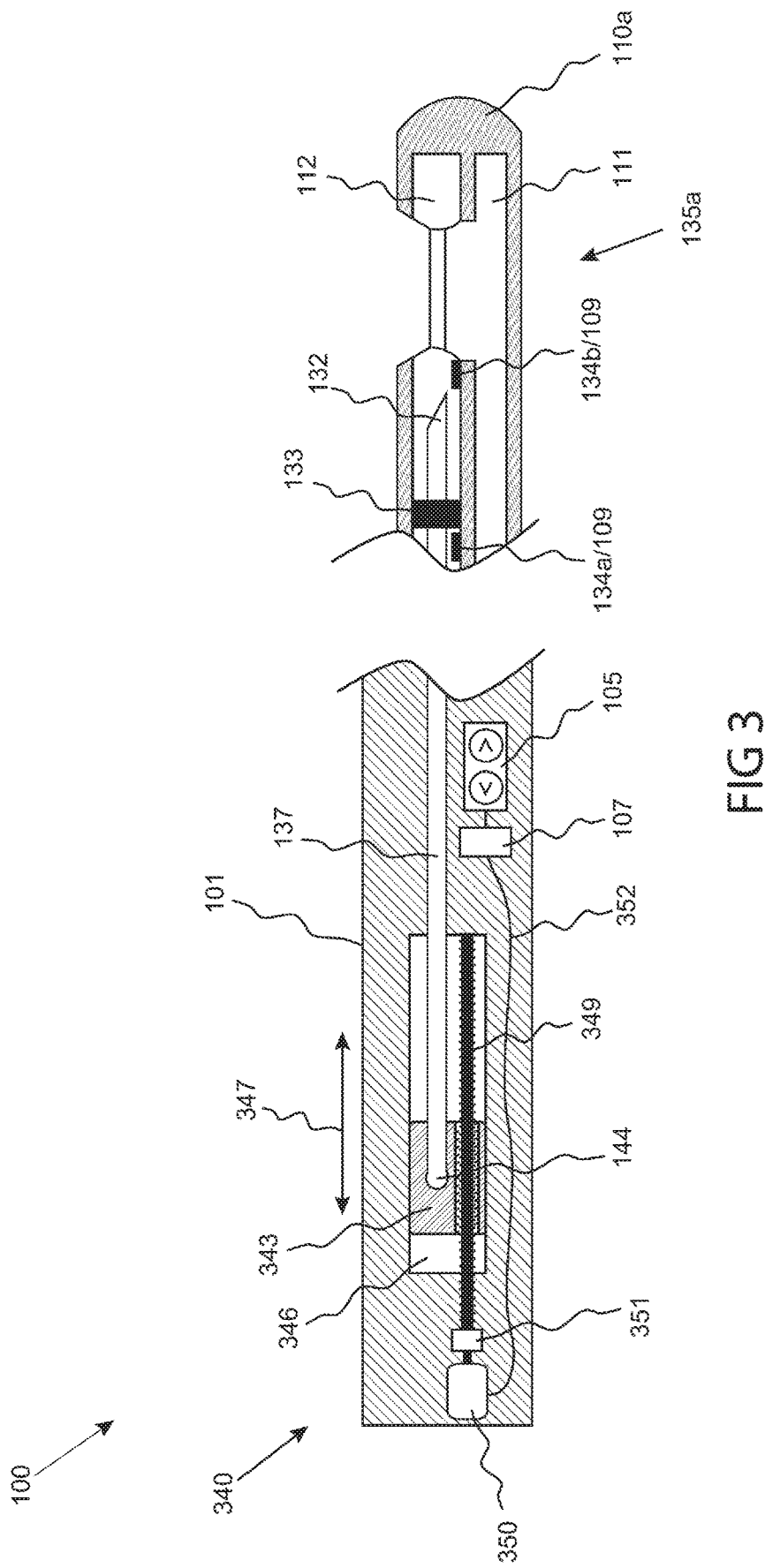
FIG. 3 is a side sectional view and a magnified side sectional view of the proximal and distal portions, respectively, of an injectate delivery device, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove. As used herein, the term "vacuum level" refers to a measure of a vacuum wherein the lower the pressure, the greater the vacuum level.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

It is an object of the present inventive concepts to provide devices, systems, and methods to safely and effectively expand an area of tissue, such as one or more layers of a portion of tubular or solid tissue, such as tissue of an organ or tissue of the gastrointestinal (GI) tract of a patient. The expanded tissue can comprise one or more submucosal layers of tissue, such as one or more full or partial circumferential submucosal layers of one or more segments (e.g. one or more axial segments) of the duodenum. The devices and systems of the present inventive concepts include one or more fluid delivery elements, such as needles or water jets configured to deliver one or more fluids to target tissue, to expand the target tissue and/or tissue proximate the target tissue (hereinafter "target tissue"). Needles can comprise hollow or partially hollow needles, such as needles with one or more openings at the distal end and/or at a side wall location. One or more visualization assemblies (e.g. an endoscope camera or other camera, an ultrasound imager, and the like) can be included, such as to allow an operator to visualize or otherwise assess the tissue expansion or other injectate delivery procedure (e.g. when the delivered fluid includes a dye or is otherwise visible). One or more tissue manipulation assemblies can be included, such as to apply a force to enhance or otherwise modify the injectate delivery.

In some embodiments, a vacuum or other negative pressure can be used to manipulate tissue and/or to maintain proximity between a portion of an injectate delivery device or assembly, and tissue. This vacuum or other negative pressure can comprise a pressure below another pressure, such as a pressure below the pressure of the environment surrounding the patient, hereinafter referred to as a "vacuum" or "vacuum pressure". The vacuum can be provided by one or more vacuum sources, such as via one or more operator adjustable vacuum sources.

In some embodiments, the injectate delivery is performed prior to treatment of tissue, such as a tissue treatment comprising an ablation of a target volume of tissue. The devices and systems of the present invention can further include one or more ablation devices, such as ablation devices configured to treat a layer of tissue proximate (e.g. above or below) a previously expanded tissue layer, such as to prevent damage to one or more tissue layers below or above the expanded tissue layer. In these embodiments, the expanded tissue layer acts as a safety volume of tissue, reducing the specificity of the ablation required and/or the need to protect the underlying tissue from damage.

The injectate delivery systems of the present inventive concepts can include an injectate delivery device constructed and arranged for insertion into a patient, as well as a fluid delivery assembly operably (e.g. fluidly and/or electrically) attached to the injectate delivery device. The injectate delivery device can include one or more fluid delivery elements. The handle of the injectate delivery device can comprise one or more controls configured to control the injectate delivery device and/or the fluid delivery assembly, such as via a wired or wireless connection. The injectate delivery system can further include a tissue ablation device, such as a hot fluid or radiofrequency (RF) ablation device.

Referring now to FIG. 1, a side view of an injectate delivery system comprising a fluid delivery assembly and an injectate delivery device is illustrated, wherein the injectate delivery device includes a proximal handle with operator activated controls and a distal array of fluid delivery elements, consistent with the present inventive concepts. System 10 comprises an injectate delivery device, device 100, and an assembly for delivering one or more fluids, at positive or negative pressure, to device 100, fluid delivery assembly 200. Device 100 can be constructed and arranged for insertion into the body of a patient, such as through a channel of an endoscope (e.g. an endoscope inserted through the mouth of a patient and accessing a GI location such as the duodenum), through the channel of a laparoscopic port (e.g. a laparoscopic port accessing the GI tract or an organ of the patient), and/or over a guidewire (e.g. over a guidewire placed outside of but parallel to an endoscope accessing a GI location). Body-contacting and/or body-inserted components of device 100 can be constructed of one or more biocompatible materials. System 10 and/or device 100 can be constructed and arranged to deliver fluid to tissue to perform one or more functions. In some embodiments, system 10 and/or device 100 is constructed and arranged to deliver injectate to expand one or more layers of tissue prior to a tissue treatment procedure. For example, submucosal tissue of the duodenum or other GI tract location can be expanded prior to ablating neighboring mucosal tissue, such as is described hereinbelow in reference to FIG. 7. Alternatively or additionally, system 10 and/or device 100 can be constructed and arranged to deliver fluid to submucosal blood vessels to damage, denature or otherwise treat mucosal tissue to cause a therapeutic benefit. Alternatively or additionally, system 10 and/or device 100 can be constructed and arranged to create a therapeutic restriction, such as a restriction configured to treat a disease or disorder such as obesity, such as is described in applicant's co-pending International Patent Application Serial Number PCT/US2014/066829, entitled "Systems, Devices and Methods for the Creation of a Therapeutic Restriction in the Gastrointestinal Tract", filed Nov. 21, 2014, the entire content of which is incorporated herein by reference in its entirety.

Device 100 includes shaft 110, which can comprise a single shaft including one or more lumens, or multiple shafts (e.g. each including one or more lumens) whose external walls can be attached along at least a portion of the length of shaft 110. At the proximal end of shaft 110 is handle 101. On the distal end or on a distal portion of shaft 110 is expandable assembly 130. In the embodiment of FIG. 1, shaft 110 comprises 4 shafts, shafts 110a, 110b, 110c and 110d, whose proximal portions diverge from each other at a location proximate handle 101 as shown. The distal portions of shaft 110a, 110b, 110c and 110d can also diverge from each other. Shafts 110a-c of FIG. 1 extend in a curved, diverging arrangement to attach to the surface of expandable assembly 130, such as in an arrangement with equal spacing (e.g. 120° apart for three shafts 110a-c). Shaft 110d diverges from shafts 110a-c but continues in a relatively straight direction attaching to the proximal end of expandable assembly 130 (distal portion of shaft 110d not shown as it is hidden by the distal portion of shaft 110b.

In some embodiments, system 10 and/or device 100 are of similar construction and arrangement to the system and device of applicant's co-pending U.S. patent application Ser. No. 14/515,324, entitled "Tissue Expansion Devices, Systems and Methods", filed Oct. 15, 2014, the entire content of which is incorporated herein by reference in its entirety. In some embodiments, system 10 and/or device 100 are of similar construction and arrangement to system 10 and/or device 100 described hereinbelow in reference to FIG. 7.

Expandable assembly 130 comprises an expandable element 131, such as a balloon, deployable cage, or set of radially deployable arms. Expandable assembly 130 can comprise one or more tissue capture ports, such as the three ports 135a, 135b and 135c (singly or collectively port 135) shown in FIG. 1 with relatively equivalent (e.g. 120°) spacing. Expandable assembly 130 can comprise a single tissue capture port 135, or it can comprise between two and ten tissue capture ports 135. One or more portions of each port 135 can comprise a radiopaque portion. Shaft 110 can further comprises a distal segment, shaft 110e, attached to a distal portion of expandable assembly 130 as shown. An atraumatic tip, bulbous tip 115, can be mounted to the distal end and/or a distal portion of shaft 110e. In some embodiments, bulbous tip 115 comprises a diameter between 4 mm and 9 mm, such as a diameter between 4 mm and 6 mm. In some embodiments, bulbous tip 115 comprises at least a radiopaque portion. Bulbous tip 115 can comprise a passageway, guidewire lumen 116, passing from a proximal to distal portion of bulbous tip 115, such that device 100 can be advanced over a guidewire passing through lumen 116. In some embodiments, lumen 116 comprises a diameter of approximately 0.040" to 0.050" (e.g. to accommodate a 0.035" or 0.038" diameter guidewire). System 10 can include a guidewire for insertion through lumen 116 and over-the-wire advancement of device 100, such as a guidewire selected from the group consisting of: an 0.35" guidewire; an 0.038" guidewire; a guidewire relatively similar to an Amplatz Super Stiff guidewire; a guidewire relatively similar to a Wallstent Super Stiff guidewire; a guidewire relatively similar to a Dreamwire Stiff Shaft guidewire; and combinations of these. In some embodiments, guidewire lumen 116 is parallel to and off center from the central axis of the distal portion of shaft 110e. In other embodiments, guidewire lumen 116 is not parallel to the central axis of the distal portion of shaft 110e. In some embodiments, guidewire lumen 116 passes through one or more portions of shaft 110, such as a guidewire lumen 116 which is in the relative center of shaft 110 and/or travels proximally to exit a port positioned on handle 101.

Referring additionally to FIG. 1A, a magnified view of tissue capture port 135c of expandable assembly 130 is illustrated, consistent with the present inventive concepts. Port 135c can be positioned in and/or on a distal portion of shaft 110c as shown. The distal portion of shaft 110c can be attached to expandable element 131, such as via adhesive or other attachment element (e.g. a flexible attachment element). Shaft 110c can comprise one or more lumens, such as lumen 111 constructed and arranged for attachment to a vacuum source, and lumen 112 constructed and arranged to slidingly receive a fluid delivery tube (e.g. fluid delivery tube 137 described herebelow). Lumens 111 and 112 can each comprise a cross sectional profile as described herebelow in reference to FIG. 2C.

Port 135c comprises an opening 136 in the wall of shaft 110c, which is in fluid communication with vacuum lumen 111. An advanceable needle or other fluid delivery element, fluid delivery element 132, is constructed and arranged to be advanced into opening 136 as described herebelow in reference to FIGS. 4A-4D. Fluid delivery element 132 can comprise a fluid delivery element selected from the group consisting of: needle; water jet; iontophoretic fluid delivery element; and combinations of these. In some embodiments, one or more fluid delivery elements 132 comprise a needle, such as a curved or relatively straight needle with a diameter greater than 30 ga, or greater than 27 ga. In some embodiments, fluid delivery element 132 can remain stationary while tissue is brought toward fluid delivery element 132, such as is described herebelow in reference to FIGS. 9, 9A, 10A, 10B, 11A and 11C.

Fluid delivery element 132 includes lumen 138 which is fluidly attached to fluid delivery tube 137. In some embodiments, fluid delivery element 132 comprises a needle with an outer diameter of approximately 0.016" and lumen 138 comprises an outer diameter of approximately 0.008". In some embodiments, fluid delivery tube 137 comprises a polyimide tube, such as a tube with an outer diameter of approximately 0.022" and/or an inner diameter of approximately 0.016". Fluid delivery tube 137 is slidingly received by lumen 111 of shaft 110c, and travels proximally to handle 101. Fluid delivery element 132 and fluid delivery tube 137 can be fluidly attached at any location within shaft 110c or handle 101. Fluid delivery tubes 137 can be constructed and arranged to avoid or at least minimize radial expansion, such as when fluid delivery tube 137 comprises a braided tube such as a braided polyimide tube.

Fluid delivery element 132 and/or fluid delivery tube 137 can be surrounded by collar 133, as shown. Lumen 112 comprises two projections which extend into lumen 112, proximal stop 134a and distal stop 134b. Device 100 is constructed and arranged such that fluid delivery element 132 and the distal end of fluid delivery tube 137 can advance distally until collar 133 contacts distal stop 134b, and each can retract proximally until collar 133 contacts proximal stop 134a.

In some embodiments, tissue capture ports 135a and/or 135b can be of similar construction and arrangement and/or include similar components to tissue capture port 135c as described hereabove, such as to include an opening 136 which is fluidly attached to a corresponding vacuum lumen 111 and can be constructed and arranged to receive a corresponding fluid delivery element 132 whose travel is limited by contact of a collar 133 with a mechanical stop 134a and/or 134b.

In some embodiments, one or more of tissue capture ports 135a-c comprise an opening 136 with a length of at least 0.1", such as a length between 0.14" and 0.20", such as a length of approximately 0.16". In some embodiments, one or more tissue capture ports 135a-c comprise an opening with a width of at least 0.04", such as a width between 0.05" and 0.08", such as a width of approximately 0.06". In some embodiments, one or more of tissue capture ports 135a-c comprise a tissue-capture depth of at least 0.05", such as a depth between 0.06" and 0.10", such as a depth of approximately 0.08".

Fluid delivery assembly 200 comprises a controller 210 and one or more fluid transfer mechanisms (e.g. mechanisms to transfer fluid in and/or out of device 100), such as fluid source 220, vacuum source 230 and/or inflation source 240. Controller 210 comprises one or more electronic modules, power sources and/or fluid control components (e.g. valves and/or pumps) configured to initiate, regulate, modify, stop and/or otherwise control fluid source 220, vacuum source 230 and/or inflation source 240. In some embodiments, expandable element 131 of expandable assembly 130 comprises a balloon, and inflation source 240 is constructed and arranged to inflate and/or deflate expandable element 131. In these embodiments, inflation source 240 can comprise a source of fluid such as a liquid (e.g. saline or water) and/or gas (e.g. air) that is fluidly attached to one or more tubes 201 which is in turn fluidly attached to an inflation lumen of shaft 110d, which is fluidly attached to a balloon-based expandable element 131. In some embodiments, shaft 110d comprises an inflation lumen with a cross sectional area of between 1.5 $mm^2$ and 1.9 $mm^2$, such as an inflation lumen with a cross sectional area of approximately 1.7 $mm^2$ when shaft 110d comprises a diameter of approximately 0.090". Controller 210 can operably attach to one or more components of device 100 via cable 202, such that user interface 205 can be used to control one or more components of device 100.

Vacuum source 230 is fluidly attached via one or more tubes 201 to one or more vacuum lumens 111 of shafts 110a, 110b and 110c as described hereabove. Vacuum source 230 can be constructed and arranged to manipulate tissue into one or more of tissue capture ports 135a, 135b and/or 135c (e.g. to cause tissue to tend toward the associated fluid delivery element 132) as described herebelow in reference to FIGS. 4A-4D. In some embodiments, vacuum source 230 provides a vacuum at a pressure between 22 mmHg and 27 mmHg. In some embodiments, vacuum source 230 provides a vacuum to multiple tissue capture ports 135 individually, such as via individual tubes 201 connected to independent lumens 111. Alternatively, multiple tissue capture ports 135 can be fed by a single tube 201 and/or a single lumen 111. In some embodiments, vacuum source 230 is constructed and arranged to apply a reduced vacuum pressure or a positive pressure to one or more tissue capture ports 135, such as to discharge or at least release tissue from within tissue capture port 135 and/or to flush any material from lumen 111 and/or tissue capture port 135. In some embodiments, the positive pressure can be applied (e.g. via a control of user interface 105 and/or 205), to multiple tissue capture ports 135 independently. In some embodiments, a first control of user interface 105 and/or 205 is used to initiate a vacuum and a second, separate control is used to initiate the positive pressure.

Fluid source 220 is fluidly attached via one or more tubes 201 to the lumen of one or more fluid delivery tubes of device 100, such as a lumen of a fluid delivery tube 137 positioned within shaft 110a, 110b and/or 110c, which is fluidly attached to a corresponding fluid delivery element 132. Fluid source 220 is constructed and arranged to deliver fluid or other injectate to one or more fluid delivery elements 132, such as to expand tissue, as described herein. In some embodiments, fluid source 220 provides fluid to multiple fluid delivery elements 132 individually, such as via individual tubes 201 connected to independent fluid delivery tubes 137. Alternatively, multiple fluid delivery elements 132 can be fed by a single tube 201 and/or a single fluid delivery tube 137. In some embodiments, system 10 comprises one or more fluids, injectate 221, to be delivered by fluid source 220 to one or more fluid delivery elements 132 to expand tissue. Injectate 221 can include one or more fluids selected from the group consisting of: water; saline; fluid with a dye such as a visible dye such as indigo carmine; methylene blue; India ink; SPOT™ dye; a gel; a hydrogel; a protein hydrogel; a fluid containing a visualizable media such as a media visualizable under X-ray, ultrasound and/or magnetic resonance imaging; and combinations of these. In some embodiments, injectate 221 can comprise a material constructed and arranged to cause a narrowing or other restriction that results in a therapeutic benefit to the patient, such as is described in applicant's co-pending International Patent Application Serial Number PCT/US2014/066829, entitled "Systems, Devices and Methods for the Creation of a Therapeutic Restriction in the Gastrointestinal Tract", filed Nov. 21, 2014, the entire content of which is incorporated herein by reference in its entirety. In these embodiments, injectate 221 can comprise a material configured to remain in place (e.g. within one or more tissue layers of the GI tract) for an extended period of time, such as at least 1 day, 1 week, 1 month, 3 months or 6 months. Injectate 221 can comprise a biopolymer (e.g. ethylene vinyl alcohol) and/or an adhesive (e.g. cyanoacrylate).

Handle 101 can comprise user interface 105 comprising one or more controls for initiating, modifying, stopping and/or otherwise operating one or more functions of device 100 and/or fluid delivery assembly 200. User interface 105 can include a control, slide 102, constructed and arranged to advance and retract fluid delivery elements 132 into, out of, and/or within the respective tissue capture ports 135. In some embodiments, device 100 is constructed and arranged to advance one or more fluid delivery elements 132 approximately 4 mm. In some embodiments, device 100 is constructed and arranged to advance one or more fluid delivery elements 132 at least 1 mm or at least 2 mm. In some embodiments, device 100 is constructed and arranged to advance one or more fluid delivery elements 132 a distance of no more than 6 mm or no more than 5 mm User interface 105 can include one or more electrical and/or mechanical controls, such as buttons 103 (3 shown in FIG. 1), configured to initiate, regulate modify, stop and/or otherwise control one or more functions of device 100 and/or fluid delivery assembly 200. User interface 105 can include a display 104, such as an LCD display, video display and/or touchscreen configured to provide information to an operator of system 10 and/or receive instructions (e.g. commands) from an operator of system 10. User interface 105 can include numerous user input components, such as a user input component selected from the group consisting of: touchscreen; keyboard; mouse; joystick; switch; and combinations thereof. In some embodiments, display 104 comprises a touchscreen or other user input component configured to allow an operator to initiate, regulate, modify, stop and/or otherwise control one or more functions of device 100 and/or fluid delivery assembly 200. User interface 105 can further comprise one or more user output components, such as a component selected from the group consisting of: display; light such as an LED; tactile transducer such as a vibrational transducer; audio transducer; and combinations of these. In some embodiments, user interface 105 can include a user output component configured to display information selected from the group consisting of: fluid delivery element 132 position (e.g. advanced or retracted); vacuum status (e.g. vacuum level or pressure within lumen 111 and/or tissue capture port 135); occlusion status such as occlusion present in fluid delivery tube 137, lumen 111 and/or tissue capture port 135; expandable element status (e.g. radially compacted, partially expanded, fully expanded or expansion level); volume of fluid injected by one or more individual fluid delivery elements 132; total injected volume of fluid; pressure of injection; catheter position (such as catheter position relative to the papilla); number of completed injections; and combinations thereof. In some embodiments, user interface 105 comprises one or more user output components used to display a visual image, such as an image of the GI lumen, such as an image provided by an endoscope or camera assembly 119 of device 100, described herebelow. In some embodiments, buttons 103 and/or display 104 are used to control fluid source 220, vacuum source 230, inflation source 240 and/or another component of fluid delivery assembly 200.

In some embodiments, buttons 103, display 104 and/or another control of user interface 105 are configured to allow an operator to activate a supply of vacuum provided by vacuum source 230, such as to cause tissue to move or otherwise tend toward a tissue capture port 135 and/or a fluid delivery element 132 as described in detail herebelow. In some embodiments, buttons 103, display 104 and/or another control of user interface 105 are configured to allow an operator to initiate, regulate, modify, stop and/or otherwise control the flow of fluid through one or more fluid delivery elements 132. In some embodiments, buttons 103, display 104 and/or another control of user interface 105 are configured to allow an operator to radially expand and/or radially compact expandable assembly 130. In some embodiments, buttons 103, display 104 and/or another control of user interface 105 are configured to allow an operator to modify a fluid delivery parameter selected from the group consisting of: flow rate of tissue expanding fluid; duration of tissue expanding fluid flow; volume of tissue expanding fluid; temperature of tissue expanding fluid; pressure of tissue expanding fluid; a tissue expanding fluid threshold parameter level (e.g. maximum or minimum flow rate, duration, volume, temperature and/or pressure); type of tissue expanding fluid; and combinations thereof. In some embodiments, buttons 103, display 104 and/or another control of user interface 105 are configured to allow an operator to modify a parameter related to one or more of: fluid source 220 (e.g. fluid flow rate, fluid volume or fluid pressure); vacuum source 230 (e.g. vacuum pressure); and/or inflation source 240 (e.g. inflation flow rate; inflation volume or inflation pressure). In some embodiments, fluid delivery assembly 200 is further constructed and arranged to provide ablation energy to treat tissue, and user interface 105 comprises one or more controls to adjust one or more ablation parameters, such as is described herebelow in reference to FIG. 7.

In some embodiments, one or more controls of user interface 105 is biased to tend towards one state, such as a bias towards a state selected from the group consisting of: on state such as a state in which fluid is flowing and/or vacuum is applied; off state such as a state in which fluid is not flowing and/or vacuum is not applied; advanced state such as a state in which one or more fluid delivery elements are advanced into tissue capture port 135; retracted state such as a state in which one or more fluid delivery elements are retracted from tissue capture port 135; and combinations of these. The bias to one or more controls of user interface 105 can be a mechanical bias (e.g. via a spring as described herebelow in reference to FIG. 2A) or an electronic bias (e.g. via a pre-determined state in memory of electronics module 107). In some embodiments, a mechanical control or electronic control of user interface 105 is biased in an off state, such that fluid delivery from fluid source 220 is not initiated until the control is activated by an operator of system 10. In some embodiments, a mechanical control or electronic control of user interface 105 is biased in an off state, such that application of vacuum to one or more lumens 111 via vacuum source 230 is not initiated until the control is activated by an operator of system 10. In some embodiments, a mechanical control or electronic control of user interface 105 is biased in an off state, such that inflation of expandable assembly 130 via inflation source 240 is not initiated until the control is activated by an operator of system 10.

In some embodiments, display 104 is configured to provide status information regarding one or more parameters of device 100 and/or fluid delivery assembly 200. In these embodiments, parameter information can comprise information selected from the group consisting of: flow rate such as flow rate delivered from fluid source 220 or inflation source 240 and/or to one or more fluid delivery elements 132 or expandable assembly 130; pressure such as pressure of fluid delivered from fluid source 220 or inflation source 240 or pressure of fluid within a lumen 138 or expandable assembly 130; temperature such as temperature of fluid delivered from fluid source 220 or inflation source 240; volume such as volume of fluid within fluid source 220, within inflation source 240, delivered by a fluid delivery element 132 or contained within expandable assembly 130; and combinations of these. Buttons 103 and/or display 104 can be electrically or otherwise operably attached to cable 202 which can comprise one or more electrical wires, optical fibers and/or hollow tubes (e.g. hydraulic or pneumatic control tubes) that operably attach to controller 210, fluid source 220, vacuum source 230 and/or inflation source 240.

In some embodiments, fluid delivery assembly 200 comprises one or more operator controls and/or information display elements, such as when fluid delivery assembly 200 comprises user interface 205 comprising one or more components selected from the group consisting of: an electrical control; a mechanical control; a switch such as an electrical switch or a mechanical switch; a button; a knob; a lever; a display; a touchscreen; and combinations of these. Information provided by user interface 205 and/or controls accessible via user interface 205 can be separate from or similar to (e.g. redundant with) the information displayed and control provided by buttons 103 and/or display 104 of device 100.

In some embodiments, slide 102 can be attached to the fluid delivery tubes 137 via force-limiting assembly 140. Force limiting assembly 140 can be constructed and arranged to limit the force applied by slide 102 onto the fluid delivery tubes 137 and/or to limit the travel (e.g. forward and/or reverse travel) of at least the proximal portion of fluid delivery tubes 137. In some embodiments, force-limiting assembly 140 is constructed and arranged as described herebelow in reference to force limiting assembly 140 of FIG. 2A and/or force limiting assembly 340 of FIG. 3.

In some embodiments, handle 101 comprises one or more attachment elements, such attachment element 106a and/or 106b. Attachment elements 106a and/or 106b can be constructed and arranged to attach handle 101 to another device, such as to the proximal end of an endoscope, such as to the biopsy port of an endoscope. Attachment elements 106a and/or 106b can comprise one or more mechanical and/or electromechanical attachment elements, such as an element selected from the group consisting of: clip; clamp; strap; electromagnetic coupler such as a solenoid-based clamp; adhesive strip; and combinations thereof. In some embodiments, attachment elements 106a and/or 106b can be operably connected (e.g. mechanically linked), with one or more controls of the attached device. In these embodiments, attachment elements 106a and/or 106b can comprise a control 121a and/or 121b, respectively. Control 121a and/or 121b can be operably connected to an insufflation vacuum control knob and/or a flush control knob of the attached device, such as to activate insufflation or flushing functions of the attached device. Control 121a and/or 121b can comprise a knob, push button, lever or other user input component and an electrical and/or mechanical mechanism, such as a solenoid, a cam and/or a linkage which activates a control of the attached device. Alternatively or additionally, control 121a and/or 121b can be positioned within handle 101, such as is described herebelow in reference to FIG. 12.

Handle 101 can surround various electrical and mechanical components and mechanisms, such as force-limiting assembly 140 described hereabove, as well as electronics module 107. In some embodiments, electronics module 107 comprises a component selected from the group consisting of: battery; microcontroller; memory circuitry; wireless transmitter; wireless receiver; camera such as a CCD camera; optical lens assembly; and combinations thereof. In some embodiments, electronics module 107 comprises a wireless transceiver configured to send or receive communications (e.g. Bluetooth communications) with controller 210 (e.g. to avoid the need for cable 202) and/or with another device of system 10.

In some embodiments, handle 101 comprises two connectable portions, such as distal portion 101a and proximal portion 101b shown in FIG. 1. In these embodiments, system 10 can comprise one or more reusable proximal portions 101b, each of which that can be attached to two or more portions 101a, such as when each portion 101a is used during a single clinical procedure or at least fewer clinical procedures than its attached portion 101b. In these embodiments, certain components (e.g. more expensive components) can be positioned in the reusable portion 101b, such as one or more components selected from the group consisting of: buttons 103, display 104; electronics module 107; a printed circuit board; a transducer such as an audible transducer or a tactile transducer; a light; an LED; a sensor such as a magnetic sensor or a hall effect transducer; and combinations thereof.

In some embodiments, expandable assembly 130 comprises one or more camera components, such as camera assembly 119 shown positioned on the distal end of expandable assembly 130 and oriented toward the proximal end of expandable assembly 130. Camera assembly 119 can comprise one or more components selected from the group consisting of: a camera such as a CCD camera; a lens; a filter; a mirror; and combinations thereof. Camera assembly 119 can be constructed and arranged to collect an image of tissue contacted or otherwise proximate to expandable element 131, and/or an image of one or more fluid delivery elements 132. In some embodiments, fluid source 220 delivers a fluid with a visible agent, such as a dye, such that camera assembly 119 collects an image of delivered fluid and/or expanding tissue that is enhanced with the dye. Camera assembly 119 can be operably attached to electronics module 107 such as via one or more wires and/or optical fibers, not shown but traveling proximally through one or more shafts of shaft 110 and into handle 101. In some embodiments, camera assembly 119 is positioned on the proximal end of expandable assembly 130 and oriented toward the distal end of expandable assembly 130.

System 10 can comprise one or more functional elements, such as one or more of functional elements 109a-109f (singly or collectively, functional element 109) and/or functional elements 209a-209d (single or collectively, functional element 209) shown in FIG. 1. Each functional element 109 can comprise a sensor, a transducer and/or other functional element. In some embodiments, a functional element 109 comprises one or more sensors selected from the group consisting of: pressure sensor; temperature sensor; impedance sensor; pH sensor; flow sensor; ultrasonic sensor; optical sensor; magnetic sensor; hall effect sensor; osmolarity sensor; strain gauge; gas bubble sensor; and combinations of these. Alternatively or additionally, a functional element 109 can comprise one or more transducers selected from the group consisting of: heating element; audio transducer; vibrational transducer; light transducer; magnetic transducer; visual transducer; ultrasound sensor; camera; and combinations of these. In some embodiments, a functional element 109 comprises a pressure regulator and/or a pressure relief valve, such as when functional element 109 is in fluid communication with one or more fluid delivery tubes 137 and/or an inflation lumen of shaft 110d. In some embodiments, a functional element 109 comprises an element selected from the group consisting of: a sensor; a transducer; an ablation element such as one or more electrodes configured to deliver electrical energy such as radiofrequency (RF) energy; a fluid delivery element such as a needle, a fluid jet, a permeable membrane; an exit port; an insufflation port; a heating element; a cooling element; and combinations of these. In some embodiments, one or more functional elements 109 comprise a visualization element, such as to reduce or avoid the need for a separate visualization device such as an endoscope. In these embodiments, functional element 109d can comprise a camera and/or a lens configured to provide an image of one or more of: expandable assembly 130; one or more tissue ports 135; one or more fluid delivery elements 132; shaft 110; tissue proximate expandable assembly 135 and/or tissue ports 135; and combinations of these. Alternatively or additionally, functional element 109d or another functional element 109 can comprise a fluid delivery element constructed and arranged to provide and/or remove insufflation fluids.

One or more functional elements 109 can comprise a sensor configured to detect occlusion, such as an occlusion in a lumen or other location of device 100. In some embodiments, multiple functional elements 109 each comprise a sensor configured to detect an occlusion (e.g. via low flow, low pressure, etc.) in one or more fluid delivery tubes 137 (e.g. collectively or independently), one or more vacuum lumens 111 (e.g. collectively or independently), or an occlusion in one or more of tubes 201. In some embodiments, one or more functional elements 109 can be configured to detect and/or confirm adequate flow (e.g. within one or more fluid delivery tubes 137) and/or adequate vacuum (e.g. within one or more lumens 111 and/or tissue capture ports 135), collectively or independently (e.g. via multiple independent functional elements 109).

Device 100 can include one or more sensors, transducers and/or other functional elements as described hereabove. Device 100 can include one or more functional elements positioned in, on and/or within handle 101, such as functional element 109a positioned in handle portion 101b (e.g. a reusable portion as described hereabove) and functional element 109b positioned in handle portion 101a (e.g. a portion of handle 101 used in fewer clinical procedures than portion 101b). In some embodiments, functional elements 109a and/or 109b comprise a sensor configured to monitor a voltage or current, such as the voltage or current of a power supply of electronics module 107. Functional elements 109a and/or 109b can comprise a sensor (e.g. an ultrasonic sensor) configured to monitor fluid flowing through one or more tubes passing through handle 101, such as to produce a signal correlating to flow rate, temperature and/or the presence of one or more gas bubbles present in fluid passing through a portion of handle 101. Functional elements 109a and/or 109b can comprise a transducer, such as a vibrational or audible transducer used to alert an operator of an alert or other condition of system 10. In some embodiments, device 100 and/or system 10 is constructed and arranged to activate an alert signal delivered by a functional element 109a and/or 109b, when one or more of the following conditions occur: vacuum is applied to one or more tissue capture ports 135; expandable assembly 130 is radially expanded; fluid is being delivered into tissue; and one or more fluid delivery elements 132 are in an advanced position.

Device 100 can further include functional element 109c comprising one or more functional elements positioned on, in and/or within shaft 110 as shown. Functional element 109c can comprise a sensor such as a sensor configured to provide a signal correlating to one or more of: flow rate; pressure; presence of a gas bubble; temperature; and combinations of these. Alternatively or additionally, functional element 109c can comprise a transducer, such as a vibrational transducer, a pressure regulator and/or a pressure relief valve.

Device 100 can further include functional element 109d, positioned on, in and/or within expandable assembly 130 as shown. Functional element 109d can comprise a sensor configured to produce a signal correlating to one or more of: pressure; volume; temperature; and combinations of these. Functional element 109d can comprise a sensor configured to produce a signal correlating to adequate expansion of expandable assembly 130 (e.g. adequate expansion of expandable element 131 such as when expandable element 131 comprises a balloon). In some embodiments, functional element 109d comprises a sensor configured to produce a signal correlating to balloon expansion and/or balloon pressure and controller 210 is configured to perform a function based on the produced signal, the function selected from the group consisting of: stop fluid infusion when the balloon pressure reaches or exceeds a pressure threshold; stop fluid infusion when the balloon pressure is below a pressure threshold; expand the balloon until it reaches a pressure threshold, such as a pressure of at least 0.4 psi or at least 0.8 psi; maintain the balloon at a pre-determined pressure level for a pre-determined time period prior to beginning delivery of fluid to tissue by one or more fluid delivery elements 132; and combinations of these.

Device 100 can further comprise functional element 109e, positioned on, in and/or within lumen 111 as shown. Functional element 109e can comprise a sensor configured to produce a signal correlating to one or more of: occlusion; pressure; flow rate; and combinations of these.

Device 100 can further comprise functional element 109f, positioned on, in and/or within lumen 112 and/or fluid delivery element 132 as shown. Functional element 109f can comprise a sensor configured to produce a signal correlating to one or more of: flow rate; pressure; presence of one or more gas bubbles; osmolarity; occlusion; temperature; and combinations of these. Functional element 109f can comprise a sensor to produce a signal correlating to one or more of: fluid being delivered from fluid delivery tube 137 and/or fluid delivery element 132 into tissue; fluid delivery tube 137 and/or fluid delivery element 132 in an advanced and/or retracted position; position of fluid delivery tube 137 and/or fluid deliver element 132 such as is described in reference to FIG. 3 herebelow; and combinations of these.

In some embodiments, controller 210 and/or electronics module 107 are configured to enter an alarm or other alert state when two conditions that are incompatible occur, such as when signals provided by one or more functional elements 109 indicate that one or more of the following incompatible conditions are present: fluid delivery element 132 is retracted or retracting while fluid is flowing through fluid delivery element 132; fluid delivery element 132 is advanced and a diameter of expandable assembly 130 is below a threshold; fluid delivery element 132 is advanced and vacuum level in tissue capture port 135 and/or lumen 111 is below a threshold; balloon pressure of expandable assembly 130 is below a first threshold and vacuum level in a vacuum location such as tissue capture port 135 and/or lumen 111 is above a second threshold; balloon pressure of expandable assembly 130 is above a threshold and fluid is flowing (e.g. at a sufficient flow rate) through fluid delivery element 132; balloon pressure of expandable assembly 130 is below a threshold and fluid is flowing (e.g. at a sufficient flow rate) through fluid delivery element 132; and combinations of these.

Fluid delivery assembly 200 can comprise one or more functional elements, such as one or more sensors, transducers and/or other functional elements as described hereabove. Fluid delivery assembly 200 can comprise functional elements 209a, 209b and 209c positioned in, on and/or within fluid source 220, vacuum source 230 and/or inflation source 240, respectively. In some embodiments, one or more of functional elements 209a-c are positioned in, on and/or within one or more tubes 201.

Fluid delivery assembly 200 can comprise functional element 209d positioned in, on and/or within controller 210.

Figure 7:
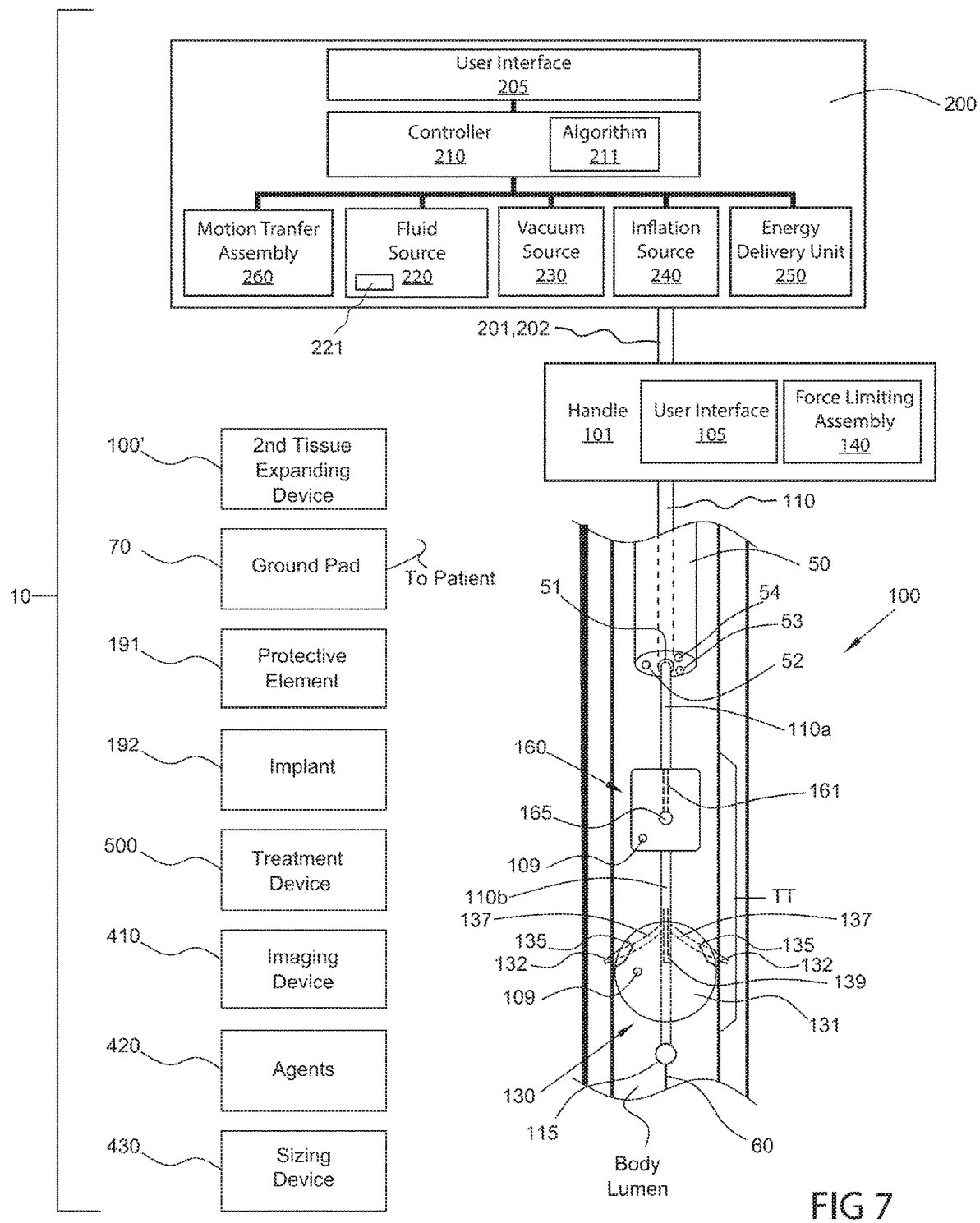
FIG. 7 is a schematic view of an injectate delivery system, consistent with the present inventive concepts.

In some embodiments, device 100 further comprises a treatment element, such as an ablation element or other treatment element such as is described herebelow in reference to FIG. 7. In some embodiments, shaft 110 comprises one or more working channels or other lumens, such as a lumen configured to provide insufflation as described herein. In some embodiments, device 100 comprises a steering mechanism for deflecting or otherwise steering shaft 110, such as is also described herebelow in reference to FIG. 7. In some embodiments, shaft 110 comprises multiple shafts arranged in a helical geometry along at least a portion of the length of shaft 110, such as is described herebelow in reference to FIG. 8.

Figure 9:
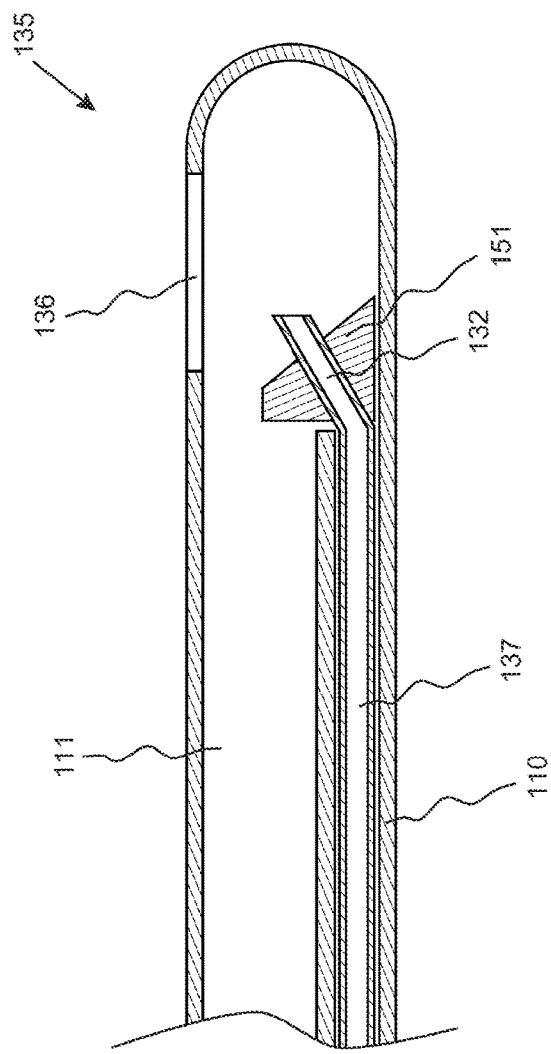
FIG. 9 is a side sectional view of the distal portion of an injectate delivery device including a fluid delivery element positioned and oriented to penetrate tissue as tissue is captured within a tissue port, consistent with the present inventive concepts.
Figure 9A:
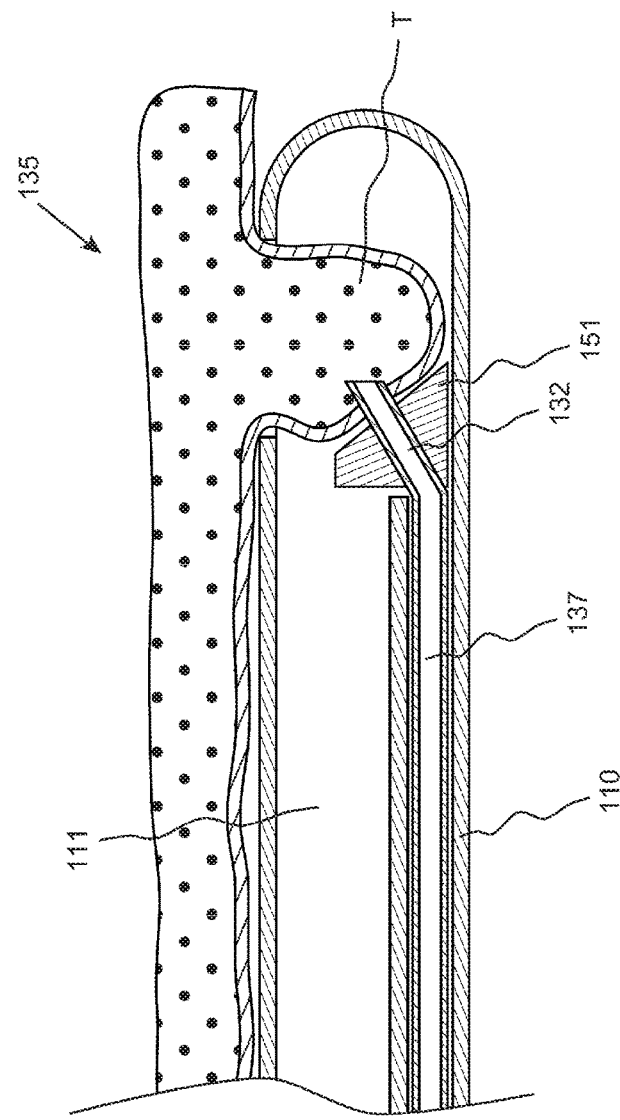
FIG. 9A is a side sectional anatomical view of the injectate delivery device of FIG. 9 after tissue has been captured into the tissue port and the fluid delivery element has penetrated the tissue, consistent with the present inventive concepts.

In some embodiments, one or more fluid delivery elements 132 are positioned and oriented such that when tissue is drawn into the associated tissue capture port 135, the tissue can be penetrated by the fluid delivery element 132 (e.g. without advancement of the fluid delivery element 132), such as described herebelow in reference to FIGS. 9 and 9A. In these embodiments, slide 102 and its associated mechanism can be avoided or their function reduced. Alternatively or additionally, one or more tissue capture ports 135 can be constructed and arranged to translate (e.g. be translated by an operator) to cause tissue captured within port 135 to be penetrated by fluid delivery element 132, such as is described herebelow in reference to FIGS. 10A, 10B, 11A and 11B.

Referring now to FIG. 2A, a side view of a particular embodiment of the force limiting assembly of FIG. 1 is illustrated, consistent with the present inventive concepts. Force limiting assembly 140 comprises one or more compression elements, such as springs 142a-c. Force limiting assembly 140 further comprises blocks 143a-c, channels 146a-c and mechanical stops 141 and 148. Device 100 comprises fluid delivery tubes 137a-c, vacuum lumens 111a-c, vacuum ports 118a-c, seals 117a-c, ports 144a-c and openings 145a-c. For illustrative clarity, only reference designations 142a, 143a, 146a, 111a, 118a, 117a, 144a and 145a are listed on FIG. 2A.

Springs 142a-c can comprise a coil spring and/or other compression spring. Channels 146a-c can comprise a relatively uniform recess in handle 101 sized to allow blocks 143a-c to move within channel 146a-c (e.g. move back and forth within channel 146a-c), respectively.

Slide 102 operably attaches to fluid delivery tubes 137a-c via force limiting assembly 140, such that slide 102 can translate along axis 147. Slide 102 is attached to springs 142a-c. Springs 142a-c are attached to blocks 143a-c, respectively. Fluid delivery tubes 137a-c are attached to blocks 143a-c, respectively. When slide 102 is advanced (i.e. moved to the right of the page), springs 142a-c elongate and apply a pulling force to blocks 143a-c, respectively, such that blocks 143a-c translate (to the right) within channels 146a-c, respectively, and fluid delivery tubes 137a-c, respectively advance. When slide 102 is retracted (i.e. moved to the left of the page), springs 142a-c compress and apply a pushing force to blocks 143a-c, respectively, such that blocks 143a-c translate (to the left) within channels 146a-c, respectively, and fluid delivery tubes 137a-c, respectively retract.

Mechanical stop 141 is positioned to limit the proximal travel of slide 102, while mechanical stop 148 is positioned to limit the distal travel of slide 102. Channels 146a-c can have sufficient length and can be positioned relative to stops 141 and 148 such that blocks 143a-c, respectively, never reach either end of channels 146a-c. Stops 141 and 148 can be positioned such that springs 142a-c never fully compress (i.e. when slide 102 contacts stop 141) and springs 142a-c never plastically deform (i.e. when slide 102 contacts stop 148). In this configuration, the force applied to each of fluid delivery tubes 137a-c is limited to a small range of forces applied by springs 142a-c, respectively, experienced throughout the travel of slide 102 from stop 141 to stop 148. In this configuration, the force applied to each fluid delivery tube 137 via slide 102 is force limited (e.g. to prevent damage to fluid delivery tube 137 and/or any component attached thereto and/or interfacing therewith), and individually compensated (e.g. when shaft 110 is in a curvilinear geometry such as that described herebelow and shown in FIG. 2B). In some embodiments, one or more of springs 142a-c comprise an effective length of between 17 mm and 37 mm, such as a length of approximately 27 mm. In some embodiments, one or more of springs 142a-c comprise a spring rate of between 2.1 lb/in and 3.1 lb/in, such as a spring rate of approximately 2.6 lb/in. In some embodiments, springs 142a-c, blocks 143a-c and/or channels 146a-c are similar. In other embodiments, springs 142a-c, blocks 143a-c and/or channels 146a-c are dissimilar.

Fluid delivery tubes 137a-c fluidly attach to ports 144a-c, respectively. Ports 144a-c also fluidly attach to one or more tubes 201, not shown but described in reference to FIG. 1 hereabove, fluidly connecting fluid source 220 to fluid delivery tubes 137a-c. Handle 101 can comprise openings 145a-c which each allow an individual tube 201 to pass therethrough, and accommodate translation of blocks 143a-c as slide 102 is moved back and forth.

Also shown in FIG. 2A are ports 118a-c, which fluidly attach to lumens 111a-c respectively. Ports 118a-c also fluidly attach to one or more tubes 201, not shown but described in reference to FIG. 1 hereabove, fluidly connecting vacuum source 230 to lumens 111a-c. Handle 101 can comprise one or more openings configured to allow the associated tubes 201 to pass therethrough. Lumens 111a-c can each comprise a sealing element, seal 117a-c, respectively, on the proximal end of lumens 111a-c.

As described above in reference to FIG. 1, one or more controls of the devices and systems of the present inventive concepts can be biased to a particular state, such as an on state, an off state, an advanced state and/or a retracted state. In the embodiment of FIG. 2A, a control, slide 102 is biased such that fluid delivery tubes 137 and fluid delivery elements 132 are in the retracted state (i.e. an "off" state) until a force is applied to slide 102. The bias is provided by spring 149 which is attached at one end to slide 102 and at the opposite end to handle 101 such that when no external force is applied to slide 102, fluid delivery elements 132 are in the retracted state.

Referring additionally to FIG. 2B, a sectional side view of a segment of shaft 110 in a curved geometry is illustrated, consistent with the present inventive concepts. Fluid delivery tube 137a is on the inside of the curve shown, while fluid delivery tube 137c is on the outside of the curve shown. In this configuration, fluid delivery tube 137c travels a greater distance to accommodate the curve than does fluid delivery tube 137a. Force limiting assembly 140 is constructed and arranged such that the varied distance traveled can be accommodated, such as when block 143a advances (e.g. to the right of the page) less than block 143c to accommodate the curve shown in FIG. 2B.

Referring additionally to FIG. 2C, an end sectional view of a portion of shaft 110a is illustrated, consistent with the present inventive concepts. Shaft 110a comprises lumen 112a and lumen 111a. Lumen 112a surrounds fluid delivery tube 137a. Lumen 111a is fluidly attached to tissue port 135a on its distal end, and sealing element 117a can be positioned on its proximal end (as shown in FIG. 2A). Lumen 112a can comprise a relatively circular geometry as shown, and slidingly receive fluid delivery tube 137a. Lumen 111a can comprise a geometry to maximize cross-sectional area of lumen 111a (e.g. a non-circular geometry), such as when shaft 110a comprises a relatively circular outer wall. Lumen 111a can comprise a cross sectional area between 0.8 mm$^2$ and 2.0 mm$^2$, such as a cross sectional area of 1.0 mm$^2$ when shaft 110a comprises a diameter of approximately 0.090".

Referring now to FIG. 3, side sectional and magnified side sectional views of the proximal and distal portions, respectively, of an injectate delivery including a force limiting assembly are illustrated, consistent with the present inventive concepts. Device 100 includes force limiting assembly 340 as shown. Device 100 can comprise a single fluid delivery element 132 as shown, or multiple fluid delivery elements as described hereabove in reference to FIGS. 1, 2A and 2B. Force limiting assembly 340 can be positioned in, on and/or within handle 101. Force limiting assembly 340 operably attaches to fluid delivery tube 137 which in turn is fluidly attached to fluid delivery element 132. Fluid delivery tube 137 is attached to block 343. Block 343 is positioned in channel 346, typically an elongate recess in handle 101 sized to slidingly receive block 343 such that block 343 can translate back and forth in direction 347 as shown. Block 343 frictionally engages lead screw 349 such that rotation of lead screw 349 in a first direction causes block 343 to advance in channel 346 (and correspondingly advance fluid delivery tube 137 and fluid delivery element 132), and rotation of the lead screw 349 in the opposite direction causes lead screw 349 to retract in channel 346 (and correspondingly retract fluid delivery tube 137 and fluid delivery element 132).

Lead screw 349 is driven by motor 350 via clutch 351. Clutch 351 is constructed and arranged to limit the force applied to lead screw 349, and thus limit the push and/or pull force applied to fluid delivery tube 137 and fluid delivery element 132, such as to prevent damage to fluid delivery tube 137, fluid delivery element 132 and/or any components attached thereto or interfacing therewith. Electronics module 107 is attached to motor 350 via cable 352. User interface 105 is configured to control motor 350 such as to operably advance and/or retract one or more fluid delivery elements 132. This advancement and/or retraction can be performed automatically or at least semi-automatically. User interface 105 and/or electronics module 107 can be of similar construction and arrangement as corresponding components of device 100 described hereabove in reference to FIG. 1.

Device 100 can further include stops 134a and 134b. Stops 134a and 134b can be configured to provide proximal and distal stops which engage collar 133, which surrounds fluid delivery tube 137 and/or fluid delivery element 132. In some embodiments, stops 134a and/or 134b comprise a functional element 109, such as a sensor configured to produce a signal corresponding to proximity of collar 133 to stops 134a and/or 134b and/or produce a signal corresponding to force applied by collar 133 to stops 134a and/or 134b. In these embodiments, advancement of fluid delivery tube 137 and/or fluid delivery element 132 can be made based on the position of collar 133 (e.g. which corresponds to the position of fluid delivery element 132). Alternatively or additionally, advancement of fluid delivery tube 137 and/or fluid delivery element 132 can be made using a force feedback signal and/or proximity signal provided by stops 134a and/or 134b (e.g. via one or more wires not shown but operably connected to electronics module 107). The force feedback information can be used dynamically to adjust the position of block 343 and correspondingly translate fluid delivery tube 137 and/or fluid delivery element 132 based on a force measured at a distal location in shaft 110a (i.e. at a location proximate port 135a).

Although the device 100 shown in FIG. 3 comprises a single fluid delivery element 132 and a force limiting assembly 340 that limits the force applied to a single fluid delivery tube 137, device 100 can comprise multiple fluid delivery elements 132 and force limiting assembly 340 can be constructed and arranged to limit force applied to multiple fluid delivery tubes 137. For example, force limiting assembly 340 can comprise multiple lead screws 349 which attach to one or more motors 350 via one or more clutches 351.

Referring now to FIGS. 4A-4D, a series of steps for delivering fluid into tissue captured by a tissue port is illustrated, consistent with the present inventive concepts. In FIGS. 4A-4D, the distal portion of a fluid expanding device 100 is illustrated. In some embodiments, fluid expanding device 100 is of similar construction and arrangement as device 100 of FIGS. 1 and 1A.

In FIG. 4A, tissue capture port 135 has been positioned proximate a surface of tissue T, such as proximate the mucosal layer of a portion of the gastrointestinal tract, such as the mucosal layer of the duodenum of a patient. Device 100 can be inserted over a guidewire and/or through a body access device such as a laparoscopic port or endoscope. Positioning of port 135 at a desired axial location of the GI tract can be accomplished by advancing or retracting shaft 110 while using a visualization device such as a camera (e.g. the camera of an endoscope) or an imaging instrument such as a fluoroscope, ultrasound imager, MRI or the like. Radial positioning of port 135 proximate the surface of tissue can comprise expanding a component onto which one or more ports 135 are attached, such as a balloon or other expanding element. In some embodiments, one or more tissue capture ports 135 are attached to an expanding element similar to expanding element 131 described hereabove in reference to FIG. 1. Device 100 includes fluid delivery element 132 fluidly attached to fluid delivery tube 137. Collar 133 surrounds fluid delivery element 132 and/or fluid delivery tube 137 which resides in lumen 112. Stops 134a and 134b can be included to limit the travel of fluid delivery element 132, all as is described hereabove in reference to FIGS. 1, 1A and/or 3. Tissue capture port 135 includes opening 136 which is in fluid communication with lumen 111.

In FIG. 4B, vacuum has been applied to opening 136 via lumen 111 such that a portion of tissue T is captured by (e.g. drawn into or otherwise tends toward) tissue capture port 135. Fluid delivery element 132 has been advanced into tissue T, such as when fluid delivery element 132 comprises a sharpened needle. Subsequently, one or more injectates can be delivered into tissue T. In some embodiments, fluid delivery element 132 comprises a water jet or iontophoretic element, such that fluid delivery element 132 can penetrate into tissue T or simply reside proximate but external to tissue T during delivery of the injectate. In some embodiments, advancement of one or more fluid delivery elements 132 is performed with a force-limiting mechanism, such as is described hereabove in reference to force limiting assembly 140 of FIG. 1 or 2A, or force limiting assembly 340 of FIG. 3. In some embodiments, fluid delivery element 132 is advanced at least semi-automatically, such as via lead screw 349 and/or motor 350 described hereabove in reference to FIG. 3.

In FIG. 4C, the injectate has been delivered into tissue T, and fluid delivery element 132 has been retracted. In some embodiments, retraction of one or more fluid delivery elements 132 is performed with a force-limiting mechanism, such as is described hereabove in reference to force limiting assembly 140 of FIG. 1 or 2A, or force limiting assembly 340 of FIG. 3. In some embodiments, fluid delivery element 132 is retracted at least semi-automatically, such as via lead screw 349 and/or motor 350 described hereabove in reference to FIG. 3.

In FIG. 4D, the vacuum is released from lumen 111 such that tissue T evacuates tissue capture port 135. In some embodiments, a positive pressure is applied to lumen 111, such as via the fluid delivery assembly 200 of FIG. 1, to discharge tissue T from tissue capture port 135. In some embodiments, the circumferential span of tissue expanded in the steps illustrated in FIGS. 4A-D comprises a circumferential span of approximately 360° of an axial segment, and/or an axial length of approximately between 2 cm and 5 cm, such as between 2 cm and 4 cm or between 3 cm and 5 cm.

Subsequently, the distal portion of device 100 can be repositioned (e.g. advanced, retracted and/or rotated), and the steps shown in FIGS. 4A-D repeated one or more additional times, such as to expand tissue in multiple locations of the gastrointestinal tract, such as to substantially expand a submucosal layer of the duodenum comprising a cumulative axial length of at least 5 cm, at least 10 cm, or at least 15 cm. In some embodiments, a cumulative axial of at least 4 cm or at least 5 cm is expanded, followed by an ablation of tissue with an axial length of at least 3 cm. The cumulative axial length of expanded tissue can comprise a relatively continuous axial length of the GI tract or a series of two or more discrete segments.

Although the device 100 shown in FIGS. 4A-D comprises a single fluid delivery element 132 and a single tissue capture port 135, device 100 can comprise multiple fluid delivery elements 132 and multiple tissue capture ports 135, such as a construction comprising a circumferential array of tissue capture ports 135, such as two tissue capture ports 135 arranged along a circumference with 180° spacing, two tissue capture ports 135 arranged along a circumference with 120° spacing, or four tissue capture ports 135 arranged along a circumference with 90° spacing. In these embodiments, the application and/or release of vacuum applied to the multiple tissue capture ports 135, and/or the advancement and/or retraction of the multiple fluid delivery elements 132 (e.g. one or more of the steps shown in FIGS. 4A-D), can be performed simultaneously or sequentially.

Figure 5A:
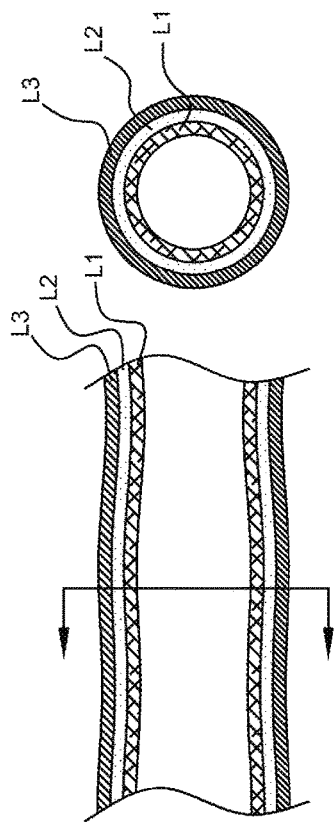
FIGS. 5A, 5B and 5C are a series of side sectional and end anatomical views of a segment of luminal wall tissue, prior to, during and after full circumferential tissue expansion, respectively, consistent with the present inventive concepts.
Figure 5B:
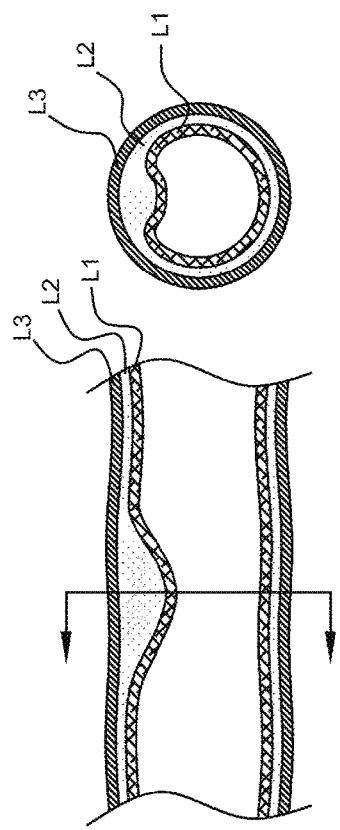
Figure 5C:
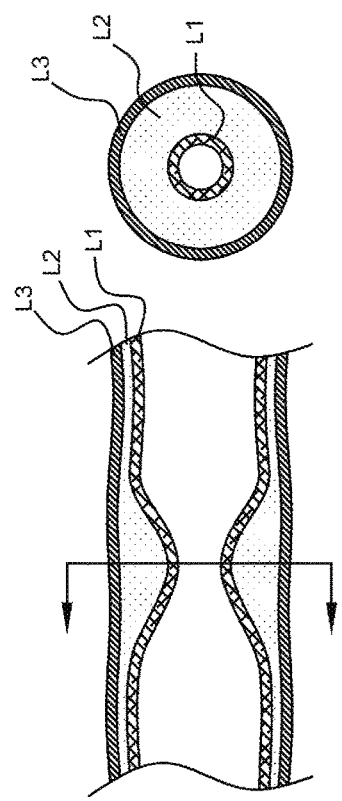

Referring now to FIGS. 5A, 5B and 5C, side and end sectional anatomical views of a segment of luminal wall tissue are illustrated, prior to, during and after full circumferential tissue expansion, respectively, consistent with the present inventive concepts. In FIG. 5A, a side and end sectional view of a segment of luminal wall tissue includes inner layer L1, mid layer L2 and outer layer L3, prior to any expansion by an injectate delivery device of the present inventive concepts. In FIG. 5B, a tissue expansion has occurred at a single location toward the top of the page as shown, within tissue layer L2. In FIG. 5C, a tissue expansion has occurred for a full 360° segment of layer L2. In some embodiments, a full or near full circumferential expansion (e.g. greater than approximately 300° of tissue expansion, greater than approximately 320° of tissue expansion, or greater than approximately 330° of tissue expansion), is performed in a relatively single step, such as from multiple fluid delivery elements. In other embodiments, a full or near full circumferential expansion is performed in multiple steps, such as from one or more fluid delivery elements that are configured to inject or otherwise deliver fluid in a first step and be rotated in one or more subsequent steps, each rotation followed by a delivery of fluid into tissue.

The expansion of a tissue layer, such as layer L2 of FIGS. 5A through 5C, can be performed to cause a reduction in cross sectional area of the lumen, such as a reduction to between 80% and 85% of the pre-expansion cross sectional area (e.g. a 30 mm lumen reduced to a 25 mm lumen), or a reduction to 75% of the pre-expansion cross-sectional area. In some embodiments, a pre-expansion cross sectional diameter of approximately 25 mm to 28 mm is reduced by between 2 mm and 4 mm Some body lumens comprise an inner layer including a non-smooth surface, such as the lining of the duodenum or jejunum including one or more folds known as the plicae. In some embodiments, the tissue expansion causes folds such as plicae to be smoothed and/or widened. This modification can be useful in subsequent treatments of the lumen's inner lining, such as to improve the results of one or more tissue ablation procedures.

Numerous forms and locations of patient tissue can be expanded by the devices, systems and methods of the present inventive concepts. In some embodiments, the tissue to be expanded comprises submucosal tissue, such as submucosal tissue of the duodenum. The devices systems and methods of the present inventive concepts can be constructed and arranged to avoid expanding one or more layers of tissue, such as when the muscularis or serosal layer of the duodenum is prevented from being expanded. Applicable tissue can comprise luminal wall tissue or other tissue layers. Applicable tissue locations to be expanded can include luminal wall tissue selected from the group consisting of: a gastrointestinal tissue layer; a duodenal tissue layer; an esophageal tissue layer; a jejunal tissue layer; an ileal tissue layer; a colonic tissue layer; and combinations of these. Alternatively or additionally, tissue to be expanded can comprise tissue selected from the group consisting of: a stomach tissue layer; a bladder tissue layer; an oral cavity tissue layer; a uterine tissue layer; and combinations of these.

Figure 6A:
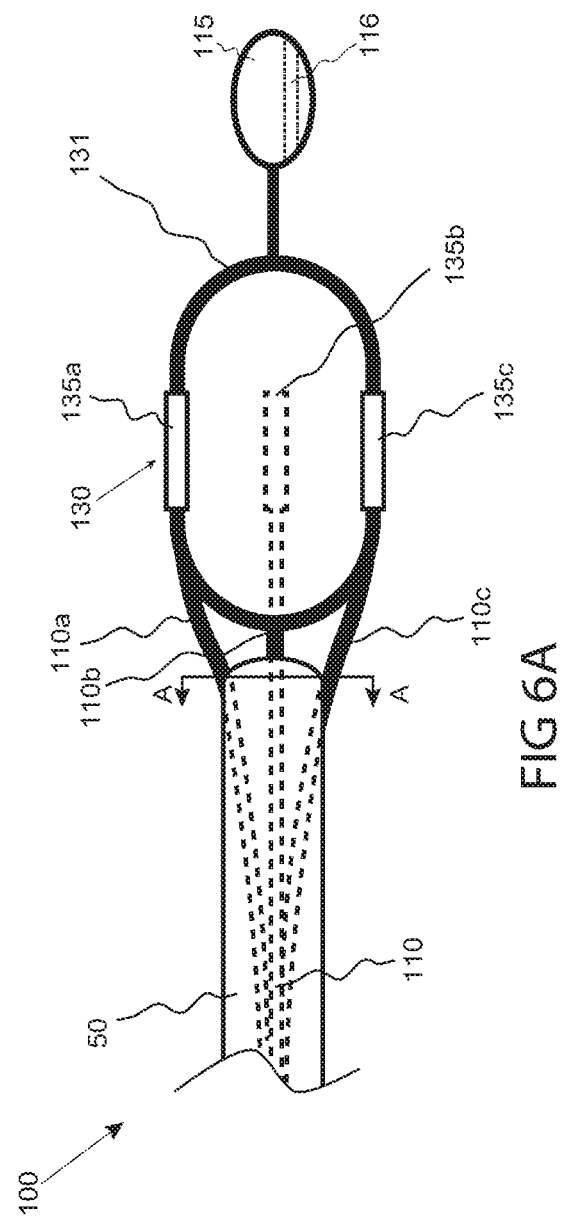
FIGS. 6A and 6B are side sectional and end sectional views, respectively, of the distal portion of an injectate delivery device including a quadrifurcated shaft, consistent with the present inventive concepts.
Figure 6B:
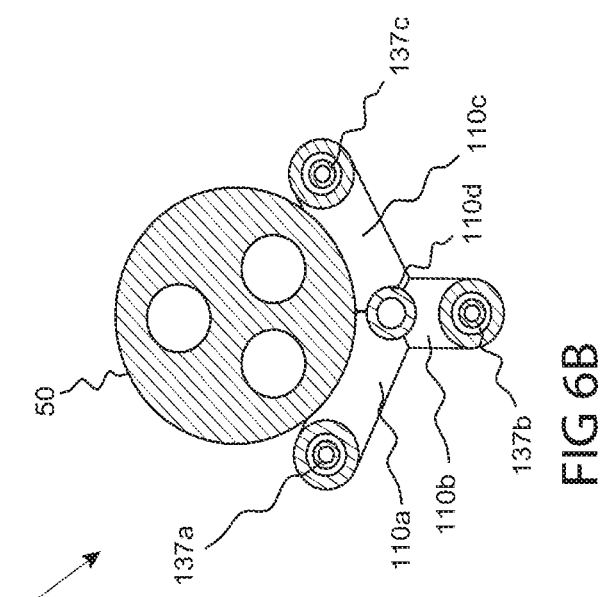

Referring now to FIGS. 6A and 6B, side and end sectional views of the distal portion of an injectate delivery device including a quadrifurcated shaft is illustrated, consistent with the present inventive concepts. Device 100 can have similar construction and arrangement to device 100 of FIG. 1, with similar components sharing the same or like reference numbers. As shown in FIGS. 6A and 6B, the distal portions of shafts 110a, 110b, 110c, and 110d diverge from each other (e.g. the separation beginning at a location approximately 140 mm from the distal end of device 100), creating a space which is sized and configured to allow an elongate device, such as an elongate visualization device, such as endoscope 50, to be positioned in between at least two of shafts 110a, 110b and 110c without applying significant force and/or significantly deflecting any of shafts 110a, 110b and/or 110c and/or expandable assembly 130. Shafts 110a, 110b and/or 110c are attached to expandable element 131 of expandable assembly 130. Expandable element 131 can be a balloon or other expandable element constructed and arranged to radially expand to position ports 135a, 135b and 135c in a circumferential geometry with a diameter of at least 20 mm, such as a diameter between 25 mm and 36 mm, a diameter between 28 mm and 36 mm, or a diameter of approximately 32 mm.

In some embodiments, shafts 110a, 110b and/or 110c are oriented such as to enable the distal end of endoscope 50 (e.g. a scope with a distal portion diameter between 7 mm and 11 mm) to be within 1.5 cm, 2.0 cm, 3.0 cm, or within 9.0 cm of ports 135a, 135b and/or 135c, such as to provide a visual or other image of ports 135a-c and/or tissue proximate ports 135a-c. In some embodiments, shaft 110 comprises four or more separate shafts, and the geometric arrangement of two or more of the shafts 110 is sufficient to allow the distal portion of endoscope 50 to be positioned therein, similar to the arrangement shown in FIGS. 6A and 6B.

Referring now to FIG. 7, a schematic view of a system for expanding tissue is illustrated, consistent with the present inventive concepts. System 10 is configured to deliver an injectate into tissue, to expand one or more layers of tissue (e.g. to perform or full or partial circumferential expansion of one or more layers of submucosal tissue of an axial segment of the GI tract). System 10 can be further configured to treat one or more layers of tissue, such as to treat one or more corresponding inner layers of tissue (e.g. the mucosal layer of the same axial segment of the GI tract). Target tissue TT of the embodiment of FIG. 7 collectively includes portions of tissue to be expanded and/or portions of tissue to be treated. Target tissue TT shown includes tissue of an axial segment of the GI tract comprising submucosal tissue to be expanded and mucosal tissue to be subsequently treated. In some embodiments, one or more layers (e.g. one or more inner layers) of submucosal tissue that are expanded are also treated or otherwise affected by a treatment performed by system 10, as described herebelow. Expansion and/or treatment of all or a portion of target tissue TT (hereinafter "target tissue TT") by system 10 can be configured to treat one or more patient diseases or disorders selected from the group consisting of: diabetes; obesity or otherwise being overweight; hypercholesterolemia; exercise intolerance; psoriasis; hypertension; metabolic syndrome; and combinations of these. Tissue expansion of a first portion of target tissue TT by device 100 can greatly alleviate the need for precision of treatment, such as precision of delivery of energy and/or precision of delivery of an ablative fluid, due to the increased size (e.g. increased depth) of the to-be-treated portion of target tissue TT which can include an associated safety-margin of tissue to which treatment causes no significant adverse event (e.g. an expanded submucosal layer prior to a mucosal layer ablation). In the embodiment of FIG. 7, target tissue TT includes one or more tubular tissue segments, such as one or more axial tissue segments within a body lumen of a mammalian patient. In some embodiments, target tissue TT that is expanded and/or treated comprises a continuous segment (e.g. a continuous, full-circumferentially treated segment) and/or multiple discontinuous segments (e.g. multiple full-circumferentially treated segments) of a duodenum, such as a volume of tissue comprising at least 50% of the duodenal mucosa, or at least 67% of the duodenal mucosa. The entirety of tissue treated can comprise tissue distal to the ampulla of Vater, such as in a procedure in which at least 50% of post-ampullary duodenal mucosa is treated. In some embodiments, the target tissue TT comprises a treatment portion including duodenal mucosal tissue and a safety-margin portion comprising at least an innermost layer of the duodenal submucosa (e.g. an innermost layer of duodenal submucosa expanded by a device of the present inventive concepts). System 10 can be configured to treat the duodenal mucosa while avoiding damage to duodenal adventitial tissue (e.g. non-target tissue), such as by avoiding damage to: tissue beyond the mucosa; tissue beyond the superficial submucosa; and/or tissue beyond the deep submucosa.

System 10 can include one or more injectate delivery devices such as first injectate delivery device 100 and second injectate delivery device 100' (singly or collectively, device 100). First device 100 and/or second device 100' can be further constructed and arranged to treat target tissue, as described in detail herein. Alternatively or additionally, system 10 can include a separate treatment device 500. First device 100 can be used in a first clinical procedure comprising expansion and/or treatment of target tissue TT, and second device 100' can be used in a second clinical procedure comprising expansion and/or treatment of target tissue TT. In some embodiments, the second clinical procedure is performed at least twenty-four hours after the first clinical procedure. Target tissue TT expansions performed in the second clinical procedure can be constructed and arranged based on one or more outcomes of the first clinical procedure. Additional target tissue TT expansion and/or treatment devices can be included in system 10, such as to perform a third or other subsequent clinical procedures including target tissue TT expansion and/or treatments.

First device 100 and second device 100' can be similar or dissimilar devices, and can be constructed and arranged to perform similar or dissimilar tissue expansions and/or treatments to similar or dissimilar volumes of tissue. Differences between first device 100 and second device 100' can include but are not limited to: type of fluid delivery element; type of fluid delivered to expand tissue; type of ablative treatment provided such as type of energy delivered; type of non-ablative treatment provided; type of treatment assembly; type of treatment element; length of the device; diameter of a portion of the device; and combinations of these. In some embodiments, first device 100 comprises a first treatment element constructed and arranged to deliver a different form of energy than a second treatment element of second device 100'. Alternatively or additionally, first device 100 can comprise a first treatment element with a different geometry (e.g. different diameter, length and/or tissue contact surface area or shape), than a second treatment element of second device 100'.

System 10 can include one or more body introduction devices, such as endoscope 50. Endoscope 50 can comprise a standard GI endoscope such as an endoscope with one or more working channels configured to slidingly receive first device 100 (as shown), second device 100' and/or another elongate device of system 10. Additionally or alternatively, system 10 can include other body introduction devices, such as a laparoscopic port, vascular introducer and/or other introducer.

System 10 includes fluid delivery assembly 200, which includes user interface 205, controller 210, fluid source 220, vacuum source 230 and inflation source 240. Fluid delivery assembly 200 is connected to handle 101 of device 100 via tubes 201 and cable 202. User interface 205, controller 210, fluid source 220, vacuum source 230, inflation source 240, tubes 201 and cable 202 can be of similar construction and arrangement to similar components of device 100 of FIG. 1. System 10 can include injectate 221, which is delivered to device 100 by fluid source 220. Injectate 221 can comprise a fluid selected from the group consisting of: water; saline; fluid with a dye such as a visible dye such as indigo carmine; methylene blue; India ink; SPOT™ dye; a gel; a hydrogel; a protein hydrogel; a fluid containing a visualizable media such as a media visualizable under X-ray; ultrasound and/or magnetic resonance imaging; and combinations of these. In some embodiments, injectate 221 can comprise a material constructed and arranged to cause a narrowing or other restriction that results in a therapeutic benefit to the patient, such as is described in applicant's co-pending International Patent Application Serial Number PCT/US2014/066829, entitled "Systems, Devices and Methods for the Creation of a Therapeutic Restriction in the Gastrointestinal Tract", filed Nov. 21, 2014, the entire content of which is incorporated herein by reference in its entirety. In these embodiments, injectate 221 can comprise a material configured to remain in place (e.g. within one or more tissue layers of the GI tract) for an extended period of time, such as at least 1 day, 1 week, 1 month, 3 months or 6 months. Injectate 221 can comprise a biopolymer (e.g. ethylene vinyl alcohol) and/or an adhesive (e.g. cyanoacrylate)

In some embodiments, fluid delivery assembly 200 comprises an energy delivery unit, EDU 250. EDU 250 can be constructed and arranged to deliver ablative fluids or other ablative energy to one or more components of device 100, such as treatment assembly 160 described herebelow, or to a separate treatment device, such as treatment device 500 also described herebelow. In some embodiments, fluid delivery assembly 200 comprises a motion control mechanism, motion transfer assembly 260. Motion transfer assembly 260 can be constructed and arranged to rotate, translate, vibrate and/or otherwise move one or more components of device 100, such as expandable assembly 130 and/or treatment assembly 160. In some embodiments, motion transfer assembly 260 is constructed and arranged to rotate another device or component of system 10, such as a treatment element or other component of treatment device 500. In some embodiments, motion transfer assembly 260 is constructed and arranged to steer a shaft of one or more components of system 10, such as shaft 110 of device 100 and/or a shaft of treatment device 500.

Device 100 can comprise one or more shafts 110 (e.g. a single shaft or multiple elongate shafts) which attach on their proximal end to handle 101. A distal portion of one or more shafts 110 include radially expandable assembly 130 comprising one or more fluid delivery elements 132, each attached to a fluid delivery tube 137 as described hereabove in reference to device 100 of FIG. 1. Fluid delivery tubes 137 travel proximally within one or more shafts 110 and into handle 101. Handle 101 fluidly attaches (e.g. via one or more ports and/or via tubes 201) to fluid delivery assembly 200 such that injectate 221 and/or another fluid can be provided to fluid delivery element 132 via fluid source 220, such as is described hereabove in reference to handle 101 and tubes 201 of FIG. 1. In some embodiments, two fluid delivery elements 132 are included (e.g. mounted 180° apart on expandable element 131). In some embodiments, three fluid delivery elements 132 are included (e.g. mounted 120° apart on expandable element 131). In some embodiments, four or more fluid delivery elements 132 are included (e.g. four elements mounted 90° apart on expandable element 131). In some embodiments, three or more fluid delivery tubes 137 are attached to expandable element 131 with spacing to accommodate advancement of endoscope 50 proximate to expandable element 131, as is described hereabove in reference to FIGS. 6A and 6B. In some embodiments, a distal portion of one or more shafts 110 further include treatment assembly 160 as shown. Treatment assembly 160 can be positioned distal or proximal (as shown) to expandable assembly 130.

Motion transfer assembly 260 can be configured to rotate treatment assembly 160 and/or expandable assembly 130 independently or in unison. Motion transfer assembly 260 can be configured to translate treatment assembly 160 as treatment is applied to a portion of target tissue TT. In some embodiments, contiguous tissue segments are treated by device 100 continuously as motion transfer assembly 260 causes treatment assembly 160 to translate at a rate of at least 10 cm/minute, or at a rate of least 20 cm/minute. In some embodiments, treatment assembly 160 is manually translated, such as at a rate of at least 10 cm/minute, or at least 20 cm/minute. Motion transfer assembly 260 can be configured to translate treatment assembly 160 between a first tissue treatment and a second tissue treatment. Motion transfer assembly 260 can include one or more rotational and/or linear drive assemblies, such as those including rotational motors, magnetic drives, lead screws and/or other linear actuators, and the like which are operably connected to shaft 110a and/or 110b. Shafts 110a and/or 110b are constructed with sufficient column strength and/or torque transfer properties to adequately rotate and/or translate treatment assembly 160 and/or expandable assembly 130, respectively. Motion transfer assembly 260 can be in communication with controller 210, such as to activate, adjust and/or otherwise control motion transfer assembly 260 and thus the motion of treatment assembly 160 and/or expandable assembly 130. Motion transfer assembly 260 can be manually driven and/or automatically (e.g. motor) driven. Alternatively or additionally, motion transfer assembly 260 can be used to advance and/or retract treatment assembly 160 and/or expandable assembly 130 from a first position to treat a first portion of target tissue, to a second position to treat a second portion of target tissue. In these embodiments, repositioning of treatment assembly 160 and/or expandable assembly 130 can be configured to provide overlapping treatment.

Shafts 110a and 110b can include one or more lumens passing therethrough, and can comprise wires and/or optical fibers for transfer of data and/or energy such as RF energy to a functional element 109. Shafts 110b and/or 110a can comprise one or more shafts, such as one or more concentric shafts configured to deliver and/or recirculate hot and/or cold fluid through expandable assembly 130 and/or treatment assembly 160, respectively. In some embodiments, a heated fluid is used to pre-heat one or more device 100 components and/or to deliver a bolus of hot fluid energy, each as described in applicant's co-pending U.S. patent application Ser. No. 14/470,503, entitled "Heat Ablation Systems, Devices and Methods for the Treatment of Tissue, filed Aug. 27, 2014, the entire content of which is incorporated herein by reference in its entirety. Device 100 can comprise multiple expandable assemblies 130, such as a first expandable assembly positioned proximal to treatment assembly 160 (not shown) and a second expandable assembly positioned distal to treatment assembly 160 (expandable assembly 130 as shown in FIG. 7).

The distal end of shaft 110 (e.g. the distal end of shaft 110b) can comprise a bulbous element, bulbous tip 115. In these embodiments, bulbous tip 115 can be sized to fit through a working channel of endoscope 50, such as when bulbous tip 115 has a diameter less than 6 mm or less than 4 mm. Alternatively, bulbous tip 115 can have a larger diameter, such as a diameter or other geometry configured to assist in smoothly traversing plicae, such as a diameter of at least 8 mm. In some embodiments, bulbous tip 115 comprises a diameter between 4 mm and 9 mm, such as a diameter between 4 mm and 6 mm. In some embodiments, bulbous tip 115 comprises at least a radiopaque portion.

Shafts 110a and 110b of FIG. 7 are sized and configured such that shaft 110a slidingly receives shaft 110b, such that they can be advanced and/or retracted in unison or independently. Differential motion between shafts 110a and 110b can be used to change the distance between expandable assembly 130 and treatment assembly 160. In some embodiments, motion transfer assembly 260 is configured to rotate and/or axially translate shafts 110a and/or 110b such that treatment assembly 160 and/or expandable assembly 130, respectively, are rotated and/or translated. In some embodiments, device 100 comprises a flexible portion (e.g. a portion of shafts 110a and 110b, such as a distal portion of shaft 110b) with a diameter less than 6 mm. In some embodiments, the flexible portion of device 100 is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum and/or jejunum; and/or rectally inserted into a patient, and subsequently advanced to reach the terminal ileum of that patient. In FIG. 7, shafts 110a and 110b have been inserted through a working channel (e.g. a 6 mm working channel), lumen 51, of endoscope 50, typically a GI endoscope. Shafts 110a and/or 110b can be inserted over a standard interventional guidewire, such as guidewire 60 shown exiting the distal end of shaft 110b. In an alternative embodiment, shafts 110a and 110b are positioned in a side-by-side configuration, such as to be placed in two separate lumens of endoscope 50 or in two other non-coaxial locations. In some embodiments, one or both of shafts 110a or 110b passes through a body lumen or other internal body location alongside endoscope 50 (i.e. not through lumen 51, traveling relatively parallel with but external to endoscope 50). Shaft 110a and/or 110b can include a manipulating element constructed and arranged to deflect and/or steer a distal portion of the shaft, such as via one or more proximal handle controlled and/or motion transfer assembly 260 controlled pull wires that extend and are attached to a distal portion of the shaft (handle and pull wires not shown but well known to those of skill in the art), such as to deflect and/or steer treatment assembly 160 and/or expandable assembly 130 towards and/or away from tissue and/or assist in navigating treatment assembly 160 and/or expandable assembly 130 through tortuous anatomy.

Handle 101 can comprise one or more controls included in user interface 105 (such as are described hereabove in reference to user interface 105 of FIG. 1). In some embodiments, user interface 105 comprises one or more controls selected from the group consisting of: electrical control; mechanical control; button; knob; switch; lever; touchscreen; and combinations of these. In some embodiments, a mechanical control is operably attached to a mechanical mechanism, such as a cam or other mechanical advantage mechanism used to transmit a force. In some embodiments, an electrical control is used to attach one or more components of system 10 to power and/or to activate an electrically powered mechanical mechanism such as a solenoid or an electronic valve. User interface 105 can be configured to allow an operator to initiate, regulate, modify, stop and/or otherwise control one or more functions of fluid delivery assembly 200 and/or device 100.

In some embodiments, user interface 105 comprises one or more knobs or other controls used to advance and/or retract one or more fluid delivery elements 132, positioned on expandable element 131 of expandable assembly 130, each described in detail herebelow. In some embodiments, one or more fluid delivery elements 132 are advanced and/or retracted via a force limiting assembly 140. Force limiting assembly 140 can be of similar construction and arrangement to force limiting assembly 140 of FIGS. 1 and 2A and/or force limiting assembly 340 of FIG. 3. Force limiting assembly 140 can be constructed and arranged to allow a single control (e.g. a sliding knob) to advance multiple fluid delivery elements 132 simultaneously, also as described hereabove in reference to FIGS. 1 and 2A. In some embodiments, advancement and/or retraction of one or more fluid delivery elements 132 is limited by one or more mechanical stops, such as are described herein.

In some embodiments, user interface 105 comprises a button, touch screen display and/or other control used to initiate, regulate, modify, stop and/or otherwise control one or more parameters of fluid delivery assembly 200, such as a tissue expanding fluid parameter selected from the group consisting of: flow rate of tissue expanding fluid; duration of tissue expanding fluid flow; volume of tissue expanding fluid; temperature of tissue expanding fluid; pressure of tissue expanding fluid; a tissue expanding fluid threshold parameter level (e.g. maximum or minimum flow rate, duration, volume, temperature and/or pressure); type of tissue expanding fluid; and combinations thereof. In some embodiments, user interface 105 comprises a button, touch screen display and/or other control used to initiate, regulate, modify, stop and/or otherwise control one or more parameters of energy delivery unit 250, such as an ablation parameter selected from the group consisting of: flow rate of ablative fluid; volume of ablative fluid; pressure of ablative fluid; temperature of ablative fluid; type of energy delivered; type of RF energy delivered (e.g. monopolar, bipolar or both); amount of RF energy delivered (e.g. voltage, current and/or power delivered); and combinations of these.

Device 100 of FIG. 7 can include an outer shaft 110*a* and an inner shaft 110*b* (generally shaft 110 or shafts 110). Expandable assembly 130 can be mounted to shaft 110*b*, and an optional treatment assembly 160 can be mounted proximal to expandable assembly 130 on shaft 110*a*. In some embodiments, device 100 comprises a single shaft, and both treatment assembly 160 and expandable assembly 130 are mounted to that single shaft. Expandable assembly 130 is constructed and arranged to deliver fluid, via one or more fluid delivery elements 132, into target tissue TT, such as to expand tissue proximate target tissue TT (e.g. tissue proximate target tissue TT including target tissue TT). In some embodiments, expandable assembly 130 can be configured in one or more various forms to treat, modify, manipulate, measure and/or diagnose target tissue TT and/or other tubular tissue. Expandable assembly 130 can comprise one or more expandable elements 131, such as one or more expandable elements selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 130 is inflatable (e.g. an inflatable balloon), and inflation fluid can be delivered into expandable assembly 130 via an inflation tube 139. Inflation tube 139 can comprise a lumen of shaft 110*b* (or a tube within shaft 110*b*) that travels proximally through shaft 110*b* and shaft 110*a*, such as to receive inflation fluid delivered by inflation source 240. Expandable assembly 130 can be positioned distal to treatment assembly 160 as shown in FIG. 7, or alternatively, expandable assembly 130 can be positioned proximal to treatment assembly 160, such as when treatment assembly 160 is mounted to shaft 110*b* and expandable assembly 130 is mounted to shaft 110*a*.

Treatment assembly 160 can be radially expandable, similar to expandable assembly 130 and/or it can include one or more radially expandable elements, such as those described hereabove in reference to expandable assembly 130 and/or expandable element 131. System 10 can be configured to allow expansion of treatment assembly 160 to cause one or more treatment elements 165 to approach and/or contact a tissue wall such as a duodenal wall, such as when one or more treatment elements 165 comprise a balloon configured to ablate tissue with a contained hot or cold fluid, or when one or more treatment elements 165 comprise an electrode configured to deliver RF energy to ablate tissue. Treatment assembly 160 can be configured to expand to a diameter less than the diameter of the target tissue TT, such as when a vacuum is applied to cause the target tissue TT diameter to decrease sufficiently to make contact with one or more treatment elements 165 (e.g. in a desufflation procedure). System 10 can be configured to allow expansion of treatment assembly 160 to cause one or more treatment elements 165 to be positioned at a fixed distance from the luminal wall of tubular tissue, such as a positioning at a fixed distance of at least 250 microns, at least 500 microns, or at least 1 mm from a tissue wall, such as when one or more treatment elements 165 are configured to deliver ablative fluid to the target tissue TT and/or to deliver light energy to the target tissue TT. In addition to treating target tissue TT, treatment assembly 160 and/or one or more treatment elements 165 can be configured in one or more various forms to modify, manipulate, measure and/or diagnose target tissue TT and/or other tubular or non-tubular tissue. Expansion of treatment assembly 160 can occur prior to, during and/or after treatment of target tissue TT by treatment element 165. Treatment element 165 can be mounted on, within and/or inside of an expandable assembly, such as on, within and/or inside of an expandable balloon. Treatment assembly 160 can be constructed and arranged to expand and contact luminal wall tissue without applying an undesired force to the luminal wall tissue, such as by applying a pressure of less than 2.0 psi or less than 1.2 psi. Treatment assembly 160 can be constructed and arranged to expand to a diameter between 20 mm and 35 mm, such as to a diameter between 20 mm and 27.5 mm Treatment assembly 160 can be constructed and arranged to contact luminal wall tissue with a pressure of at least 0.6 psi.

In some embodiments, expandable assembly 130 and/or treatment assembly 160 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assembly 130 and/or treatment assembly 160 comprise a balloon which is fluidly attached to an inflation tube, such as inflation tube 139 which travels proximally through shaft 110*a* and/or 110*b* and is attached to one or more tubes 201 and/or an inflation port on handle 101.

In some embodiments, expandable assembly 130 is constructed and arranged to exert no more than a maximum threshold force on tissue, such as luminal wall tissue. The threshold force can comprise a force less than 2.0 psi, such as a force less than 1.2 psi. Expandable assembly 130 can be constructed and arranged to contact luminal wall tissue with sufficient force to maintain a pressure of at least 0.6 psi. Expandable assembly 130 can be constructed and arranged to expand to a target diameter, such as a diameter of at least 10 mm, at least 15 mm, at least 25 mm, at least 30 mm or at least 40 mm. In some embodiments, expandable assembly 130 is constructed and arranged to expand to a diameter between 20 mm and 35 mm, such as a diameter between 20 mm and 27.5 mm. In some embodiments, expandable assembly 130 has its diameter controlled by a component of system 10 (e.g. controller 210 and/or inflation source 240), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, expandable assembly 130 is constructed and arranged to expand to its target diameter in less than 60 seconds, such as less than 30 seconds or less than 15 seconds. In other embodiments, expandable assembly 130 is expanded to a target diameter by inflating with fluid delivered at a constant pressure (e.g. approximately 0.7 psi) until the target diameter is reached. In some embodiments, expandable assembly 130 is constructed and arranged to expand to a diameter less than the diameter of the lumen of the GI tract proximate expandable assembly 130. In these embodiments, vacuum can be applied (e.g. gas or other fluid removed via an endoscope 50 or device 100 insufflation port), which brings the tissue of the luminal wall toward a tissue capture port 135 and/or a fluid delivery element 132.

In some embodiments, treatment assembly 160 is constructed and arranged to exert no more than a maximum threshold force on tissue, such as luminal wall tissue. Treatment assembly 160 can be constructed and arranged to treat tissue while maintaining a pressure of at least 0.6 psi. Treatment assembly 160 can be constructed and arranged to expand to a target diameter, such as a diameter of at least 10 mm, at least 15 mm, at least 25 mm, at least 30 mm or at least 40 mm. In some embodiments, treatment assembly 160 is constructed and arranged to expand to a diameter between 20 mm and 35 mm, such as a diameter between 20 mm and 27.5 mm. In some embodiments, treatment assembly 160 has its diameter controlled by a component of system 10 (e.g. controller 210, inflation source 240 and/or EDU 250), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, treatment assembly 160 is constructed and arranged to expand to a diameter less than the diameter of the lumen of the GI tract proximate treatment assembly 160. In these embodiments, vacuum can be applied (e.g. gas or other fluid removed via an endoscope 50 or device 100 insufflation port), which brings the tissue of the luminal wall toward treatment assembly 160 and/or treatment element 165.

In some embodiments, expandable assembly 130 and/or treatment assembly 160 comprise a length of at least 10 mm, such as a length between 10 mm and 40 mm, a length between 15 mm and 30 mm, or a length between 20 mm and 25 mm. In some embodiments, expandable assembly 130 and/or treatment assembly 160 comprise a length less than or equal to 15 mm, such as when configured to treat curvilinear portions of the GI tract. Multiple assemblies positioned on shafts 110a and/or 110b (e.g. between two and twenty treatments and/or expandable assemblies), such as expandable assembly 130 and treatment assembly 160, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and treatment assembly 160 is less than or equal to the expandable assembly 130 length. In these embodiments, treatment assembly 160 can comprise a similar length to that of expandable assembly 130, such as when both expandable assembly 130 and treatment assembly 160 comprise an ablation element as is described herebelow. Treatment assembly 160 and/or expandable assembly 130 can be sized, constructed and/or arranged to expand tissue and/or ablate tissue, or otherwise perform a function, while positioned in a curved segment of the GI tract.

Expandable assembly 130 and/or treatment assembly 160 can be resiliently biased, such as in a radially expanded or radially compacted state. In some embodiments, expandable assembly 130 and/or treatment assembly 160 are expanded and/or compacted by a control shaft, such as control shaft included in conduit 161 or another conduit of device 100 and manipulatable by an operator of system 10 and/or by motion transfer assembly 260. Expandable assembly 130 and/or treatment assembly 160 can be constructed and arranged to achieve a round or non-round shape (e.g. a football shape) when expanded. Expandable assembly 130 and/or treatment assembly 160 can approximate a tubular shape when expanded, such as a relatively constant diameter or varying diameter tubular shape. Expandable assembly 130 can be configured to un-fold to a radially expanded state, or to fold to a radially compacted state.

Expandable assembly 130 and at least one fluid delivery element 132 are configured to expand or otherwise modify tissue, such as to expand one or more layers of tissue. One or more fluid delivery elements 132 can comprise a needle, water jet and/or iontophoretic fluid delivery element configured to deliver injectate 221 into target tissue, such as to expand submucosal or other tissue of the GI tract. Fluid delivery assembly 200 can comprise a reservoir or control means for delivering a pre-determined amount of injectate 221 to tissue by device 100, such as a volume of fluid of at least 1 ml, or a volume of fluid of at least 2 ml, 5 ml, 10 ml or 25 ml. Device 100 can be configured to inject fluid into multiple injection sites (e.g. simultaneously or sequentially), such as a set of multiple injection sites selected from the group consisting of: at least 3 injection sites along a circumference of tubular tissue, a first circumferential injection site separated from a second circumferential injection site by approximately 1 cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements positioned on or near fluid delivery elements 132, such as tissue capture ports 135 shown. Tissue capture ports 135 can be of similar construction and arrangement to tissue capture ports 135 of FIG. 1 described hereabove. Tissue capture ports 135 are configured to apply negative pressure proximate the injection site, such as to capture tissue within the port and avoid the fluid delivery element 132 from having to radially exit tissue capture port 135 to penetrate the tissue. Tissue capture ports 135 can comprise one or more portions that are radiopaque. Fluid delivery assembly 200 and/or tissue capture ports 135 can be configured to discharge or otherwise release tissue from tissue capture port 135, such as by applying a positive pressure to tissue capture port 135. Device 100 can comprise one or more sensors configured to monitor the vacuum level in tissue capture port 135 and/or a fluidly connecting lumen, such as is described in detail hereabove in reference to FIG. 1.

As described hereabove, system 10 can be constructed and arranged to both expand tissue and treat tissue. In some embodiments, one or more devices 100 can be constructed and arranged to both expand tissue and treat tissue, such as via treatment assembly 160. Alternatively or additionally, system 10 can comprise a separate device for tissue treatment, treatment device 500. Device 500 can comprise one or more treatment elements configured to treat target tissue TT, such as a treatment assembly similar to treatment assembly 160 described herein. Fluid delivery assembly 200 can further include an energy delivery unit, EDU 250, which can be operably attached to first device 100 (as shown), second device 100' and/or device 500. EDU 250 can be configured to provide numerous forms of energy to one or more treatment elements of device 100 and/or device 500, such as an energy form selected from the group consisting of: RF energy; microwave energy; laser energy; sound energy such as subsonic sound energy or ultrasound energy; chemical energy; thermal energy such as heat energy or cryogenic energy provided by an ablative fluid; and combinations of these.

In some embodiments, system 10 and/or device 500 can be constructed and arranged as is described in applicant's co-pending U.S. patent application Ser. No. 13/945,138, entitled "Devices and Methods for the Treatment of Tissue", filed Jul. 18, 2013, the entire content of which is incorporated herein by reference in its entirety. In some embodiments, device 100 can be constructed and arranged to ablate tissue with an ablation treatment selected from the group consisting of: delivery of thermal energy from a balloon filled with fluid at an ablative temperature; RF energy ablation such as monopolar and/or bipolar RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations of these. In some embodiments, device 100 and/or device 500 can be constructed and arranged to perform a non-ablative treatment of target tissue, such as with a non-ablative treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. Device 100 and/or device 500 can be constructed and arranged to resect tissue, such as to resect tissue selected from the group consisting of: plicae tissue; mucosal tissue; submucosal tissue; and combinations of these.

One or more components of fluid delivery assembly 200 can include a pump and/or reservoir which can provide and/or remove one or more fluids to and/or from one or more devices of system 10, such as device 100, device 500 and/or endoscope 50. Fluids can be provided (e.g. by EDU 250) to thermally prime (e.g. hot or cold priming) one or more components of system 10, as described in detail herebelow. Tissue ablating fluids can be provided, such as hot or cold ablative fluids provided by EDU 250 to treatment assembly 160 of device 100. Tissue neutralizing fluids can be provided (e.g. by EDU 250) such as cooling fluids provided after elevated temperature ablation or warming fluids provided after cryogenic ablation. Fluids can be provided (e.g. a gas) to insufflate a portion of the GI tract, such as fluids provided through a lumen of endoscope 50 or a lumen of device 100. Fluid delivery assembly 200 can include one or more fluid reservoirs (e.g. one or more reservoirs included in fluid source 220, vacuum source 230, inflation source 240 and/or energy delivery unit 250) constructed and arranged to supply or receive fluids to or from device 100. In some embodiments, fluid delivery assembly 200 includes one or more reservoirs, one or more pumps, and one or more cooling or heating units such that fluid delivery assembly 200 recirculates or otherwise continuously provides one or more hot and/or cold fluids through a device of system 10, such as to recirculate fluid through one or more portions of device 100, device 500 and/or endoscope 50.

Treatment assembly 160 can include one or more elements constructed and arranged to ablate or otherwise treat target tissue TT, such as tissue treatment element 165 shown. Treatment element 165 can comprise one or more elements selected from the group consisting of: a bolus of ablative fluid; recirculating ablative fluid; continuously replenished ablative fluid; an electrical energy delivery element such as one or more electrodes constructed and arranged to deliver RF energy; a fluid delivery element such as a nozzle or permeable surface constructed and arranged to deliver ablative fluid directly in contact with target tissue TT; a balloon such as a balloon constructed and arranged to receive a bolus of ablative fluid and deliver hot or cold thermal energy to ablate target tissue TT; a balloon such as a balloon constructed and arranged to receive a recirculating ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 165 can be positioned on, in, within and/or passing through one or more components of treatment assembly 160, such as a balloon, cage, spline or other component as are described herein. In some embodiments, treatment assembly 160 and treatment element 165 are the same component, such as when treatment assembly 160 comprises a balloon constructed and arranged to receive hot or cold ablative fluid to treat target tissue. Treatment assembly 160 can comprise an energy distribution element, such as one or more optical components configured to rotate, translate and/or otherwise distribute laser or other light energy to target tissue. In some embodiments, treatment assembly 160 and/or treatment element 165 comprise an energy distribution element including a rotating element such a rotating mirror; a rotating prism and/or a rotating diffractive optic. In some embodiments, device 100 comprises one or more fibers that deliver laser or other light energy to a treatment element 165 comprising a balloon filled with light-scattering material.

In some embodiments, device 100 and/or device 500 delivers thermal (e.g. heat or cryogenic) energy to tissue, such as when treatment assembly 160 and/or treatment element 165 comprises a balloon constructed and arranged to be filled with an ablative fluid comprising a hot or cold volume of fluid at a temperature sufficient to ablate tissue when the balloon contacts the tissue. The hot or cold volume of fluid can be provided to treatment assembly 160 and/or treatment element 165 via EDU 250. System 10 can be configured to deliver thermal energy to tissue as is described in applicant's co-pending U.S. patent application Ser. No. 14/470,503, entitled "Heat Ablation Systems, Devices and Methods for the Treatment of Tissue, filed Aug. 27, 2014, or as is described in applicant's co-pending International Patent Application Serial Number PCT/US2014/055514, entitled "Systems, Methods and Devices for Treatment of Target Tissue", filed Sep. 12, 2104, the entire contents of each of which is incorporated herein by reference in their entirety.

In some embodiments, device 100 and/or device 500 delivers RF energy to tissue, such as when treatment element 165 comprises one or more electrodes constructed and arranged to receive RF energy provided by EDU 250. In these embodiments, the one or more electrodes can comprise one or more conductive dots or other conductive elements positioned on an expandable element such as a balloon. In some embodiments, EDU 250 is configured to deliver RF energy to one or more electrodes of device 100 and/or device 500, such as in a monopolar mode through a grounding pad such as ground pad 70 and/or in a bipolar mode between two or more electrodes of device 100 or device 500. System 10 can be configured to deliver RF energy to tissue as is described in applicant's co-pending U.S. patent application Ser. No. 14/609,332, entitled "Electrical Energy Ablation Systems, Devices and Methods for the Treatment of Tissue", filed Jan. 29, 2015, the entire content of which is incorporated herein by reference in its entirety.

In some embodiments, device 100 and/or device 500 delivers ablative fluid directly to tissue, such as when treatment element 165 comprises one or more ablative fluid delivery elements. In these embodiments, treatment element 165 can be constructed and arranged to ablate target tissue TT by delivering ablative fluid provided by EDU 250. Treatment element 165 can include one or more fluid delivery elements selected from the group consisting of: nozzle such as a nozzle configured to deliver a cone or other shaped spray of fluid; needle; opening; hole; slit; permeable membrane; misting element; vaporizer; and combinations of these. Ablative fluid can comprise one or more liquids or gases that are delivered to target tissue TT at a temperature above or below a threshold that would ablate tissue. In some embodiments, the ablative fluid delivered by treatment element 165 comprises steam, such as steam at a temperature of 100° C. or above. In some embodiments, the ablative fluid delivered by treatment element 165 comprises a vaporized fluid at a temperature below 100° C., such as a vaporized fluid at a temperature between 70° C. and 90° C. In some embodiments, the ablative fluid delivered by treatment element 165 comprises a gas, such as a gas between 60° C. and 99° C., such as a gas delivered to tissue at a temperature between 70° C. and 90° C. In some embodiments, the ablative fluid delivered by treatment element 165 comprises a vaporized liquid, such as a vaporized liquid delivered to tissue at a temperature below 100° C., such as at a temperature between 70° C. and 90° C. Alternatively or additionally, an ablative fluid delivered by treatment element 165 can comprise one or more liquids or gases that cause tissue necrosis or otherwise treat target tissue TT using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting agent can be included, such as a counter-acting agent delivered by device 100 or another device or component of system 10 that is used to neutralize, impede, reduce and/or limit tissue ablation caused by the delivery of a necrotic agent-based ablative fluid. The counter-acting agent can be delivered by treatment element 165 or another component of device 100 or system 10. The counter-acting agent can comprise an agent selected from the group consisting of: anti-sclerotic agent; base; acid; buffer solution; saline; water; and combinations of these. System 10 can be configured to deliver ablative fluid directly to tissue as is described in applicant's co-pending U.S. patent application Ser. No. 14/609,334, entitled "Ablation Systems, Devices and Methods for the Treatment of Tissue", filed Jan. 29, 2015, the entire content of which is incorporated herein by reference in its entirety.

Treatment assembly 160 can be positioned on shaft 110a as shown. Treatment element 165 is electrically, fluidly, mechanically and/or otherwise operably connected to conduit 161. Conduit 161 comprises one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery or a vacuum supplying tube; a lumen such as a fluid delivery lumen or a vacuum supplying lumen; a control rod such as an advanceable and/or retractable control rod; and combinations of these. Conduit 161 travels proximally through shaft 110a and operably attaches to fluid delivery assembly 200, such as to operably attach to one or more of: fluid source 220; vacuum source 230; inflation source 240; EDU 250; motion transfer assembly 260; and/or combinations of these, and/or to attach to another component, assembly or device of system 10. In some embodiments, one or more portions (e.g. one or more filaments) of conduit 161 extend to expandable assembly, such as one or more filaments selected from the group consisting of: a control rod; an inflation tube; an inflation lumen; a fluid delivery tube; a wire; an optical fiber; and combinations of these.

In some embodiments, conduit 161 comprises one or more fluid delivery tubes and/or lumens constructed and arranged to deliver and/or recirculate heated or chilled fluid into treatment assembly 160, such as heated or chilled fluid received from EDU 250 and delivered into treatment element 165, such as when treatment element 165 comprises a balloon or other fluid reservoir configured to receive ablative fluid at a temperature sufficient to ablate tissue when treatment element 165 contacts the tissue. Alternatively or additionally, conduit 161 can comprise one or more fluid delivery tubes constructed and arranged to deliver an ablative fluid to treatment assembly 160, such as ablative fluid provided by EDU 250 and delivered directly to target tissue TT by one or more treatment elements 165, such as when treatment element 165 comprises a fluid delivery element such as a nozzle. Conduit 161 can further comprise one or more insulating layers configured to prevent transfer of heat into and/or out of conduit 161. Conduit 161 can include a surrounding lumen which receives a circulating fluid configured to provide an insulating, warming and/or cooling effect on conduit 161 and/or any fluid contained within conduit 161. Conduit 161 and/or another fluid delivery tube of system 10 can comprise one or more elongate hollow tubes, such as a hollow tube positioned within shaft 110a. Alternatively, conduit 161 and/or another fluid delivery tube of system 10 can comprise a lumen within a shaft, such as a lumen within shaft 110a. In some embodiments, conduit 161 and/or another fluid delivery tube of system 10 comprises both a lumen and a hollow tube, such as when the lumen and hollow tube are fluidly connected in an end-to-end configuration. Conduit 161 typically attaches to fluid delivery assembly 200 with one or more operator attachable fluid connection ports (e.g. attaching to tubes 201), such as a fluid connection port included in handle 101 positioned on the proximal end of shaft 110a. Conduit 161 can comprise one or more fluid delivery tubes including one or more valves, not shown but such as a duck-bill or other valve used to regulate flow within conduit 161, such as to regulate flow pressure and/or direction.

In some embodiments, conduit 161 comprises one or more elongate filaments constructed and arranged to transmit energy and/or data. Conduit 161 can comprise one or more wires constructed and arranged to deliver RF energy to one or more electrode-type treatment elements 165, such as when the treatment elements 165 are configured to ablate target tissue TT in monopolar and/or bipolar modes as described herein. Conduit 161 can comprise one or more filaments constructed and arranged to deliver laser energy, such as one or more optical fibers constructed and arranged to deliver laser energy to one or more lenses or other optical component-type treatment elements 165, such as to ablate target tissue TT with laser or other light energy. Conduit 161 can comprise one or more wires or other energy transfer filaments constructed and arranged to allow a sound producing-type treatment element to ablate target tissue TT with sound energy such as ultrasonic or subsonic sound energy. Conduit 161 can comprise one or more wires or optical fibers configured to transmit information, such as information received from a sensor of system 10 as described herebelow.

In some embodiments, conduit 161 comprises one or more control rods constructed and arranged to cause one or more treatment elements 165 and/or fluid delivery elements 132 to rotate and/or translate, such as when conduit 161 is operably attached to motion transfer assembly 260, such as prior to, during and/or after expansion of a tissue layer and/or delivery of energy to target tissue. In some embodiments, one or more treatment elements 165 comprise a surface configured to abrade or otherwise disrupt tissue as it is rotated and/or translated by movement of conduit 161. Alternatively or additionally, one or more fluid delivery elements 132 and/or treatment elements 165 can deliver energy and/or fluid to tissue, and movement of one or more control rods of conduit 161 changes the location of the tissue segment receiving the energy and/or fluid. Motion of one or more fluid delivery elements 132 and/or treatment elements 165 can be configured to expand and/or treat a full circumferential (i.e. 360°) segment of tubular tissue, or a partial circumferential (e.g. 45°-350° segment of tubular tissue. Motion of one or more treatment elements 165 can be configured to expand and/or treat a particular axial length of tubular tissue, such as an axial length comprising at least 25% of the axial length of the duodenum, or at least 35% of the axial length of the duodenum, or at least 50% of the axial length of the duodenum, or at least 66% of the axial length of the duodenum; or at least 75% of the axial length of the duodenum.

EDU 250 can comprise multiple heat or cold sources used to modify the temperature of one or more fluids provided by and/or passing through EDU 250, fluid delivery assembly 200, device 100 and/or device 500. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after a heat ablation treatment of target tissue TT, such as to precisely control target tissue ablation and avoid ablation of non-target tissue. The cooling fluid can be provided by EDU 250 or another component of fluid delivery assembly 200, and it can be delivered to tissue, such as target or non-target tissue, and/or it can be delivered to a component of system 10 such as to reduce the temperature of a component of treatment assembly 160 or a component of device 500. Treatment element 165, fluid delivery element 132 and/or another component of system 10 can be constructed and arranged to deliver the cooling fluid to one or more tissue surfaces, such as a cooling fluid delivered to treatment element 165 via conduit 161 and configured to reduce the temperature of one or more volumes of tissue. In some embodiments, system 10 is configured to deliver fluid at a sufficiently high temperature to ablate target tissue TT, after which a cooling fluid is automatically and/or semi-automatically delivered to remove thermal energy from target tissue TT and/or other tissue, such as cooling fluid delivered for a time period of at least 2 seconds, at least 5 seconds, at least 10 seconds or at least 20 seconds.

Ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat overlapping portions of target tissue TT, and/or to avoid creation of tissue debris if desired. Desiccating ablations can be performed to achieve a higher thermal gradient, to remove excess tissue, and/or to ablate rapidly if desired. Fluid delivery assembly 200, treatment element 165 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 250 can be configured to deliver a hot fluid to thermally prime (i.e. pre-heat or pre-chill) one or more components of system 10. In some embodiments, the one or more components include conduit 161; a fluid delivery tube such as a tube within shaft 110a, a fluid delivery lumen such as a lumen within shaft 110a; shaft 110b; fluid delivery element 132; treatment element 165; and combinations of these. System 10 can be configured to thermally prime one or more components by circulating or recirculating hot fluid (pre-heat) or cold fluid (pre-chill), such as a hot or cold liquid or gas. In some embodiments, treatment assembly 160 contains and/or treatment element 165 delivers a hot fluid, and one or more components of system 10 are pre-treated with a hot gas. Alternatively or additionally, system 10 can comprise one or more insulators surrounding one or more conduits, lumens and/or shafts of device 100 and/or system 10, such as an insulator surrounding conduit 161 and configured to prevent transfer of heat across (e.g. into or out of) conduit 161.

Fluid delivery assembly 200, treatment element 165 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 250) such that tissue temperature decreases over time, such as to match a tissue response of the target tissue TT.

System 10 can be configured to maintain target tissue TT or other tissue under a threshold (e.g. below a maximum temperature of a heat ablation or above a minimum temperature of a cryogenic ablation) and/or within a temperature range, such as in a closed-loop configuration through the use of one or more sensors such as functional element 109 of treatment assembly 160 or functional element 109 of expandable assembly 130, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment element 165 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 250 is configured to heat or chill one or more fluids, such as one or more ablative fluids provided by EDU 250, or other fluids. In some embodiments, treatment assembly 160 is configured to heat or chill one or more fluids, such as when functional element 109 comprises a heating and/or cooling element. Applicable heating and cooling elements include but are not limited to heat exchangers, heating coils, peltier components, refrigeration assemblies, gas expansion coolers, and the like. Heating and cooling can be applied to a source of fluid (e.g. a reservoir of fluid delivery assembly 200), or to fluid that is withdrawn from device 100 (e.g. a recirculating fluid and/or a body extracted fluid such as recovered, previously delivered, ablative or insufflating fluid). EDU 250 can include one or more pumps configured to deliver and/or extract fluid at a particular flow rate, pressure, or other fluid delivery parameter.

Expandable assembly 130 and/or treatment assembly 160 can be configured to seal a body lumen location, such as to create a full or partial occlusive barrier at a location within the duodenum or other location in the GI tract. System 10 can be configured to cause a fluid or other seal comprising an occlusive barrier selected from the group consisting of: a pressure seal; a cryogenically applied seal such as an ice ball seal; a vacuum seal; a full circumferential seal; a partial circumferential seal; and combinations of these. In some embodiments, treatment element 165 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 165 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 165, via one or more functional elements 109 (e.g. functional elements 109 of expandable assembly 130 and/or treatment assembly 160, as described in detail herebelow) and/or by another device or component of system 10. Applied vacuum can be used to modify (e.g. change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the GI tract. Deployed balloons or other occlusive elements of system 10 can be positioned to protect tissue, such as to protect the ampulla of Vater and/or the pylorus from adverse effects that can be caused by treatment of target tissue TT by treatment element 165.

Expandable assembly 130 can comprise at least one functional element 109, and treatment assembly 160 can comprise at least one functional element 109. Functional elements 109 can be elements selected from the group consisting of: a sensor; a transducer; an ablation element such as one or more electrodes configured to deliver electrical energy such as radiofrequency (RF) energy; a fluid delivery element such as a needle, a fluid jet, a permeable membrane and/or an exit port; a heating element; a cooling element; and combinations of these.

In some embodiments, expandable assembly 130 is configured to ablate tissue, such as via functional element 109. Functional element 109 of expandable assembly 130 can comprise one or more ablation elements, such as those described herein. In some embodiments, functional element 109 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 or treatment assembly 160 can be used to ablate target tissue TT. EDU 250 or another component of system 10 can be configured to deliver RF or other energy to any functional element 109. System 10 can include ground pad 70, such as a standard RF energy delivery ground pad typically placed on the patient's back, such that EDU 250 can supply RF energy to a functional element 109 and/or any other electrodes of system 10 in monopolar, bipolar and/or combined monopolar-bipolar energy delivery modes.

In some embodiments, functional element 109 of expandable assembly 130 and/or treatment assembly 160 comprises an abrasive element configured for abrading target tissue, such as an abrasive element attached to a balloon or expandable cage.

In some embodiments, expandable assembly 130 is further configured to perform at least one non-tissue expanding function. In some embodiments, expandable assembly 130 is configured to ablate tissue, as described hereabove. Alternatively or additionally, expandable assembly 130 can be configured to occlude or partially occlude a lumen surrounded by tissue (as described hereabove), such as a lumen of the GI tract to be occluded during an insufflation procedure, also as described hereabove. Expandable assembly 130 can be configured to manipulate tissue, such as to linearize and/or distend GI tissue by frictionally engaging (e.g. when expanded) and applying forces to the tissue (e.g. by advancing and/or retracting shaft 110b). In some embodiments, one or more expandable assemblies 130 can perform a function selected from the group consisting of: linearizing curvilinear tissue; distending tissue; expanding tissue; occluding a body lumen; and combinations of these. Expandable assembly 130 can be configured to test and/or diagnose tissue, such as when expandable assembly 130 is used to measure a diameter of tubular tissue into which it has been inserted. Diameter measurements can be performed in various ways, including but not limited to: injection of a radiopaque fluid into expandable assembly 130 and fluoroscopic measurement of the injected fluid; controlled inflation of expandable assembly 130 to a pressure whose level corresponds to a luminal diameter; and combinations of these. In some embodiments, device 100 includes an expandable assembly that can be expanded with one or more control rods (e.g. one or more control rods of conduit 161), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device, such as sizing device 430 described in detail hereinbelow, used to perform a diameter measurement. One or more energy delivery or other ablation parameters can be adjusted based on the measured diameter of target tissue TT and/or a target tissue segment.

Treatment element 165 can be configured to treat various thicknesses of GI tissue, such as at least the innermost 500 microns of duodenal tissue, or at least the innermost 1 mm of duodenal tissue. In some embodiments, treatment element 165 can be configured to ablate or otherwise treat a thickness of at least 600 microns, at least 1 mm or at least 1.25 mm, such as when treating the mucosa of the stomach. Treatment element 165 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or treatment assembly 160 are configured to be in a relatively rigid state, such as during treatment of target tissue TT.

Treatment element 165 and/or other treatment elements of the present inventive concepts can be arranged in an array of elements, such as a circumferential or linear array of elements. The circumferential array can comprise a partial circumferential array of treatment elements 165, such as an array covering approximately 45° to 300° of circumferential area. Partial circumferential arrays of treatment elements 165 can treat a first target tissue segment and a second target tissue segment in two sequential steps, where the array is rotated between treatments (e.g. energy deliveries). The circumferential array can comprise a full 360° array of treatment elements 165, such that a full circumferential volume of target tissue TT can be treated in single or multiple treatments (e.g. energy deliveries) that do not require repositioning of treatment assembly 160. In some embodiments, less than 360° of tubular tissue is treated, such as by treating a circumferential portion of tissue comprising less than or equal to a 350°, or between 300° and 350°, such as to prevent a full circumferential scar from being created.

Two or more treatment elements 165 can be arranged in a helical array. In some embodiments, at least three, four or five treatment elements independently treat target tissue, in similar or dissimilar treatments (e.g. similar or dissimilar amounts of energy, provided simultaneously and/or sequentially by EDU 250).

In some embodiments, fluid delivery assembly 200, EDU 250 and/or another device or component of system 10 provides electrical or other energy to a component of device 100, such as electrical energy provided to a heating coil in a distal portion of device 100, now shown but typically connected to one or more wires of conduit 161 that travel proximally through shaft 110a to handle 101. Fluid delivery assembly 200, EDU 250 and/or another device or component of system 10 can provide energy such as electrical energy to one or more functional elements 109 such as when a functional element 109 comprises a transducer or other powered component.

In some embodiments, treatment element 165 comprises one or more treatment elements that are constructed and arranged to treat the entire amount of tissue to be treated ("desired treatment area") with a single energy delivery and/or at least without having to reposition device 100. In these embodiments, treatment element 165 can comprise an array of treatment elements positioned along substantially the entire desired treatment area of the target tissue, or treatment element 165 can comprise one or more treatment elements configured to rotate and/or translate along substantially the entire desired treatment area of tissue. Treatment element 165 and/or other tissue treatment elements of the present inventive concepts can be configured to treat at least 25% of the desired treatment area of the duodenum simultaneously and/or without having to reposition device 100. Alternatively, treatment element 165 and/or other ablation elements of the present inventive concepts can be configured to treat a first portion of the desired treatment area followed by a second portion of the desired treatment area. The first and second treated tissue segments can be overlapping and they can have non-parallel central axes (e.g. tissue segments in a curved portion of the duodenum). Three or more target tissue segments can be treated, such as to cumulatively ablate at least 25% or at least 50% of the duodenal mucosa.

System 10 can be configured to ablate or otherwise treat target tissue TT, such as duodenal mucosal tissue, while avoiding damaging non-target tissue, such as the GI adventitia. Target tissue TT can include at least a portion of safety-margin tissue comprising tissue whose ablation causes minimal or no adverse effect to the patient, such as sub-mucosal tissue of the GI tract. Target tissue TT can comprise one or more portions of tissue that are treated simultaneously or sequentially. In some embodiments, the target tissue TT comprises at least 25% or at least 50% of the duodenal mucosa. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 50 can be a standard endoscope, such as a standard GI endoscope, or a customized endoscope, such as an endoscope including sensor 53 configured to provide information related to the tissue expansion and/or tissue treatment of the present inventive concepts. Endoscope 50 can include camera 52, such as a visible light, ultrasound and/or other visualization device used by the operator of system 10 prior to, during and/or after the expansion and/or treatment of target tissue TT, such as during insertion and/or removal of endoscope 50 and/or shafts 110a and 110b of device 100. Camera 52 can provide direct visualization of internal body spaces and tissue, such as the internal organs of the GI tract. Endoscope 50 can be coupled with or otherwise include a guidewire, e.g. guidewire 60, such as to allow insertion of endoscope 50 into the jejunum and/or advancement of device 100. Device 100 can be constructed and arranged such that endoscope 50 can be advanced within 5 cm of treatment assembly 160 and/or expandable assembly 130, such as is described hereabove in reference to FIGS. 6A and 6B.

System 10 can be constructed and arranged to perform insufflation of a body lumen, such as insufflation of a segment of the GI tract. The body lumen can be pressurized, such as by using one or more standard insufflation techniques. Insufflation fluid can be introduced through second lumen 54 of endoscope 50. Second lumen 54 travels proximally and connects to a source of insufflation liquid and/or gas, such as fluid delivery assembly 200, and typically a source of air, carbon dioxide, water and/or saline. Alternatively or additionally, insufflation fluid can be delivered by device 100, such as through shaft 110a and/or 110b, and/or through a port in expandable assembly 130 and/or treatment assembly 160, such as when an associated functional element 109 comprises a fluid delivery port attached to a source of insufflation liquid and/or gas (e.g. provided by fluid delivery assembly 200). Alternatively or additionally, a separate device configured to be inserted through endoscope 50 and/or to be positioned alongside endoscope 50, can have one or more lumens configured to deliver the insufflation fluid. System 10 can include one or more occlusive elements and/or devices, such as expandable assembly 130, treatment assembly 160 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Fluid delivery assembly 200 can be configured to remove fluid from a body lumen such as a segment of the GI tract. Removed fluids include but are not limited to: tissue expansion fluid; ablative fluid; condensate of delivered ablative fluid; insufflation fluids; excess bodily fluids; chyme; digestive fluids; gas; and combinations of these. Fluids can be removed prior to, during and/or after expansion of target tissue TT by one or more fluid delivery elements 132 and/or treatment of target tissue TT by treatment element 165. Treatment element 165, fluid delivery element 132 and/or a functional element 109 can be constructed and arranged to remove fluid from a body lumen. Fluid delivery assembly 200 can be configured to apply a vacuum (e.g. suction), such as to remove fluid via at least one treatment element 165, fluid delivery element 132, an outflow drain, or other fluid extraction port of system 10. In some embodiments, extracted fluids are recycled, such as for subsequent delivery by at least one treatment element 165 to target tissue TT.

Fluid delivery assembly 200 can be configured to deliver one or more gases (e.g. carbon dioxide, nitrogen, nitrous oxide and/or air) to at least one treatment element 165, fluid delivery element 132 and/or another gas delivering component of system 10. In some embodiments, at least one treatment element 165 and/or fluid delivery element 132 comprises a gas jet nozzle configured to deliver gas to target tissue, such as a gas than has been processed to remove moisture or otherwise is relatively dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver relatively dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or equal to 10 seconds, or less than or equal to 5 seconds. In some embodiments, system 10 is configured to deliver gas at a temperature at or above 42° C., such as to remove moisture or otherwise dry a tissue wall of the GI tract. System 10 can be configured to deliver carbon dioxide gas.

Functional elements 109 can comprise a sensor. In some embodiments, functional element 109, sensor 53 and/or another sensor of system 10, such as functional element 109 positioned on expandable assembly 130 and/or functional element 109 positioned on treatment assembly 160, can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The sensors can be configured to provide information to one or more components of system 10, such as to controller 210 and/or fluid delivery assembly 200, such as to monitor the expansion and/or treatment of target tissue TT and/or to expand and/or treat target tissue TT in a closed loop configuration. Fluid delivery by fluid source 220 and/or energy delivery from EDU 250 can be initiated, regulated, modified, stopped and/or otherwise controlled based on one or more sensor readings.

Controller 210 can comprise one or more algorithms 211, which can be constructed and arranged to automatically and/or manually control and/or monitor one or more devices, assemblies and/or components of system 10. Algorithm 211 of controller 210 can be configured to determine one or more tissue expansion and/or tissue treatment parameters. In some embodiments, algorithm 211 processes one or more functional element 109 sensor signals to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; and/or temperature of ablative fluid or energy delivered. Treatment assembly 160 can deliver energy to a surface of tissue, an "energy delivery zone", which is a subset of the target tissue TT treated by that energy delivery (i.e. due to the conduction of heat or other energy to neighboring tissue). Algorithm 211 can comprise an algorithm configured to determine an energy delivery zone parameter such as an energy delivery zone parameter selected from the group consisting of: anatomical location of an energy delivery zone; size of energy delivery zone; percentage of energy delivery zone to receive energy; type of energy to be delivered to an energy delivery zone; amount of energy to be delivered to an energy delivery zone; and combinations of these. Information regarding the energy delivery zone parameter can be provided to an operator of system 10. This information can be employed to set an energy delivery zone parameter, assist the operator in determining the completion status of the procedure (e.g. determining when the procedure is sufficiently complete) and/or to advise the operator to continue to complete a pre-specified area or volume of target tissue. The total area of treatment or number of energy delivery zones or number of treatments during a particular procedure (any of which can be employed in algorithm 211) can be defined by patient clinical or demographic data.

Functional elements 109, such as functional element 109 of treatment assembly 160, can comprise a gravimetric sensor. In these embodiments, functional element 109 can comprise an accelerometer or other sensor configured to provide a signal representing the orientation of treatment assembly 160 and/or treatment element 165 as it relates to the force of earth's gravity. In embodiments in which treatment element 165 delivers ablative fluid to target tissue TT, the signal provided by functional element 109 can provide information for manual and/or automated control of ablative fluid delivery direction. In some embodiments, gravimetric orientation of device 100 is provided to an operator, such as via a screen on user interface 205 of fluid delivery assembly 200 and/or user interface 105 of handle 101. In some embodiments, the signal from functional element 109 is recorded by controller 210, such as to adjust a spray pattern delivered by treatment assembly 160 and/or treatment element 165, such as via algorithm 211. Based on a signal from functional element 109, treatment element 165 and/or shaft 110a can be positioned to deliver ablative fluid in upward and/or side-ways (i.e. horizontal) directions, such as to allow delivered fluid to flow across the walls of a lumen in a downward direction. Controller 210 and/or algorithm 211 can be configured to adjust the flow pattern of ablative fluid delivery by adjusting the rotation and/or translation of treatment assembly 160 (e.g. by creating an asymmetric movement). Controller 210 can be configured to adjust the flow pattern of ablative fluid delivery by adjusting which of multiple treatment elements 165 deliver ablative fluid (e.g. by turning on one or more electronic fluid valves) or by adjusting a nozzle direction or nozzle flow path geometry of treatment element 165 (e.g. when treatment element 165 comprises a rotatable nozzle and/or a nozzle with an adjustable orifice). In some embodiments, controller 210 utilizes a signal from functional element 109 to manipulate one or more treatment elements 165 to deliver fluid in a relatively upward direction. In some embodiments, system 10 includes a fluid removal element as described hereabove, such as a treatment element 165 configured to remove fluid by an outflow drain, and the fluid removal element is gravimetrically oriented by a signal provided by functional element 109.

Functional elements 109 can comprise a chemical detection sensor, such as a chemical detection sensor to confirm proper apposition of expandable assembly 130 and/or treatment assembly 160. In this configuration, a chemical sensor such as a carbon dioxide sensor can be placed distal to expandable assembly 130 and/or treatment assembly 160, and a fluid such as carbon dioxide gas can be introduced proximal to the expandable assembly 130 and/or treatment assembly 160. Detection of the introduced fluid by a functional element 109 can indicate inadequate apposition of expandable assembly 130 and/or treatment assembly 160, respectively. Readjustment to achieve sufficient apposition can prevent inadequate expansion and/or treatment of target tissue TT (e.g. inadequate delivery of fluid and/or inadequate transfer of energy) and/or prevent inadequate measurement, modification, manipulation and/or diagnosis of target tissue TT.

Functional elements 109, sensor 53 and/or another sensor of system 10 can be a sensor configured to provide information related to the tissue treatment and/or expansion performed by treatment assembly 160 and/or expandable assembly 130, respectively, such as a visual sensor mounted to treatment assembly 160 and/or expandable assembly 130 that is configured to differentiate tissue types that are proximate treatment assembly 160 and/or expandable assembly 130. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 250 is based on one or more signals from the visible sensor, such as a sensor providing a signal correlating to tissue color wherein the energy delivered is modified based on a tissue color change and/or tissue expansion injectate 221 comprise a visible dye or other visualizable marker used to assess tissue expansion.

One or more functional elements 109 can comprise a temperature sensor configured to monitor the temperature of treatment provided by treatment assembly 160 and/or expandable assembly 130 and/or tissue proximate treatment assembly 160 and/or expandable assembly 130. Functional elements 109 can each comprise multiple temperature sensors, such as multiple temperature sensors positioned on treatment assembly 160 and/or expandable assembly 130, respectively, with a spacing of at least one sensor per square centimeter. Energy delivered by EDU 250 can be based on signals recorded by the multiple temperature sensors.

Fluid delivered by fluid source 220 (e.g. injectate 221) can be based on signals recorded by one or functional elements 109. One or more functional elements 109 can comprise one or more sensors, such as one or more of: a visual sensor such as a camera; a temperature sensor; a pH sensor; an ultrasound transducer; and combinations of these. In some embodiments, injectate 221 comprises one or more dyes (e.g. visible dye, ultrasonically reflective material and/or radiopaque dye), and functional element 109 comprises one or more cameras (e.g. visible light camera, ultrasound imager and/or x-ray camera) that image the tissue being expanded and produce a signal correlating to the amount of tissue expansion based on the amount of dye present in the expanded tissue. In some embodiments, injectate 221 is delivered at a temperature different than the temperature of the tissue being expanded (e.g. above or below body temperature), and functional element 109 comprises a sensor that measures the temperature proximate the tissue being expanded and produces a signal correlating to the amount of tissue expansion based on the measured temperature (e.g. based on the difference between the measured temperature and body temperature). In some embodiments, injectate 221 comprises a pH different than the pH of the tissue being expanded, and functional element 109 comprises a sensor that measures the pH proximate the tissue being expanded and produces a signal correlating to the amount of tissue expansion based on the measured pH (e.g. based on a change in the measured pH that occurs during tissue expansion). In some embodiments, functional element 109 comprises an ultrasound transducer directed at the tissue being expanded and produces a signal correlating to the amount of tissue expansion based on an analysis of an image of the expanding tissue produced by the ultrasound transducer.

A functional element 109 can comprise a transducer. In these and other embodiments, functional element 109 and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; and combinations of these.

In some embodiments, fluid delivery assembly 200 and/or another device of component of system 10 is configured to deliver a visualizable material, such as when injectate 221 and/or another fluid of system 10 includes a visualizable material delivered to one or more fluid delivery elements 132 and/or one or more treatment elements 165. In some embodiments, visualizable material is delivered by fluid delivery element 132 onto and/or beneath the surface of tissue, to assist in the tissue expansion of target tissue TT, such as to assess the status of tissue expansion as described hereabove. In some embodiments, visualizable material is delivered by treatment element 165 onto and/or beneath the surface of tissue, to assist in the treatment of target tissue TT, such as to assess the status of tissue ablation, such as via a camera-based functional element 109. In some embodiments, the visualizable material is selected from the group consisting of; colored dye; radiopaque agent; ultrasonically visible material; magnetically visible material; and combinations of these. An imaging device of system 10, such as a camera based functional element 109 and/or imaging device 410 described herebelow, can be used to create an image of the visualizable material during and/or after delivery of the visualizable material.

In some embodiments, fluid delivery assembly 200 or another device of component of system 10 is configured to deliver abrasive particles, such as abrasive particles delivered to one or more treatment elements 165 and/or fluid delivery elements 132. In some embodiments, visualizable material is also delivered by fluid delivery assembly 200 to assist in the treatment of tissue, such as to improve cellular disruption caused by a mechanical abrasion treatment by visualizing the treatment in real time.

In some embodiments, EDU 250 is configured to deliver at least RF energy, and system 10 includes ground pad 70 configured to be attached to the patient (e.g. on the back of the patient), such that RF energy can be delivered in monopolar delivery mode to one or more electrode-based treatment elements 165 of device 100 or to one or more electrodes of another device of system 10 (e.g. second device 100' and/or device 500). Alternatively or additionally, EDU 250 can be configured to deliver energy in a bipolar RF mode, such as bipolar energy delivered between any two electrode-based treatment elements 165 of device 100 or between any other two electrodes of another treatment device of system 10. Alternatively or additionally, EDU 250 can be configured to deliver energy in a combined monopolar-bipolar mode.

EDU 250 can be configured to deliver RF and/or other forms of energy to one or more treatment elements 165 of treatment assembly 160 and/or a treatment element expandable assembly 130. In some embodiments, EDU 250 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 250, such as in a closed loop fashion based on one or more signals provided by a sensor-based functional element 109. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment.

As described hereabove, fluid delivery assembly 200 typically includes one or more fluid pumps, such as one or more peristaltic, displacement and/or other fluid pumps; as well as one or more heat exchangers and/or other fluid heating elements internal and/or external to device 100. EDU 250 and/or another component of fluid delivery assembly 200 or system 10 can be configured to rapidly deliver and/or withdraw fluid to and/or from treatment assembly 160 and/or expandable assembly 130 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, fluid delivery assembly 200 is configured to deliver fluid, such as a liquid, at a flow rate of at least 500 ml/min, or at least 750 ml/min A pump and/or vacuum source can be configured to continuously exchange hot fluid and/or to perform a negative pressure priming event to remove fluid from one or more fluid pathways of device 100. Fluid delivery assembly 200, device 100 and/or device 500 can include one or more valves in the fluid delivery and/or fluid withdrawal pathways or one or more other valves in the fluid pathway within treatment assembly 160 and/or expandable assembly 130. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Fluid delivery assembly 200 can be configured to rapidly inflate and/or deflate treatment assembly 160 and/or expandable assembly 130. Fluid delivery assembly 200 can be configured to purge the fluid pathways of device 100 and/or device 500 with a gas such as air, such as to remove cold and/or hot fluid from the devices and/or to remove gas bubbles from the devices.

User interface 205 of fluid delivery assembly 200 and/or user interface 105 of handle 101 can include a graphical user interface configured to allow one or more operators of system 10 to perform one or more functions such as entering of one or more system input parameters and visualizing and/or recording of one or more system output parameters. User interface 205 and/or user interface 105 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: volume of tissue expanding fluid to be delivered; flow rate of tissue expanding fluid; temperature of tissue expanding fluid; type of tissue expanding fluid to be delivered; temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Fluid delivery assembly 200, device 100 and/or one or more other components of system 10 can include an electronics module (e.g. similar to electronics module 107 of FIG. 1), such as an electronics module including a processor, memory, software, and the like. User interface 205 and/or user interface 105 are typically configured to allow an operator to initiate, regulate, modify, stop and/or otherwise control expansion and/or treatment of target tissue TT by the various components of system 10, such as by controlling fluid source 220 and/or EDU 250. User interface 205 and/or user interface 105 can be configured to modify one or more tissue treatment parameters, such as a parameter selected from the group consisting of: volume of tissue expanding fluid to be delivered; flow rate of tissue expanding fluid; temperature of tissue expanding fluid; type of tissue expanding fluid to be delivered; temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. System 10 can be configured for manual control, so that the operator first initiates the tissue treatment, then allows the treatment element 165 and/or another associated treatment element to treat the target tissue TT for some time period, after which the operator terminates the treatment.

System 10 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is configured to perform hot fluid ablation, controller 210 can be configured to adjust the temperature, flow rate and/or pressure of fluid delivered to an expandable reservoir, such as when treatment assembly 160 and/or expandable assembly 130 comprise a balloon. Controller 210 can be configured to receive commands from user interface 205 or user interface 105 of device 100. In some embodiments, controller 210 receives wireless (e.g. Bluetooth) commands from user device 100 via user interface 105. Controller 210 can be configured to initiate insufflation and/or to adjust insufflation pressure. Controller 210 can be configured to deliver energy or otherwise treat target tissue in a closed-loop fashion, such as by modifying one or more tissue treatment parameters based on signals from one or more sensors of system 10, such as those described hereabove. Controller 210 can be programmable such as to allow an operator to store predetermined system settings for future use. Controller 210 can comprise memory configured to store one or more system or patient parameters.

Controller 210 can comprise an impedance monitoring assembly, such as an impedance monitoring assembly that receives impedance information from one or both of functional element 109 of expandable assembly 130 and/or functional element 109 of treatment assembly 160. EDU 250 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Fluid delivery assembly 200 can be configured to deliver a fluid to tissue and/or a component and/or assembly of system 10, such as to warm and/or cool the tissue, component and/or assembly. Fluid delivery assembly 200 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 109 of expandable assembly 130 and/or functional element 109 of treatment assembly 160, such as when functional elements 109 comprise a fluid delivery element such as a nozzle, an exit hole, a slit, or a permeable membrane. The cooling fluid can be supplied to a location within expandable assembly 130 and/or treatment assembly 160, such as when expandable assembly 130 and/or treatment assembly 160 comprises a balloon or other expandable reservoir configured to contact tissue. Alternatively or additionally, fluid delivery assembly 200 can be fluidly attached to another component of device 100 and/or system 10, the attached component not shown but configured to deliver fluid to tissue and/or a component of system 10 such as to add and/or absorb heat. Fluid delivery assembly 200 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

In some embodiments, fluid delivery assembly 200 includes a desiccant and/or drying assembly configured to dehydrate or otherwise remove moisture from one or more delivered gases prior to their delivery by device 100, device 500 and/or another device of system 10.

In some embodiments, system 10, device 100 and/or device 500 are constructed and arranged to perform a fractional treatment of tissue. Device 100 and/or device 500 can be constructed and arranged to treat target tissue with a fractional delivery of RF energy, such as monopolar and/or bipolar RF energy delivered from an array of electrodes positioned on an expandable element. In some embodiments, device 100 and/or device 500 are configured as a laser or other light energy delivery device constructed and arranged to provide a fractional energy delivery to target tissue. In some embodiments, device 100 and/or device 500 are configured to vaporize at least a portion of target tissue.

As described hereabove, system 10 can include one or more additional tissue expanding and/or tissue treating devices, such as second injectate delivery device 100' and/or treatment device 500. Device 500 and/or other treatment devices of the present inventive concepts can be configured to treat expand and/or target tissue TT in the same clinical procedure, or in a clinical procedure performed at least twenty-four hours after the first clinical procedure. Second device 100' can be of similar or dissimilar construction to device 100. In some embodiments, second device 100' comprises an expandable assembly with a different diameter than expandable assembly 130 of device 100. In some embodiments, second device 100' comprises a treatment element with a different construction and arrangement than treatment element 165 of device 100. In some embodiments, second device 100' comprises a device selected from the group consisting of: injectate delivery device; tissue expansion device; hot fluid filled balloon device; RF energy delivery device; vapor ablation device; cryoablation device; laser ablation device; ultrasound ablation device; mechanical abrasion device; and combinations of these. Second device 100' can comprise at least one fluid delivery element selected from the group consisting of: needle; water jet; iontophoretic element; and combinations of these. Second device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 110a and/or 110b. Imaging device 410 can be inserted through a separate working channel of endoscope 50, such as lumen 51. In one embodiment, imaging device 410 is an ultrasound transducer connected to a shaft, not shown but surrounded by shaft 110a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these Image and other information provided by imaging device 410 can be provided to an operator of system 10 and/or used by a component of system 10, such as controller 210, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery, tissue expansion and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 50 and/or another elongate device such that protective element 191 can be placed over or otherwise positioned to protect non-target tissue, such as tissue selected from the group consisting of: ampulla of Vater; bile duct; pancreas; pylorus; muscularis externae; serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described herein. System 10 can be configured to identify non-target tissue, such as via a camera used to identify the ampulla of Vater.

System 10 can be configured to prevent excessive or otherwise undesired distension of the duodenum such as distension that could cause tearing of the serosa. In some embodiments, system 10 is configured such that all tissue contacting components and/or fluids delivered by system 10 maintain forces applied on a GI wall below 2.0 psi, such as less than 1.2 psi. System 10 can be configured to avoid or otherwise minimize damage to the muscularis layer of the GI tract, such as by controlling pressure of target tissue treatment (e.g. via controlling expansion force of treatment assembly 160 and or expandable assembly 130) and/or by otherwise minimizing trauma imparted on any tissue by one or more components of system 10.

System 10 can further include one or more pharmaceutical and/or other agents 420, such as an agent configured for systemic and/or local delivery to a patient. Agents 420 can be delivered pre-procedurally, peri-procedurally and/or post-procedurally. Agents 420 can comprise one or more imaging agents, such an imaging agent used with imaging device 410. Agents 420 can be one or more pharmaceutical or agents configured to improve healing, such as agents selected from the group consisting of: antibiotics; steroids; mucosal cytoprotective agents such as sucralfate, proton pump inhibitors and/or other acid blocking drugs; and combinations of these. Alternative or in addition to agents 420, pre-procedural and/or post-procedural diets can be employed. For example, pre-procedural diets can include food intake that is low in carbohydrates and/or low in calories, and post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump Implant 192 can be inserted into the patient and remain implanted for a period of at least one month, at least 6 months or at least 1 year. In some embodiments, a first clinical procedure is performed treating target tissue, and a subsequent second clinical procedure is performed, as is described herein. In these two clinical procedure embodiments, a device can be implanted in the first clinical procedure, and removed in the second clinical procedure.

System 10 can include sizing device 430 which is constructed and arranged to be placed into one or more locations of the gastrointestinal tract or other internal location of the patient and measure the size or other geometric parameter of tissue. In some embodiments, sizing device 430 comprises a balloon, expandable cage or other sizing element constructed and arranged to measure the inner surface diameter of a tubular tissue such as duodenal and/or jejunal tissue. A diameter measurement can be performed by inflating a balloon of sizing device 430 to one or more predetermined pressures, or pressure profiles, and performing a visualization procedure or other procedure to determine balloon diameter. Alternatively or additionally, a balloon can be filled with a fluid and one or more of fluid volume or fluid pressure is measured to determine balloon diameter and subsequently diameter of tubular tissue proximate the balloon. In some embodiments, subsequent selection (e.g. size selection) and/or expansion diameter (e.g. sized for apposition) of expandable assembly 130, treatment assembly 160 and/or a treatment assembly of treatment device 500 can be determined using these tissue geometry measurements. Alternatively or additionally, an expandable element such as a balloon or cage can comprise two or more electrodes configured to provide a tissue impedance measurement whose value can be correlated to a level of apposition of the expandable element, and whose expanded diameter (e.g. visually measured) subsequently correlated to a diameter of tubular tissue proximate the expandable element. In some embodiments, treatment assembly 160 and/or expandable assembly 130 comprise sizing device 430, such as when treatment assembly 160 and/or expandable assembly 130 comprise a balloon or other sizing element used to measure a diameter of the inner surface of tubular tissue.

System 10 can be constructed and arranged to control one or more system parameters, such as controlling one or more system parameters prior to, during or after the delivery of a thermal dose of energy, during a priming procedure, during a sizing procedure and/or during a tissue expansion procedure. System 10 can be constructed and arranged to control a system parameter selected from the group consisting of: a priming procedure parameter such as priming temperature or priming duration; a target tissue treatment parameter such as target tissue temperature or target tissue treatment duration; fluid flow rate such as treatment fluid flow rate; a pressure parameter such as a treatment element pressure maintained during treatment of target tissue; a treatment element diameter such as a treatment element diameter maintained during treatment of target tissue; and combinations thereof. System 10 can be constructed and arranged to control the size of an expandable reservoir, such as by controlling the diameter of expandable assembly 130, treatment assembly 160 and/or another expandable reservoir as described herein. In some embodiments, a user of system 10 selects a size of an expandable reservoir, such as by selecting the size from a range of available sizes of expandable assembly 130 and/or treatment assembly 160 provided to the user in a kit.

Any of the components of system 10 can include a coating, such as a lubricious coating. In some embodiments, expandable assembly 130, treatment elements 165 and/or other radially expandable elements such as balloons include a lubricious or other material property modifying coating. In some embodiments, a radially expandable treatment assembly 160 and/or expandable assembly 130 comprise a hydrophilic coating, for example configured to disperse or otherwise move an ablative fluid.

Each of the components and/or devices of system 10 can be removably attached to another component, particularly device 100, treatment device 500, fluid delivery assembly 200, EDU 250, motion transfer assembly 260, ground pad 70, endoscope 50 and/or second device 100'. Typical attachment means include but are not limited to mechanical or electromechanical connectors providing an electrical, optical and/or fluidic connection between the attached components.

Figure 8:
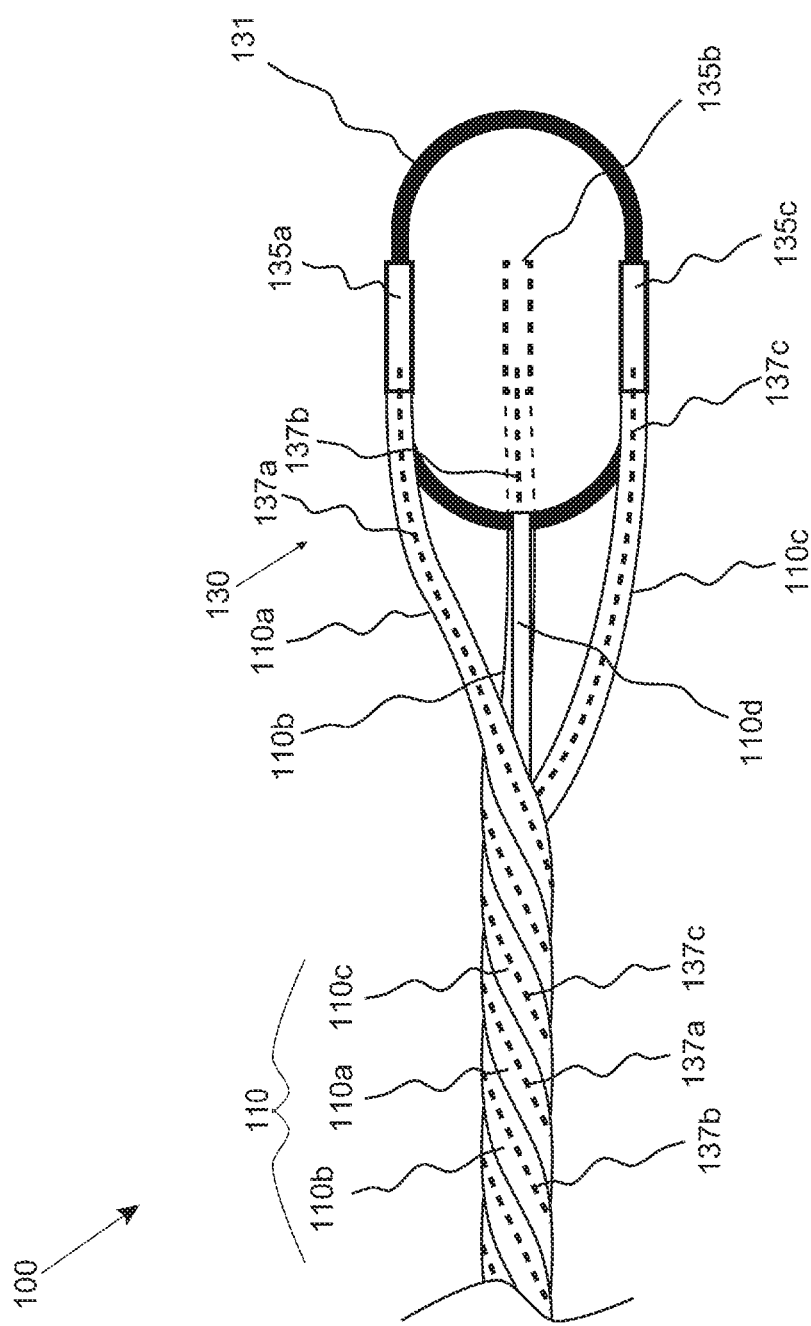
FIG. 8 is a side view of the distal portion of an injectate delivery device including multiple shafts arranged in a helix, consistent with the present inventive concepts.

Referring now to FIG. 8, a side view of the distal portion of an injectate delivery device including multiple shafts arranged in a helix is illustrated, consistent with the present inventive concepts. Device 100 comprises shaft 110 and expandable assembly 130, which comprises expandable element 131 (e.g. one or more balloons). Shaft 110 comprises multiple shafts, such as shafts 110*a*, 110*b*, 110*c*, and 110*d* shown. Shafts 110*a-c* are each arranged in a helical, spiral and/or otherwise twisted-shaft geometry (hereinafter helix or helical) about shaft 110*d*. Shaft 110*d* comprises one or more lumens, such as a lumen constructed and arranged to inflate expandable element 131. Tissue capture ports 135a, 135b, and 135c (singly or collectively port 135) are attached to expandable element 131, such as with equal 120° spacing along a circumference of expandable element 131 and positioned at a relative mid-portion of expandable element 131. Shafts 110a-c are operably attached to tissue capture ports 135a-c, respectively. Shafts 110a-c can each comprise multiple lumens, such as a vacuum lumen configured to deliver a vacuum to an attached tissue capture port 135 and a lumen configured to slidingly receive a fluid delivery tube 137 which includes a fluid delivery element 132 (for example a needle, not shown) at its distal end, such as is described hereabove in reference to FIG. 1.

As described above, in the embodiment of FIG. 8, shafts 110a-c are arranged in a helical arrangement along at least a portion of the length of shaft 110. In this helical arrangement, relatively similar advancement of the proximal ends of multiple fluid delivery tubes 137 causes relatively similar advancement of the distal ends of multiple fluid delivery tubes 137 (i.e. relatively similar advancement of multiple fluid delivery elements 131), even when shaft 110 is in a curvilinear geometry. This equilibration is due to the helix causing each shaft 110a-c to transition between the inner and outer radii of one or more curves when device 100 has been inserted through tortuous or otherwise curvilinear anatomy. If the shafts 110a-c were arranged in a relatively co-linear, non-helical arrangement, a lumen on the inside of a curve would traverse a shorter path length than a lumen on the outside of the curve. The helical arrangement of shafts 110a-c ensures that no lumen (or filament within the lumen) is consistently on either the inside or outside of a curved portion of shaft 110.

Shafts 110a-c can be arranged in a helix with a uniform or non-uniform pitch. In some embodiments, shafts 110a-c are arranged with a pitch such that each shaft spiral (e.g. rotates) between 360° (1 turn) and 1440° (4 turns) about a central axis (e.g. shaft 110d) along at least a portion of the length of shaft 110. In some embodiments, one or more continuous segments of shaft 110 comprise a helical portion. In some embodiments, shaft 110 comprises an arrangement of shafts 110a-c which spiral approximately 540° (1.5 turns) about shaft 110d along at least a portion of the length of shaft 110. In some embodiments, the helical portion of shaft 110 is a segment proximate expandable assembly 130 (e.g. in a distal portion of shaft 110). This helical arrangement of shafts 110a-c ensures that if shaft 110 is coiled in one or more directions, none of the lumens of shafts 110a-c are always on the inside or outside of a curved portion of shaft 110, minimizing differences in the lumen path lengths caused by shortening of a lumen in compression (inside of a curve) and/or extending of a lumen in tension (outside of a curve). Similar lumen path lengths result in similar travel distances in one or more filaments within the lumens, such as similar travel distances of fluid delivery tubes 137 during advancement and/or retraction of the associated fluid delivery element 132 into and/or out of tissue capture ports 135. The one or more helical portions of shaft 110 described hereabove enable the translation provided by a control on a proximal handle (e.g. slide 102 of handle 101 of FIG. 1) to accommodate shaft 110a-c lumen path length variations that result when shaft 110 is in a curved geometry.

Referring now to FIG. 9, a side sectional view of the distal portion of an injectate delivery device including a fluid delivery element positioned and oriented to penetrate tissue as tissue is captured within a tissue capture port is illustrated, consistent with the present inventive concepts. A distal portion of shaft 110 comprises a tissue capture port 135, which includes an opening 136. Positioned proximate opening 136 is the distal end of fluid delivery element 132, for example a sharpened needle. Fluid delivery element 132 is fluidly attached to fluid delivery tube 137. Tissue capture port 135 and opening 136 are in fluid communication with vacuum lumen 111. Shaft 110, tissue capture port 135, opening 136, fluid delivery tube 137, fluid delivery element 132, and/or vacuum lumen 111 can be of similar construction and arrangement to similar components described hereabove in reference to FIG. 1. The distal portion of fluid delivery element 132 is positioned and supported by block 151 and oriented such that the distal end faces opening 136.

Referring now to FIG. 9A, a side sectional anatomical view of the distal portion of the injectate delivery device of FIG. 9 is shown, after positioning proximate tissue T and application of a vacuum via lumen 111. The applied vacuum has caused a portion of tissue T to enter tissue capture port 135 via opening 136 and has caused the distal end of fluid delivery element 132 to penetrate tissue T. In a subsequent step, fluid can be delivered to tissue T via fluid delivery tube 137 and fluid delivery element 132 as has been described hereabove. In the embodiment of FIGS. 9 and 9A, fluid can be delivered to tissue T while avoiding advancement of fluid delivery tube 137 and fluid delivery element 132 (e.g. avoiding the need for separate controls and other mechanisms to translate fluid delivery tube 137 and fluid delivery element 132). Positive pressure can be introduced via lumen 111 to eject tissue from tissue capture port 135 (e.g. after fluid is delivered to achieve sufficient tissue expansion).

Figure 10A:
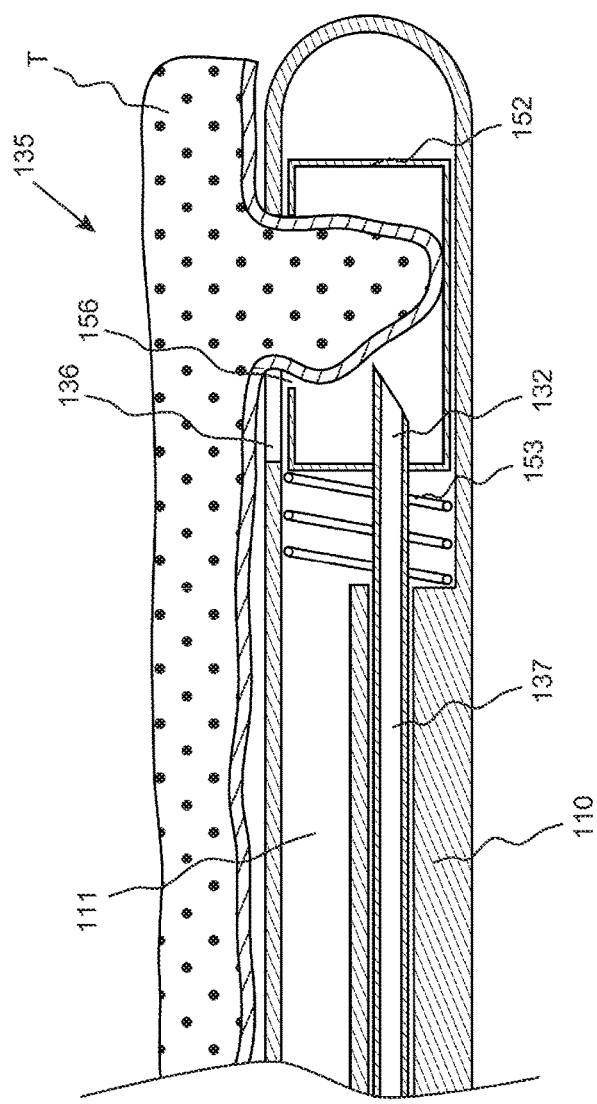
FIGS. 10A and 10B are side sectional anatomical views of the distal portion of an injectate delivery device prior to and after translation of a tissue port carriage via applied vacuum, consistent with the present inventive concepts.
Figure 10B:
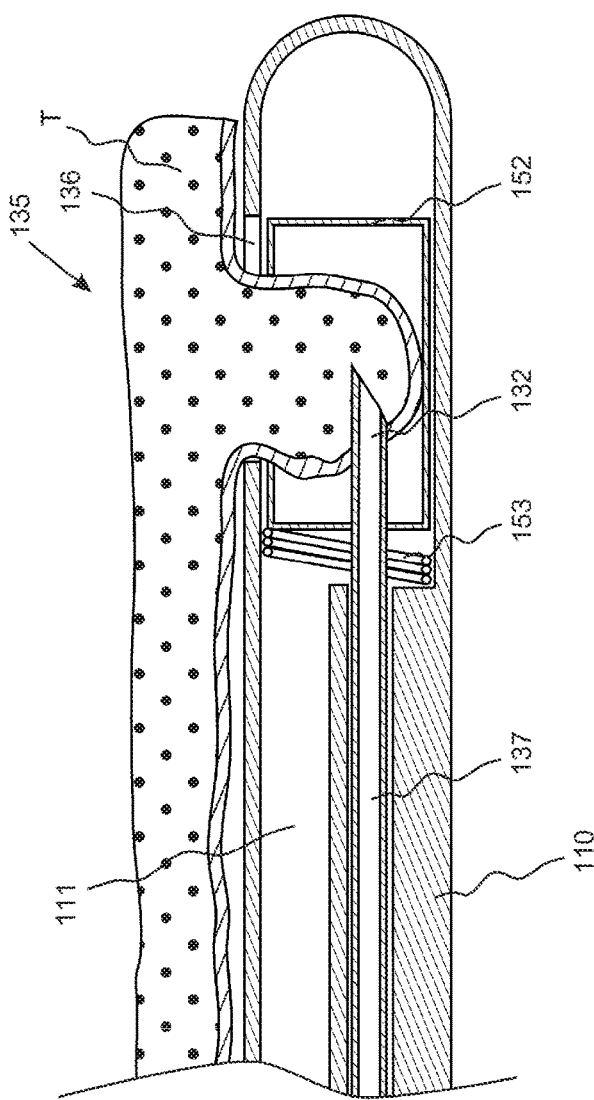

Referring now to FIGS. 10A and 10B, side sectional anatomical views of the distal portion of an injectate delivery device prior to and after translation of a tissue port carriage via applied vacuum is illustrated, consistent with the present inventive concepts. A distal portion of shaft 110 comprises a tissue capture port 135, which includes an opening 136. Positioned proximate opening 136 is the distal end of fluid delivery element 132, for example a sharpened needle. Fluid delivery element 132 is fluidly attached to fluid delivery tube 137. Opening 136 is in fluid communication with vacuum lumen 111. Shaft 110, tissue capture port 135, opening 136, fluid delivery tube 137, fluid delivery element 132, and/or vacuum lumen 111 can be of similar construction and arrangement to similar components described hereabove in reference to FIG. 1.

Positioned within tissue capture port 135 is carriage 152. Carriage 152 is slidingly positioned within tissue capture port 135 as shown. Carriage 152 is constructed and arranged to receive tissue T through opening 156 when vacuum is applied via lumen 111, such as is shown in FIG. 10A. Carriage 152 is biased toward the distal end of shaft 110 (i.e. biased toward the right of the page) by spring 153. Once tissue T fills opening 156 (i.e. forms a relatively seal about opening 156), the applied vacuum causes carriage 152 to translate proximally (i.e. to the left of the page), which causes the distal end of fluid delivery element 132 to penetrate the captured tissue T. In a subsequent step, fluid can be delivered to tissue T via fluid delivery tube 137 and fluid delivery element 132 as has been described hereabove.

When vacuum is removed from lumen 111, spring 153 translates carriage 152 distally such that fluid delivery element 132 is removed from tissue T. Removal of vacuum from lumen 111 can cause tissue T can evacuate carriage 152. In some embodiments, a positive pressure is applied via lumen 111 to remove tissue T from carriage 152 (e.g. after fluid is delivered to achieve sufficient tissue expansion). In the embodiment of FIGS. 10A and 10B, fluid can be delivered to tissue T while avoiding advancement of fluid delivery tube 137 and fluid delivery element 132 (e.g. avoiding the need for separate controls and other mechanisms to translate fluid delivery tube 137 and fluid delivery element 132).

Referring now to FIGS. 11A and 11B, side sectional anatomical views of the distal portion of an injectate delivery device prior to and after translation of a tissue port carriage via retraction of a control rod is illustrated, consistent with the present inventive concepts. A distal portion of shaft 110 comprises a tissue capture port 135, which includes an opening 136. Positioned proximate opening 136 is the distal end of fluid delivery element 132, for example a sharpened needle. Fluid delivery element 132 is fluidly attached to fluid delivery tube 137. Opening 136 is in fluid communication with vacuum lumen 111. Shaft 110, tissue capture port 135, opening 136, fluid delivery tube 137, fluid delivery element 132, and/or vacuum lumen 111 can be of similar construction and arrangement to similar components described hereabove in reference to FIG. 1.

Positioned within tissue capture port 135 is carriage 152. Carriage 152 is slidingly positioned within a distal portion of shaft 110 as shown. Carriage 152 is constructed and arranged to receive tissue T through opening 156 when vacuum is applied via lumen 111, such as is shown in FIG. 11A. Carriage 152 is attached to control rod 154, such that advancement and retraction of control rod 154 causes subsequent distal and proximal translation, respectively, of carriage 152. Control rod 154 travels proximally within shaft 110, such as to attach to one or more controls of a proximal handle, not shown but such as is described hereabove in reference to FIG. 1. Carriage 152 can be biased in a distal position by control rod 154 and/or a biasing mechanism of a proximal handle. Alternatively or additionally, carriage 152 can include spring 153, such as to bias carriage 152 distally. Once tissue T has been captured within carriage 152 via vacuum applied via lumen 111, control rod 154 can be retracted to cause the distal end of fluid delivery element 132 to penetrate the captured tissue T. In a subsequent step, fluid can be delivered to tissue T via fluid delivery tube 137 and fluid delivery element 132 as has been described hereabove.

Advancement of control rod 154 causes translation of carriage 152 distally, such that fluid delivery element 132 is removed from tissue T. Removal of vacuum from lumen 111 can cause tissue T can evacuate carriage 152. In some embodiments, a positive pressure is applied (e.g. via lumen 111) to remove tissue T from carriage 152. In the embodiment of FIGS. 11A and 11B, fluid can be delivered to tissue T while avoiding advancement of fluid delivery tube 137 and fluid delivery element 132. In an alternative embodiment, control rod 154 comprises a hydraulic or pneumatic tube used to translate carriage 152.

Figure 12:
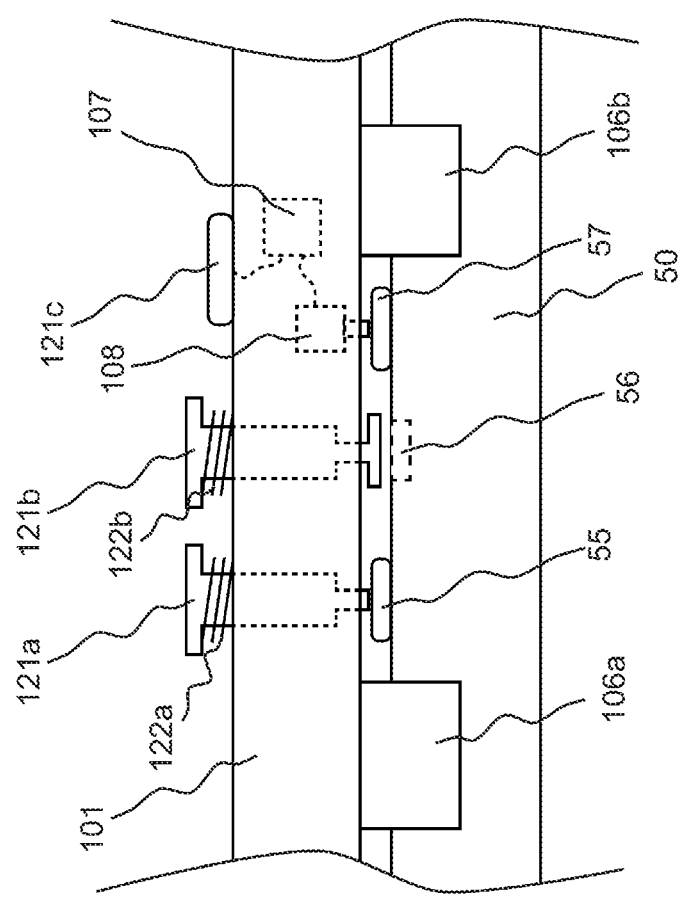
FIG. 12 is a side view of a portion of a handle of an injectate delivery device that is operably attached to a separate device and configured to control one or more functions of the separate device, consistent with the present inventive concepts.

Referring now to FIG. 12, a side view of a portion of a handle of an injectate delivery device that is operably attached to a separate device and configured to control one or more functions of the separate device is illustrated, consistent with the present inventive concepts. Handle 101 can be a portion of handle 101 of FIG. 1 described hereabove, such as to advance and retract one or more fluid delivery elements of the present inventive concepts, to apply a vacuum, to control delivery of fluids, and/or to control a separate device, all as have been described in detail hereabove. Handle 101 includes attachment elements 106a and 106b, which can be constructed and arranged to attach to a separate device such as endoscope 50 shown. Attachment elements 106a and/or 106b can comprise an element selected from the group consisting of: clip; clamp; strap; electromagnetic coupler such as a solenoid-based clamp; adhesive strip; and combinations thereof.

Attachment elements 106a and/or 106b, and/or another portion (e.g. a control) of handle 101 can be operably connected (e.g. mechanically linked), with one or more controls of the attached device, such as to allow a clinician to control each device simply by accessing handle 101. Handle 101 of FIG. 12 comprises controls 121a, 121b and 121c. One or more of controls 121a-c can be positioned on attachment element 106a or 106b, as shown in FIG. 1, such as to allow a clinician or other operator to remotely control endoscope 50. Control 121a comprises a depressible button which is biased in the up position (e.g. off position) by spring 122a. Pressing of control 121a activates depressible button 55 of endoscope 50, such as a button used to perform a function selected from the group consisting of: activating a camera; modifying flow of insufflation fluid or flushing fluid; advancing or retracting a shaft; delivering energy; and combinations of these. Control 121b comprises a depressible button which is biased in the up position (e.g. off position) by spring 122b. Pressing of control 121b covers and seals port 56 of endoscope 50, such as an opening used to activate a vacuum when covered and sealed. Control 121c comprises an electrical switch which is electrically attached to electronics module 107. Activation (e.g. pressing) of control 121c causes activation of solenoid 108 which in turns activates control 57 of endoscope 50. Control 57 can be used to activate and/or modify one or more functions of endoscope 50 such as have been described in reference to button 55 and port 56 of endoscope 50. One or more of controls 121a, 121b and 121c can be used to control various elements of the attached device, such as an element selected from the group consisting of: suction valve; vent hole; air or water valve; channel opening such as a biopsy channel opening; suction connector; air supply connector; water supply connector; and combinations of these.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. An injectate delivery device for expanding tissue comprising:
   at least one fluid delivery tube comprising a proximal end, a distal end and a lumen therebetween;
   at least one fluid delivery element in fluid communication with the at least one fluid delivery tube lumen;
   a radially expanding element comprising the at least one fluid delivery element;
   a supply of vacuum constructed and arranged to cause tissue to tend toward the at least one fluid delivery element; and
   at least one operator activated control constructed and arranged to:
   expand the radially expandable element; and activate the supply of vacuum;
advance the at least one fluid delivery element; and
a force limiting assembly constructed and arranged to limit the force applied to the at least one fluid delivery element during the advancement by the at least one operator activated control, wherein the at least one operator activated control is attached to the at least one fluid delivery tube by the force limiting assembly, and wherein the force limiting assembly comprises at least one spring;
wherein the device is constructed and arranged to deliver an injectate to target tissue through the at least one fluid delivery element.

2. The injectate delivery device according to claim 1, wherein the at least one control is further constructed and arranged to advance the at least one fluid delivery element.

3. The injectate delivery device according to claim 2, wherein the at least one control is constructed and arranged to advance the at least one fluid delivery element while limiting force applied to the at least one fluid delivery element.

4. The injectate delivery device according to claim 2, further comprising a compression element operably connecting the at least one control to the at least one fluid delivery tube.

5. The injectate delivery device according to claim 2, wherein the at least one fluid delivery tube comprises multiple fluid delivery tubes and the at least one fluid delivery element comprises multiple fluid delivery elements each attached to a fluid delivery tube, and wherein the at least one control is constructed and arranged to advance the multiple fluid delivery tubes.

6. The injectate delivery device according to claim 1, wherein the at least one control is further constructed and arranged to manipulate tissue toward the fluid delivery element such that the at least one fluid delivery element penetrates the tissue.

7. The injectate delivery device according to claim 1, wherein the at least one control is further constructed and arranged to initiate the flow of injectate through the at least one fluid delivery element and into tissue.

8. The injectate delivery device according to claim 1, wherein the at least one control is further constructed and arranged to modify the flow of injectate into tissue.

9. The injectate delivery device according to claim 1, wherein the at least one control is further constructed and arranged to compact the radially expandable element.

10. The injectate delivery device according to claim 1, wherein the at least one control is further constructed and arranged to control a separate device.

11. The injectate delivery device according to claim 1, further comprising at least one vacuum lumen fluidly attached to the supply of vacuum, wherein the at least one control is further constructed and arranged to apply a positive pressure to the at least one vacuum lumen.

12. The injectate delivery device according to claim 1, wherein the at least one control comprises multiple controls.

13. The injectate delivery device according to claim 1, wherein the at least one control comprises one or more controls selected from the group consisting of: electrical control; mechanical control; button; knob; switch; lever; touchscreen; and combinations thereof.

14. The injectate delivery device according to claim 1, wherein the at least one control comprises a control biased in an off state.

15. The injectate delivery device according to claim 1, wherein the at least one fluid delivery element comprises one or more elements selected from the group consisting of: needle; fluid jet; iontophoretic element; a porous element; and combinations thereof.

16. The injectate delivery device according to claim 1, wherein the at least one fluid delivery element comprises one or more needles.

17. The injectate delivery device according to claim 16, wherein at least one fluid delivery element comprises a needle with a diameter greater than 30 ga.

18. The injectate delivery device according to claim 17, wherein at least one fluid delivery element comprises a needle with a diameter greater than 27 ga.

19. The injectate delivery device according to claim 16, wherein the at least one fluid delivery element comprises a curved needle.

20. The injectate delivery device according to claim 1, wherein the at least one fluid delivery element comprises multiple fluid delivery elements.

21. The injectate delivery device according to claim 20, wherein the multiple fluid delivery elements comprise at least three fluid delivery elements disposed in a circumferential array.

22. The injectate delivery device according to claim 1, wherein the radially expandable element is constructed and arranged to apply a force to luminal tissue at a pressure of no more than 2.0 psi.

23. The injectate delivery device according to claim 1, wherein the radially expandable element is constructed and arranged to contact luminal tissue at a pressure of at least 0.6 psi as the injectate is delivered to the target tissue.

24. The injectate delivery device according to claim 1, wherein the radially expandable element is constructed and arranged to expand to a target diameter in less than 60 seconds.

25. The injectate delivery device according to claim 1, wherein the radially expandable element comprises a proximal portion attached to multiple fluid delivery tubes, wherein the multiple fluid delivery tubes define an opening positioned proximate the radially expandable element proximal portion and sized to receive the distal end of an elongate device positioned within 9 cm of the radially expandable element proximal portion.

26. The injectate delivery device according to claim 1, further comprising a handle, wherein the handle comprises the at least one control.

27. The injectate delivery device according to claim 1, further comprising a handle including a user interface, wherein the user interface comprises the at least one control.

28. The injectate delivery device according to claim 27, wherein the handle user interface is constructed and arranged to display information selected from the group consisting of: fluid delivery element position; vacuum status; occlusion status; expandable element status; volume of injection from the at least one fluid delivery element; total injected volume of injectate; pressure of injection; catheter position relative to the papilla; number of completed injections; and combinations thereof.

29. The injectate delivery device according to claim 1, further comprising a handle with a first portion constructed and arranged for use in a plurality of medical procedures, and a second portion constructed and arranged for fewer uses than the first.

30. The injectate delivery device according to claim 1, further comprising a handle comprising an attachment element constructed and arranged to removably attach to an endoscope.

31. The injectate delivery device according to claim 1, further comprising a fluid delivery assembly, wherein the at least one control is configured to control a fluid delivery assembly parameter.

32. The injectate delivery device according to claim 31, wherein the fluid delivery assembly comprises the at least one control.

33. The injectate delivery device according to claim 1, further comprising a second device, wherein the at least one control controls the second device.

34. The injectate delivery device according to claim 33, wherein the second device comprises a device selected from the group consisting of: an endoscope; an energy delivery device; a fluid delivery assembly; and combinations thereof.

35. The injectate delivery device according to claim 1, further comprising a tissue capture port surrounding the at least one fluid delivery element.

36. The injectate delivery device according to claim 35, wherein the tissue capture port comprises an opening, and wherein the opening comprises a dimension selected from the group consisting of: length of at least 0.1"; length of between 0.14" and 0.20"; length of approximately 0.16"; width of at least 0.4"; width of between 0.05" and 0.08"; width of approximately 0.06".

37. The injectate delivery device according to claim 35, wherein the at least one fluid delivery element is constructed and arranged to travel from a retracted position to an advanced position and remain within the tissue capture port for the length of travel.

38. The injectate delivery device according to claim 1, further comprising the injectate delivered by the at least one fluid delivery element to the target tissue.

39. The injectate delivery device according to claim 38, wherein the injectate comprises a material selected from the group consisting of: water; saline; dye; visible dye; indigo carmine; methylene blue; India ink; a gel; a hydrogel; a protein hydrogel; a visualizable media; an x-ray visualizable media; an ultrasonically visualizable media; an MRI visualizable media; and combinations thereof.

40. The injectate delivery device according to claim 38, wherein the injectate comprises a material selected from the group consisting of: a biopolymer; ethylene vinyl alcohol; an adhesive; cyanoacrylate; and combinations thereof.

41. The injectate delivery device according to claim 1, further comprising a mechanical stop constructed and arranged to limit the advancement of the at least one fluid delivery element.

42. The injectate delivery device according to claim 1, wherein the injectate delivery device comprises a distal end and a bulbous tip positioned on the distal end, wherein the bulbous tip comprises a diameter of at least 2 mm.

43. The injectate delivery device according to claim 1, further comprising an elongate shaft with a proximal end and a distal portion.

44. The injectate delivery device according to claim 43, wherein the elongate shaft comprises multiple shafts.

45. The injectate delivery device according to claim 44, wherein the multiple shafts comprise a helical arrangement along at least a portion of the elongate shaft.

46. The injectate delivery device according to claim 43, further comprising a steering mechanism positioned within the shaft.

47. The injectate delivery device according to claim 1, further comprising an elongate shaft and a camera positioned within the elongate shaft.

48. The injectate delivery device according to claim 1, wherein the injectate delivery device is constructed and arranged to deliver insufflation fluid.

49. The injectate delivery device according to claim 1, wherein the expanded tissue comprises a tissue layer of the gastrointestinal tract.

50. The injectate delivery device according to claim 49, wherein the expanded tissue layer comprises one or more layers of submucosal tissue.

51. The injectate delivery device according to claim 50, wherein the expanded tissue layer comprises one or more layers of duodenal submucosal tissue.

52. The injectate delivery device according to claim 1, wherein the injectate delivery device is constructed and arranged to perform an approximately full circumferential expansion of luminal wall tissue.

53. The injectate delivery device according to claim 1, wherein the injectate delivery device is constructed and arranged to create a therapeutic restriction in the gastrointestinal tract.

54. A system comprising the injectate delivery device according to any of claims 1 through 53, further comprising a component selected from the group consisting of:
an endoscope;
injectate for delivery through the at least one fluid delivery element;
an ablation catheter comprising a treatment element for treating target tissue proximate the expanded tissue layer;
a sizing device constructed and arranged to provide lumen diameter information;
a guidewire;
and combinations thereof.

55. The system of according to claim 54, wherein the system is constructed and arranged to treat a disease or disorder selected from the group consisting of: diabetes; obesity or otherwise being overweight; hypercholesterolemia; exercise intolerance; psoriasis; hypertension; metabolic syndrome; and combinations thereof.

* * * * *